United States Patent [19]
Dionne et al.

[11] Patent Number: 5,516,771
[45] Date of Patent: May 14, 1996

[54] USE OF INDOLOCARBAZOLE DERIVATIVES TO TREAT A PATHOLOGICAL CONDITION OF THE PROSTATE

[75] Inventors: Craig A. Dionne, Harleysville; Patricia C. Contreras, West Chester, both of Pa.; Chikara Murakata, Tokyo, Japan

[73] Assignees: Cephalon, Inc., West Chester, Pa.; Kyowa Hakko Kogyo Co., Ltd., Tokyo, Japan

[21] Appl. No.: 250,175

[22] Filed: May 27, 1994

Related U.S. Application Data

[63] Continuation-in-part of Ser. No. 96,622, Jul. 22, 1993, abandoned, which is a continuation-in-part of Ser. No. 69,178, May 28, 1993.

[51] Int. Cl.$^6$ .................................................. A61K 31/55
[52] U.S. Cl. .......................... 514/211; 514/410; 540/543; 540/545; 548/416
[58] Field of Search ............................ 514/211; 540/543, 540/545

[56] References Cited

U.S. PATENT DOCUMENTS

| | | | |
|---|---|---|---|
| 4,877,776 | 10/1989 | Murakata et al. | 514/43 |
| 4,923,986 | 5/1990 | Murakata et al. | 540/545 |
| 5,043,335 | 8/1991 | Kleinschroth et al. | 514/211 |
| 5,073,633 | 12/1991 | Schroeder et al. | 540/545 |

FOREIGN PATENT DOCUMENTS

| | | |
|---|---|---|
| 0558962A1 | 8/1993 | European Pat. Off. |
| 62-155285 | 7/1987 | Japan |
| 62-155284 | 7/1987 | Japan |
| 63-295588 | 12/1988 | Japan |
| WO93/00909 | 1/1993 | WIPO |
| WO/93/08809 | 5/1993 | WIPO |
| WO/94/02488 | 2/1994 | WIPO |

OTHER PUBLICATIONS

Akinaga et al., "Antitumor Effect of KT6124, A Novel Derivative of Protein Kinase Inhibitor K–252A, and Its Mechanism of Action", Cancer Chemother. Pharmacol. 29:266–272 (1992).
Berg et al., "K–252a Inhibits Nerve Growth Factor–Induced trk Photo–Oncogene Tyrosine Phosphorylation and Kinase Activity", J. Biological Chem. 267:13–16 (1992).
Brocker et al., "Nerve Growth and Expression of Receptors for Nerve Growth Factor in Tumors of Melanocyte Origin", J. Investigative Dermatology 96:662–665 (1991).
Cunha et al., "Normal and Abnormal Development of the Male Urogenital Tract", J. Andrology, 13:465–475 (1992).
Djakiew et al., "Regulation of Growth by a Nerve Growth Factor–Like Protein Which Modules Paracrine Interactions Between a Neoplastic Epithelial Cell Line . . . , " Cancer Research 51:3304–3310 (1991).
Elliott et al., "K252a is a Potent and Selective Inhibitor of Phosphorylase Kinase", Biochemical and Biophysical Research Communications 171:148–154 (1990).
Hashimoto et al., "Blockage of Nerve Growth Factor Action in PC12h Cells by Staurosporine, A Potent Protein Kinase Inhibitor", J. Neurochemistry 53:1675–1685 (1989).
Hempstead et al., "Overexpression of the trk Tyrosine Kinase Rapidly Accelerates Nerve Growth Factor–Induced Differentiation", Neuron 9:883–896 (1992).
Mac Morgan et al., "Expression of Nerve Growth Factor and Nerve Growth Factor Receptor Genes in Human Tissues and in Prostatic Adenocarcinoma Cell Lines", J. Neurochemistry, 59:1381–1390 (1992).
Nakagawa et al., "Association Between High Levels of Expression of the trk Gene and Favorable Outcome in Human Neuroblastoma", New England J. Medicine 328:847–854 (1993).
Nye et al., "K–252a and Staurosporine Selectively Block Autophosphorylation of Neurotrophin Receptors and Neurotrophin–Mediated Responses", Molecular Biology of the Cell 3:677–686 (1992).
Tapley et al., "K252a is a Selective Inhibitor of the Tyrosine Protein Kinase Activity of the trk Family of Oncogenes and Neurotrophin Receptors", Oncogene 7:371–381 (1992).
Morton et al., "Differential Effects of Growth Factor Antagonists on Neoplastic and Normal Prostatic Cells", The Prostate 17:327–336 (1990).
Ichikawa et al., "The Antitumor Effects of Quinoline–3–Carboxamide Linomide on Dunning R–3327 Rat Prostatic Cancers", Cancer Research 52:3022–3028 (1992).
Issacs et al., "Establishment and Characterization of Seven Dunning Rat Prostatic Cancer Cell Lines and Their Use in Developing Methods for Predicting . . . ", The Prostate 9:261–281 (1986).
Eisenberger et al., "Suramin, An Active Drug for Prostate Cancer: Interim Observations in a Phase I Trial", J. of Nat. Cancer Institute 85:611–621 (1993).
Bozyczko–Coyne et al., "A Rapid Fluorometric Assay to Measure Neuronal Survival in Vitro", Journal of Neuroscience Methods, 50:205–216 (1993).
Hughes et al., "Synthesis of the Indolo[2,3-A]Carbazole Natural Products Staurosporinone and Arcyiaflavin B", J. Chem. Soc. Perkin Trans. 1:2475–2480 (1990).
Hirata et al., Chemical Abstracts, vol. 111, No. 21, Issued Nov. 20, 1989, Abstract 194456g.
Tishler et al., Chemical Abstracts, vol. 113, No. 21, Issued Nov. 19, 1990.

*Primary Examiner*—Richard L. Raymond
*Attorney, Agent, or Firm*—Richard P. Burgoon, Jr.; Fish & Richardson

[57] ABSTRACT

The invention features a method of treating a pathological condition of the prostate gland, e.g., benign prostatic hypertrophy or prostate cancer, in a mammal, said method comprising administering to said mammal a therapeutic amount of the indolocarbazole compound K-252$a$ or a preferred derivative thereof. The invention also includes novel derivatives of K-252$a$.

12 Claims, 6 Drawing Sheets

USE OF INDOLOCARBAZOLE DERIVATIVES TO TREAT A PATHOLOGICAL CONDITION OF THE PROSTATE

This application is a Continuation-in-Part of U.S. Ser. No. 08/096,622 filed Jul. 22, 1993, now abandoned, which is a Continuation-in-Part of U.S. Ser. No. 08/069,178 filed May 28, 1993.

BACKGROUND OF THE INVENTION

The invention relates to the use of the indolocarbazole compound K-252a, or a preferred derivative thereof, to treat a pathological condition of the prostate gland.

Disorders of the prostate gland are common in aging men. For example, prostatic hyperplasia affects 90% of men by the age of 80 years. Where the hyperplastic condition causes urinary obstruction, it is alleviated by surgical techniques. Prostate cancer, which is now the most frequently diagnosed cancer in men, is most frequently treated by surgery, by radiation therapy, or by androgen deprivation, e.g., by castration, by estrogen therapy, by administration of analogues of adrenocorticotropic hormone (ACTH) (*Harrison's Principles of Internal Medicine,* 12th ed. Wilson et al. eds. McGraw-Hill, New York. pgs. 1629–32), or by administration of Suramin, a non-specific and highly toxic growth factor inhibitor.

The neurotrophin family of growth factors includes nerve growth factor (NGF), brain derived neurotrophic factor (BDNF), neurotrophin-3 (NT-3) and neurotrophin 4/5 (NT-4/5). These basic proteins are approximately 120 amino acids in length, share ≈50% sequence homology, and are highly conserved among mammalian species (Issackson et al., *FEBS Lett.* 285:260–64, 1991). NGF was the first growth factor discovered and remains the best characterized neurotrophin. NGF is required for normal development of sensory and sympathetic neurons and for normal function of these cells in adult life (Levi-Montalcini, *Annu.Rev.Neurosci.* 5:341– 362, 1982; Yankner et al., *Annu. Rev. Biochem* 51:845–868, 1982).

Neurotrophin binding and activation of a set of high affinity receptors (trks) is necessary and sufficient to mediate most of the biological effects of the neurotrophins. The trks are transmembrane proteins which contain an extracellular ligand binding domain, a transmembrane sequence, and a cytoplasmic tyrosine kinase domain. The trks comprise a family of structurally related proteins with preferential binding specificities for the individual neurotrophins. TrkA, which is sometimes referred to as trk, is a high-affinity receptor for NGF, but it can also mediate biological responses to NT-3 under particular conditions (Kaplan et al. *Science* 252:554–558, 1991; Klein et al., *Cell* 65.:189–197, 1991; Cordon-Cardo et al., *Cell* 66:173–183, 1991). TrkB binds and mediates functions of BDNF, NT-3, and NT4/5 (Klein et al. *Cell* 66:395–403, 1991; Squinto et al., *Cell* 65:885–893, 1991; Klein et al. *Neuron* 8:947–956, 1992). TrkC is relatively specific for NT-3 (Lamballe et al., *Cell* 66:967–979, 1991).

K-252a, an alkaloid-like material isolated from the culture broth of Nocardiosis sp. and Actinomadula sp. is an inhibitor of protein kinase C, A, and G, as well as myosin light-chain kinase and phosphorylase kinase.

SUMMARY OF THE INVENTION

The invention features a method of treating a pathological condition of the prostate gland in a mammal, the condition being one that results from an excessive proliferation of prostate cells. The method involves administering to the mammal a therapeutic amount of an indolocarbazole compound, e.g., K-252a, or a functional derivative thereof.

Certain functional derivatives of K-252a can be used to prevent prostate tissue growth, and thereby to attenuate or cause regression of conditions exhibited by pathological proliferation of prostate cells, e.g., benign prostatic hypertrophy, or prostatic cancer, i.e., locally confined or metastatic prostate cancer. An excessive, or pathological, proliferation of prostate cells can be indicated by any one of a number of cellular changes, including but not limited to neoplastic transformation, an altered ratio of fibromuscular (stromal) cells to epithelial (secretory) cells in the prostate, or by a gross change in the degree of prostate gland enlargement or swelling. This may result in a symptom such as hesitancy, poor urinary stream, intermittent urinary flow, or growth of cells outside the organ capsule.

By a "functional derivative of K-252a" is meant a K-252a derivative that inhibits the tyrosine kinase (TK) activity associated with a neurotrophin receptor, e.g., trkA, trkB or trkC. Preferably the neurotrophin receptor is trkA, and is activated when contacted by NGF. The TK activity of the trks in the presence of the K-252a derivative is preferably less than the TK activity of the trks in the absence of the K-252a derivative. The TK activity of the trks can be measured according to the methods disclosed herein.

Functional derivatives within the scope of the invention can be represented by the formula I. Preferred formula I compounds are hereafter referred to as compounds I-1 through I-76 inclusive. The functional derivatives that are represented by the formula I are:

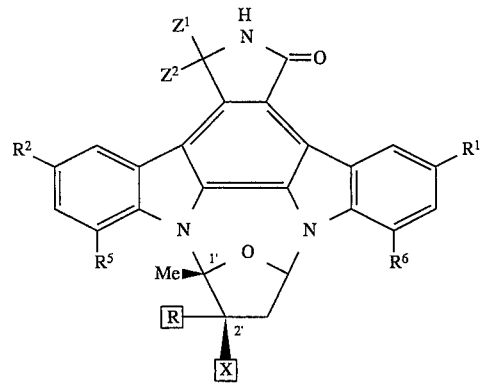

wherein:
a) when $Z^1$ and $Z^2$ are both hydrogen:
 1) R is selected from the group consisting of OH, O-n-alkyl of 1–6 carbons, and O-acyl of 2–6 carbons;
 2) X is selected from the group consisting of H; $CONHC_6H_5$ with the proviso that both $R^1$ and $R^2$ are not Br;
 $CH_2Y$ wherein Y is:
  $OR^7$ wherein $R^7$ is H or acyl of 2–5 carbons, preferably acetyl;
  $SOR^8$ wherein $R^8$ is alkyl of 1–3 carbons, aryl, or heterocyclic group including a nitrogen atom;
  $NR^9R^{10}$ wherein $R^9$ and $R^{10}$, independently, are H, alkyl of 1–3 carbons, Pro, Ser, Gly, Lys, or acyl of 2–5 carbons, with the proviso that only one of $R^9$ and $R^{10}$ is Pro, Ser, Gly, Lys or acyl;
  $SR^{16}$ wherein $R^{16}$ is an aryl, alkyl of 1–3 carbons, or a heterocyclic group that includes a nitrogen atom;

$N_3$; $CO_2CH_3$; S-Glc;
$CONR^{11}R^{12}$ wherein $R^{11}$ and $R^{12}$, independently, are H, alkyl of 1–6 carbons, $C_6H_5$, hydroxyalkyl of 1–6 carbons, or $R^{11}$ and $R^{12}$ are combined to form $-CH_2CH_2OCH_2-CH_2-$;
$CO_2CH_3$; $CH=NNHCONH_2$; CONHOH; $CH=NOH$; $CH=NNHC(=NH)NH_2$;

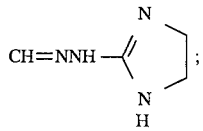

$CH=NN(R^{17})_2$ wherein $R^{17}$ represents aryl, $CH_2NHCONHR^{18}$ wherein $R^{18}$ is lower alkyl or aryl; or X and R are combined together to form $-CH_2NHCO_2-$, $-CH_2OC(CH_3)_2O-$, $=O$, or $-CH_2N(CH_3)CO_2-$;

3) $R^1$, $R^2$, $R^5$ and $R^6$, are each independently, H or up to two of them are F, Cl, Br, I, $NO_2$, CN, OH; $NHCONHR^{13}$ wherein $R^{13}$ is $C_6H_5$ or alkyl of 1–3 carbons with the proviso that only one of $R^1$, $R^2$, $R^5$ and $R^6$ is $NHCONHR^{13}$; $CH_2OR^{13}$; alkyl of 1–3 carbons; $CH_2OCONHR^{14}$; $NHCO_2R^{14}$ in which $R^{14}$ is lower alkyl; $CH(SC_6H_5)_2$; or $CH(-SCH_2CH_2S-)$; or $R^1$ is $CH_2S(O)_pR^{21}$ where p=0 or 1 and $R^{21}$ is aryl, alkyl of 1–3 carbons, a heterocyclic group that includes a nitrogen atom,

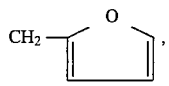

or $CH_2CH_2N(CH_3)_2$, and $R^2$, $R^5$ and $R^6$ are H; or $R^1$ is $CH=NNR^{22}R^{23}$, wherein $R^{22}$ and $R^{23}$, are each independently H, alkyl of 1–3 carbons, $C(=NH)NH_2$, or a heterocyclic group that includes a nitrogen atom, or $R^{22}$ and $R^{23}$ are combined together to form $-(CH_2)_4-$, $-(CH_2CH_2OCH_2CH_2)-$, or $-CH_2CH_2N(CH_3)CH_2CH_2)-$, with the proviso that $R^{22}$ and $R^{23}$ cannot both be H, and at least one of $R^{22}$ or $R^{23}$ is H except when both are alkyl, and $R^2$, $R^5$ and $R^6$ are H;

and:

b) when $Z^1$ and $Z^2$ are both combined together to represent O; X is $CO_2CH_3$; R is OH and $R^1$, $R^2$, $R^5$ and $R^6$ are each hydrogen.

Functional derivatives within the scope of the invention can also be represented by the formula II. Preferred formula II derivatives are hereafter referred to as compounds II-1 through II-4, inclusive. The functional derivatives that are represented by the formula II are:

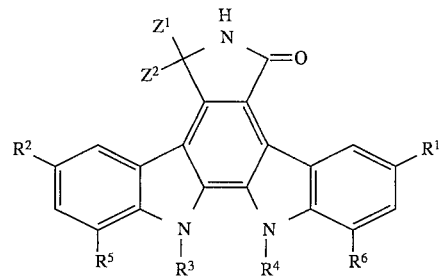

wherein:

a) $R^3$ and $R^4$ are each independently selected from the group consisting of H, alkyl of 1–6 carbons, hydroxyalkyl of 1–3 carbons, and alkenyl of 3–6 carbons, with the proviso that both $R^3$ and $R^4$ are not H;

b) $Z^1$ and $Z^2$ are both hydrogen and $R^1$, $R^2$, $R^5$ and $R^6$ are each independently H or up to two of them are F, Cl, Br, I, $NO_2$, CN, or OH; $NHCONHR^{13}$ wherein $R^{13}$ is $C_6H_5$ or alkyl of 1–3 carbons with the proviso that only one of $R^1$, $R^2$, $R^5$ and $R^6$ is $NHCONHR^{13}$; $CH_2OR^{13}$; alkyl of 1–3 carbons; $CH_2OCONHC_2H_5$; or $NHCO_2CH_3$; and c) when $Z^1$ and $Z^2$ are both combined together to represent O; and $R^1$, $R^2$, $R^5$, and $R^6$ are each hydrogen.

Preferred Formula I, Formula II, Formula III, Formula IV, Formula V, and Formula VI compounds for use in any of the various methods of the invention are those compounds shown in Table 1 and Table 1A, wherein the following substitutions are made.

TABLE 1

| Compound[1] | X | R | $R^1$ | $Z^1, Z^{2[2]}$ |
|---|---|---|---|---|
| I-1 | $CO_2CH_3$ | OH | H | H, H |
| I-2 | $CH_2OH$ | OH | H | H, H |
| I-3 | H | OH | H | H, H |
| I-4 | $CONH_2$ | OH | H | H, H |
| I-5 | $CO_2CH_3$ | OH | OH | H, H |
| I-6 | $CH_2OCOCH_3$ | OH | H | H, H |
| I-7[3] | $-CH_2NHCO_2-$ | — | H | H, H |
| I-8 | $CH_2SOCH_3$ | OH | H | H, H |
| I-9 | $CONHC_2H_5$ | OH | H | H, H |
| I-10 | $CONHC_3H_7$ | OH | H | H, H |
| I-11 | CON⟨_O⟩ | OH | H | H, H |
| I-12 | $CONH(CH_2)_2OH$ | OH | H | H, H |
| I-13[3] | $-CH_2OC(CH_3)_2O-$ | — | H | H, H |
| I-14 | $CH=NNHCONH_2$ | OH | H | H, H |
| I-15[3] | $-CH_2N(CH_3)CO_2-$ | — | H | H, H |
| I-16 | $CH_2N(CH_3)_2$ | OH | H | H, H |
| I-17[4,12] | $CH_2NH$-Pro | OH | H | H, H |

TABLE 1-continued

| Compound[1] | X | R | R[1] | $Z^1, Z^{2[2]}$ |
|---|---|---|---|---|
| I-18[4] | CH$_2$NH-Ser | OH | H | H, H |
| I-19 | CH$_2$OH | OCH$_3$ | H | H, H, |
| I-20[5] | CH$_2$S—Glc | OH | H | H, H |
| I-21 | CH$_2$N$_3$ | OH | H | H, H |
| I-22 | CO$_2$CH$_3$ | OH | H | O |
| I-23 | CO$_2$CH$_3$ | OH | Br | H, H |
| I-24 | CH$_2$NHCOCH$_3$ | OH | H | H, H |
| I-25 | CON(CH$_3$)$_2$ | OH | H | H, H |
| I-26 | CONHOH | OH | H | H, H |
| I-27 | CO$_2$CH$_3$ | OH | NHCONHC$_6$H$_5$ | H, H |
| I-28 | CH=NOH | OH | H | H, H |
| I-29 | CH=NNHC(=NH)—NH$_2$ | OH | H | H, H |
| I-30 | 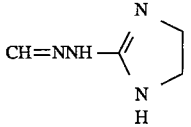 CH=NNH-(imidazole) | OH | H | H, H |
| I-31 | CH$_2$CO$_2$CH$_3$ | OH | H | H, H |
| I-32[4,12] | CH$_2$NH-Gly | OH | H | H, H |
| I-33 | CONHC$_6$H$_5$ | OH | H | H, H |
| I-34 | CO$_2$CH$_3$ | OH | NHCONHC$_2$H$_5$ | H, H |
| I-35 | CO$_2$CH$_3$ | OH | CH$_2$OCONHC$_2$H$_5$ | H, H |
| I-36 | CH$_2$OH | OH | Br | H, H |
| I-37 | CO$_2$CH$_3$ | OH | NHCO$_2$CH$_3$ | H, H |
| I-38 | CO$_2$CH$_3$ | OH | CH$_3$ | H, H |
| I-39[6] | CO$_2$CH$_3$ | OH | Br | H, H |
| I-40 | 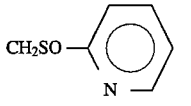 CH$_2$SO-(pyridyl) | OH | H | H, H |
| I-41 | CO$_2$CH$_3$ | OH | CH$_2$OC$_2$H$_5$ | H, H |
| I-42[6] | CH$_2$OH | OH | Br | H, H |
| I-43[6] | CONHCH$_2$CH$_2$OH | OH | Br | H, H |
| I-44[7] | CO$_2$CH$_3$ | OH | Cl | H, H |
| I-45 | CONH$_2$ | OH | Br | H, H |
| I-46 | CH$_2$NHCONHC$_2$H$_5$ | OH | H | H, H |
| I-47 | CH$_2$NHCONHC$_6$H$_5$ | OH | H | H, H |
| I-48 | CH=NN(C$_6$H$_5$)$_2$ | OH | H | H, H |
| I-49 | CH$_2$SC$_6$H$_5$ | OH | H | H, H |
| I-50 | 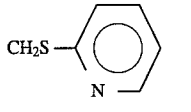 CH$_2$S-(pyridyl) | OH | H | H, H |
| I-51 | CH$_2$SOC$_6$H$_5$ | OH | H | H, H |
| II-1[8] | — | — | H | H, H |
| II-2[9,11] | — | — | H | H, H |
| II-3[10,11] | — | — | H | H, H |

[1] $R^2$ is hydrogen except where noted in footnotes 6, 7, and 8. $R^5$ and $R^6$ are hydrogen.
[2] $Z^1$ and $Z^2$ are both hydrogen, or both are combined together to represent oxygen, where indicated.
[3] X and R are combined together to form the linking group.
[4] NH— amino acid linkage is an amide bond through the carboxyl group of the amino acid.
[5] Glc is glucose; linkage is through the 1-position.
[6] $R^2$ is Br.
[7] $R^2$ is Cl.
[8] $R^3$ and $R^4$ are CH$_2$CH=CH$_2$.
[9] $R^3$ is CH$_2$CH=CH$_2$; $R^4$ is H.
[10] $R^3$ is H; $R^4$ is CH$_2$CH=CH$_2$.
[11] A 1.5 to 1.0 mixture of components II-2 and II-3.
[12] Compound is in the form of the hydrochloride.

TABLE 1A

| Compound[1] | X | R | R[1] |
|---|---|---|---|
| I-52[2] | =O | | H |
| I-53 | CO$_2$CH$_3$ | OCH$_3$ | H |
| I-54 | CONHCH$_3$ | OH | H |

TABLE 1A-continued

| Compound[1] | X | R | R[1] |
|---|---|---|---|
| I-55 | CONH(i-Butyl) | OCOCH$_3$ | H |
| I-56 | CH$_2$SCH$_3$ | OH | H |
| I-57[3] | CH$_2$NH—Lys | OH | H |
| I-58 | CO$_2$CH$_3$ | OH | CH(SC$_6$H$_5$)$_2$ |
| I-59 | CO$_2$CH$_3$ | OH | CH(—SCH$_2$CH$_2$S—) |
| I-60 | CO$_2$CH$_3$ | OH | ![2-(methylthio)pyridine: CH$_2$S—pyridine] |
| I-61 | CO$_2$CH$_3$ | OH | ![CH=NNH-imidazoline] |
| I-62 | CO$_2$CH$_3$ | OH | ![CH$_2$S—pyrimidine] |
| I-63 | CO$_2$CH$_3$ | OH | ![CH$_2$S(O)—pyrimidine] |
| I-64 | CO$_2$CH$_3$ | OH | ![CH$_2$S(O)—pyridine] |
| I-65[4] | CO$_2$CH$_3$ | OH | CH$_2$SC$_2$H$_5$ |
| I-66[5] | CO$_2$CH$_3$ | OH | CH$_2$S(O)C$_2$H$_5$ |
| I-67 | CO$_2$CH$_3$ | OH | ![CH$_2$S—benzimidazole] |
| I-68 | CO$_2$CH$_3$ | OH | ![CH$_2$SCH$_2$—furan] |
| I-69 | CO$_2$CH$_3$ | OH | ![CH=N—N pyrrolidine] |
| I-70 | CO$_2$CH$_3$ | OH | ![CH=N—NH—pyridine] |
| I-71 | CO$_2$CH$_3$ | OH | CH$_2$SCH$_2$CH$_2$N(CH$_3$)$_2$ |
| I-72 | CO$_2$CH$_3$ | OH | ![CH$_2$S—triazole] |
| I-73 | CO$_2$CH$_3$ | OH | CH=NNHC(=NH)NH$_2$ |
| I-74 | CO$_2$CH$_3$ | OH | ![CH=N—N morpholine] |
| I-75 | CO$_2$CH$_3$ | OH | CH=N—N(CH$_3$)$_2$ |

TABLE 1A-continued

| Compound[1] | X | R | R[1] |
|---|---|---|---|
| I-76 | $CO_2CH_3$ | OH |  $CH=N-N\underset{\phantom{x}}{\diagup\kern-0.5em\diagdown}N-CH_3$ |
| II-4[6] | — | — | H |

[1] $Z^1$ AND $Z^2$ are both hydrogen. $R^2$, $R^3$ and $R^4$ are hydrogen except where noted in footnotes 4, 5, 6. $R^5$ and $R^6$ are hydrogen.
[2] X and R are combined together to form the linking group.
[3] NH-amino acid linkage is an amide bond through the carboxyl group of the amino acid.
[4] $R^2$ is $CH_2OH$.
[5] $R^2$ is $CH_2S(O)C_2H_5$.
[6] $R^3$ and $R^4$ are $CH_2CH_2CH_2OH$; $R^2$ is H.

In a related aspect, therefore, the invention features a method of treating a pathological condition of the prostate gland in a mammal. The method involves administering to the mammal a therapeutic amount of an indolocarbazole compound selected from the group consisting of I1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-50, and I-51, I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, and I-76.

In a related aspect, therefore, the invention features a method of treating a pathological condition of the prostrate gland in a mammal. The method involves administering to the mammal a therapeutic amount of an indolocarbazole compound selected from the group consisting of I-52, I-53, I-54, I-55, I-56, I-57, I-58, I-59, I-60, I-61, I-62, I-63, I-64, I-65, I-66, I-67, I-68, I-69, I-70, I-71, I-72, I-73, I-74, I-75, and I-76.

In another embodiment, the indolocarbazole compound is selected from the group consisting of I-6, I-9, I-11, I-13, I-14, I-16, I-17, I-18, I-19, I-24, I-25, I-27, I-31, I-33, I-34, I-35, I-37, I-40, I-41, I-43, I-45, I-46, I-47, I-48, I-49, I-50, and I-51.

In a preferred embodiment, the indolocarbazole compound is I-1, I-5, I-8, I-12, I-15, I-16, I-19, I-20, I-22, or I-42.

In another preferred embodiment, $Z^1$ and $Z^2$ are both hydrogen.

In an additional related aspect, the invention features a method of treating a pathological condition of the prostate gland in a mammal. The method involves administering to the mammal a therapeutic amount of an indolocarbazole compound selected from the group consisting of II-1, II-2, II-3, and II-4.

In any of the various methods of the invention, the indolocarbazole derivative can be administered in combination with a pharmacological excipient, or in the form of a pharmaceutically acceptable salt.

The invention also features compounds represented by the following Formula (III):

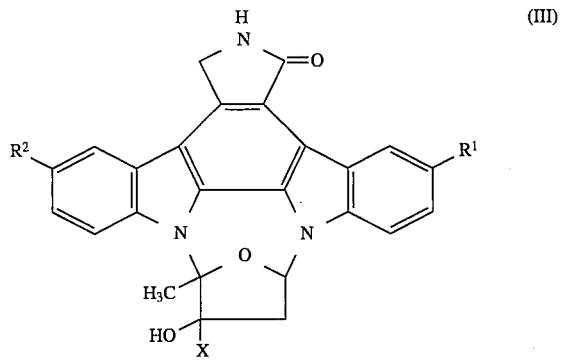

(III)

in which $R^1$ represents halogen, $CH_2OCONHR^{14}$, or $NHCO_2R^{14}$ (in which $R^{14}$ represents lower alkyl); $R^2$ represents hydrogen or halogen; and X represents $CO_2CH_3$, $CH_2OH$, or $CONHR^{15}$ (in which $R^{15}$ represents hydrogen, hydroxy substituted lower alkyl, or aryl), provided that the combination of $R^1$=halogen, $R^2$=hydrogen, and $X=CO_2CH_3$ or $CH_2OH$, and the combination of $R^1=R^2$=halogen and $X=CO_2CH_3$, and the combination of $R^1=R^2$=Br and $X=CONHC_6H_5$, are excluded. Pharmaceutically acceptable salts of Formula III compounds are included in the invention.

The invention also features compounds represented by the following formula (IV):

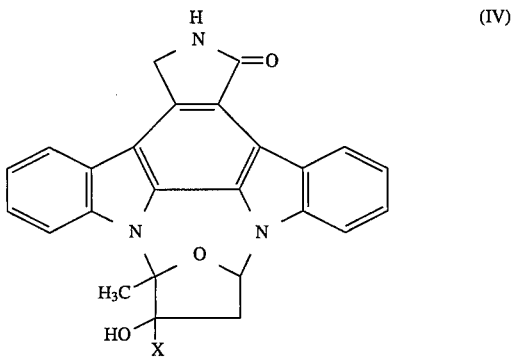

(IV)

in which X represents $CH_2S(O)R^{16}$ (in which $R^{16}$ represents aryl or a heterocyclic group including a nitrogen atom), $CH_2SR^{16}$, $CH=NN(R^{17})_2$ (in which $R^{17}$ represents aryl), $CH_2NHCONHR^{18}$ (in which $R^{18}$ represents lower alkyl or aryl), or $CH_2CO_2CH_3$. Pharmaceutically acceptable salts of Formula IV compounds are included in the invention.

The invention also features compounds represented by the following Formula (V):

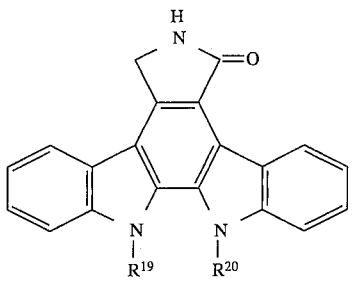

(V)

in which one of $R^{19}$ and $R^{20}$ is hydrogen and the other is allyl, or both of them are allyl, or a pharmaceutically acceptable salt thereof.

The invention also features compounds represented by the following Formula VI:

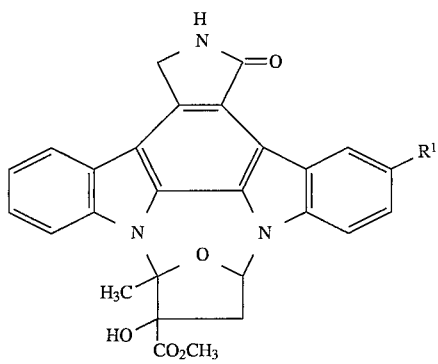

(VI)

in which $R^1$ represents $CH(SC_6H_5)_2$, $CH(-SCH_2CH_2S-)$, $CH_2SR^{24}$ (in which $R^{24}$ represents benzimidazol-2-yl, furfuryl, 2-dimethylaminoethyl, or 1H-1,2,4-triazol-3-yl), or $CH=NR^{25}$ (in which $R^{25}$ represents pyrrolidin-1-yl, pyridin-2-ylamino, guanidino, morpholino, dimethylamino, or 4-methylpiperazin-1-yl), or a pharmaceutically acceptable salt thereof.

In preferred embodiments, the invention features the following novel compositions: Compounds I-35, I-37, I-40, I-42, and I-43. The invention also includes the novel compounds II-1, II-2, and II-3. The invention also includes novel compounds I-58, I-59, I-60, I-61, I-62, I-63, I-64, I-65, I-66, I-67, I-68, I-69, I-70, I-71, I-72, I-73, I-74, I-75, and I-76.

In other preferred embodiments, the pathological condition of the prostate gland in a mammal is benign prostatic hypertrophy or prostate cancer; the activity of trks in the presence of a Compound I or Compound II is less then the activity of trks in the absence of Compound I or Compound II.

In the definitions of the groups in Formula (III) and Formula (IV), lower alkyl means a straight-chain or branched alkyl group having 1 to 6 carbon atoms, such as methyl, ethyl, propyl, isopropyl, butyl, isobutyl, sec-butyl, tert-butyl, pentyl, neopentyl, and hexyl. Aryl means an aryl group having 6 to 10 carbon atoms, such as phenyl and naphthyl. Examples of the heterocyclic group are pyrrolyl, pyranyl, thiopyranyl, pyridyl, thiazolyl, imidazolyl, pyrimidyl, triazinyl, indolyl, quinolyl, purinyl, and benzothiazolyl. Halogen includes fluorine, chlorine, bromine, and iodine.

Preferably the pharmaceutically acceptable salts of Compounds (III), Compounds (IV), Compounds (V), and Compounds (VI) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethylammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Other features and advantages of the invention will be apparent from the following description of the preferred embodiments thereof, and from the claims.

DETAILED DESCRIPTION DRAWING

Figure 1:
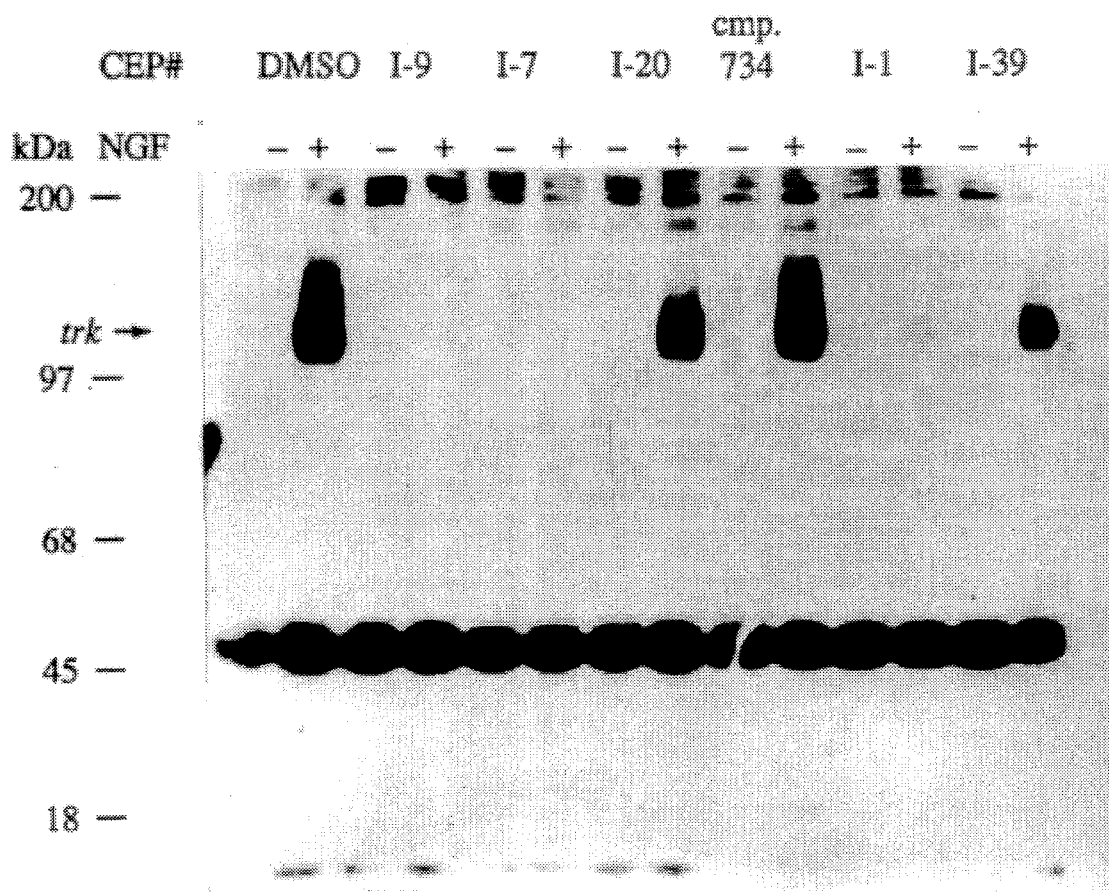
FIG. 1 is an autoradiogram of a Western blot demonstrating inhibition of ligand-dependent trk tyrosine kinase phosphorylation by K-252a derivatives.

Applicants have determined that the ability of a candidate compound to inhibit autophosphorylation of the trks is predictive of its potential for treating a pathological condition of the prostate gland. This is because, as shown herein, pharmacological intervention with trk inhibitors can inhibit specifically the growth of prostate cells in vivo. Proliferating prostate cells are special in this regard because, although trk is present on a large subset of non-prostate proliferating cell types, it is not necessarily the causal force, nor the sustentative force, driving proliferation. Thus, the choice of compounds useful for the treatment of a pathological condition of the prostate gland can be substantially narrowed according to the compound's ability to inhibit trk autophosphorylation.

Compounds that show positive results in the trk autophosphorylation screen are specifically tested for their ability to inhibit the proliferation of prostate cells in both prostate-derived cell lines, and in an appropriate in vivo animal model. The test results disclosed herein show a direct correlation between the ability of a compound to inhibit autophosphorylation in vitro, and its ability to inhibit prostate cell proliferation.

What follows is an analysis of the ability of certain derivatives of the kinase inhibitor K-252a to inhibit pathological prostate cell proliferation based on their ability to inhibit autophosphorylation of trks.

EXAMPLE 1

Selection of Inhibitors of the trks

Candidate compounds for the inhibition of prostate cell proliferation were selected according to their ability to inhibit the tyrosine kinase activity associated with the trks. Upon binding of NGF, trkA undergoes autophosphorylation as a result of the activation of its tyrosine kinase domain (Kaplan et al. *Nature* 350:158– 160, 1991). The degree of autophosphorylation of trks can be measured, and it is recognized as a reliable assay for trk kinase activity (Kaplan, 1991 supra).

PC12 cells (ATCC #CRL1721) are rat pheochromocytoma cells that bear trkA and differentiate into sympathetic neurons when treated with NGF. These cells were grown in 100 mm dishes in DMEM media (GIBCO) containing 7.5% fetal bovine serum, 7.5% horse serum, 2 mM glutamine, 1 mM pyruvate. Cells were incubated at 37° C. in a humidified atmosphere of 10% $CO_2$ and 90% air. Subconfluent cell cultures were incubated in medium without serum for one hour, incubated for one hour with a K-252a derivative compound at a concentration of 100 nM or 500 nM, and then stimulated for 5 minutes with NGF at a concentration of 50 ng/ml. The cells in each culture were disrupted and cell lysates were prepared by standard techniques known to those skilled in the art. Each lysate was incubated with anti-trk antibody whereby immune complexes were formed. Polyclonal anti-trkA, B, and C antibodies were prepared against the C-terminal 16 amino acids of trk (Kaplan et al. 1991 supra). The immune complexes were collected on Protein A-Sepharose beads, separated by SDS-polyacrylamide gel electrophoresis (SDS-PAGE), and transferred to polyvinylidene difluoride (PVDF) membranes (Millipore Corp., Bedford, Mass.), using techniques well known to those skilled in the art. The membranes were incubated with anti-phosphotyrosine antibody, which binds to the tyrosine phosphorylated trks, but not to the un-phosphorylated form of trks. Proteins bound to anti-phosphotyrosine antibody were visualized with enhanced chemiluminescence (ECL, Amersham), and are shown as dark "spots" in FIG. 1.

Measurement of the autophosphorylation of trk provides a good index of trk tyrosine kinase activity, and thereby of trk stimulation. NGF added in the absence of candidate inhibitors resulted in an increase in tyrosine phosphorylation of trk. Referring to FIG. 1, the column headed DMSO(+) (dimethylsulfoxide), the vehicle shows substantial phosphorylation of trkA in the presence of NGF and the absence of a candidate inhibitor compound. When cell cultures were stimulated with NGF in the presence of 100 nM concentrations of compounds I-9, I-7, or I-1, the phosphorylation response was absent (no spot seen). In the presence of 100 nM concentrations of compounds I-20 and I-39, the phosphorylation response was somewhat diminished (a smaller spot was seen). In the presence of a 100 nM concentration of the K-252a derivative, compound 734, there was no effect on autophosphorylation. Derivative compound 734 is included as a non-active, negative control, and demonstrates that the inhibitory activity of other tested derivatives is not attributable to non-specific toxicity.

K-252a compound I-1 and 130 different K-252a derivative compounds were tested as described above for their ability to inhibit the autophosphorylation of the tyrosine kinase domain of trk (concentrations of the derivative compounds were 100 nM and/or 500 nM). Inhibition was indicated by the absence of a spot migrating with the trk marker shown at the left side of the figure. Partial inhibition was indicated by a spot of reduced size. Seventy-three compounds showed at least partial inhibition of phosphorylation at a concentration of 500 nM or less. These compounds, which are tabulated in Table 2, are predicted to be functional K-252a derivatives for the treatment of an abnormal proliferation of cells of the prostate gland.

TABLE 2

| Compound | trk 100 nM | trk 500 nM |
| --- | --- | --- |
| I-1 | + | + |
| I-2 | + | NT |
| I-3 | + | NT |
| I-4 | + | + |
| I-5 | + | NT |
| I-6 | + | NT |
| I-7 | + | NT |
| I-8 | − | + |
| I-9 | + | NT |
| I-10 | + | NT |
| I-11 | + | NT |
| I-12 | + | NT |
| I-13 | + | + |
| I-14 | + | NT |
| I-15 | + | NT |
| I-16 | + | NT |
| I-17 | − | + |
| I-18 | + | NT |
| I-19 | + | NT |
| I-20 | − | + |
| I-21 | − | + |
| I-22 | + | NT |
| I-23 | − | + |
| I-24 | + | NT |
| I-25 | + | NT |
| I-26 | + | NT |
| I-27 | − | + |
| I-28 | + | NT |
| I-29 | − | + |
| I-30 | − | + |
| I-31 | + | NT |
| I-32 | + | NT |
| I-33 | − | + |
| I-34 | − | + |
| I-35 | + | + |
| I-36 | + | NT |
| I-37 | + | NT |
| I-38 | + | NT |
| I-39 | + | NT |
| I-40 | + | NT |
| I-41 | + | + |
| I-42 | + | + |
| I-43 | − | + |
| I-44 | − | + |
| I-52 | + | NT |
| I-53 | + | NT |
| I-54 | + | NT |
| I-55 | + | NT |
| I-56 | NT | + |
| I-57 | + | NT |
| I-58 | − | + |
| I-59 | − | + |
| I-60 | − | + |
| I-61 | − | + |
| I-62 | + | + |
| I-63 | − | + |
| I-64 | − | + |
| I-65 | − | + |
| I-66 | − | + |
| I-67 | + | + |
| I-68 | − | + |
| I-69 | + | + |
| I-70 | + | + |
| I-71 | − | + |
| I-72 | − | + |
| I-73 | + | + |
| I-74 | + | + |
| I-75 | NT | + |
| I-76 | NT | + |
| II-1 | − | + |
| II-2 | − | + |

TABLE 2-continued

| Compound | trk 100 nM | trk 500 nM |
|---|---|---|
| II-4 | NT | + |

NT: Not Tested
(+): Inhibited phosphorylation;
(−): Did not inhibit phosphorylation

EXAMPLE 2

Growth Inhibition of Cancerous Human Prostate Cells in Culture

Functional derivatives of K-252a were tested for their ability to inhibit the growth, in culture, of the androgen independent human prostate cancer cell lines Tsu-Pr1 (Iizumi, et al., J. Urol. 137: 1304–1306, 1987), DuPro-1 (Gingrich, et al., J. Urol. 146: 915–919, 1991), PC-3 (ATCC #CRL1435) and DU-145 (ATCC #HTB81). Throughout the experiment the Tsu-Pr1 and Du-Pro1 cells were maintained in RPMI 1640 medium (GIBCO) containing 10% fetal bovine serum (Hyclone), 2 mM glutamine, 100 U/ml penicillin, and 100 μg/ml streptomycin. The PC-3 cells were maintained in Ham's F12K medium (Irvine Scientific) containing 10% fetal bovine serum (Hyclone), 2 mM glutamine, 100 U/ml penicillin, and 100 μg/ml streptomycin. All cell lines were maintained at 37° C. in a humidified atmosphere containing 5% $CO_2$. The DU-145 cells were maintained in minimal essential medium (Gibco), containing 10% fetal bovine serum (Hyclone), 2 mM glutamine, and no antibiotics.

Tests for growth inhibition by the candidate compounds were conducted by the following procedure. In each well of a 96-well plate (Falcon) were placed 2,500 cells in 0.1 ml of medium. The cultures were incubated overnight after which a 0.1 ml aliquot of culture medium was added to each well. Each aliquot contained a different concentration of ten representative candidate compounds (I-1, I-5, I-8, I-12, I-15, I-16, I-19, I-20, I-22, and I-42). Two additional aliquots contained the K-252a derivatives cmp700 or cmp783, which were found not to inhibit autophosphorylation of the tyrosine kinase domain of trk in the test described in Example 1. The derivatives cmp700 and cmp783 were therefore included as negative controls to show that the inhibition of cancer derived prostate cell growth is correlated with the inhibition of autophosphorylation of the tyrosine kinase domain of the trks. Other control wells received medium without any K-252a derivative compounds. Incubation was continued for three days. On day three the number of cells in each well was measured using a calcein fluorescence assay (Bozyczko-Coyne et al. J. Neurosci. Meth. 50, 205–216 (1993)).

Calcein AM (Molecular Probes, Eugene, Oreg.), an analog of the viable dye fluorescein diacetate, is taken up by cells and cleaved intracellularly to fluorescent salts that are retained by intact membranes of viable cells. This method thus provides a reliable and quantitative measurement of cell survival. Calcein AM was diluted 2× in Dulbeccos phosphate buffered saline (D-PBS) to 2× the final assay concentration (6 μM) and 100 μl was added to culture wells containing 100 μl of medium. The plates were then incubated for 1 hour at 37° C. Cells were then washed 4 times with D-PBS to remove excess calcein not taken up by cells. The plate was read using a Millipore plate reading fluorimeter (Cytofluor 2350) at emission=485 nm and excitation=538 nm. After subtraction of blank values (wells containing medium but no cells), relative fluorescent values reflect a quantitative measurement of cell survival.

The number of cells in the wells containing functional derivatives was compared to the number of cells in the control wells. The concentration which inhibited cell growth by 50% was calculated and is referred to as the "$IC_{50}$". The results are shown in Table 3.

TABLE 3

| Compound | Tsu-Pr1 $IC_{50}$ (μM) | Du-Pro1 $IC_{50}$ (μM) | PC-3 $IC_{50}$ (μM) | DU-145 $C_{50}$ (μM) |
|---|---|---|---|---|
| I-12 | 0.038 | 0.31 | 0.69 | 0.75 |
| I-5 | 0.07 | 0.06 | NT | 0.08 |
| I-19 | 0.07 | 0.27 | 5.0 | 0.11 |
| I-42 | 0.09 | NT | NT | NT |
| I-1 | 0.21 | 0.75 | 3.4 | 1.2 |
| I-16 | 0.21 | NT | NT | NT |
| I-15 | 0.51 | NT | NT | NT |
| I-8 | 0.54 | NT | NT | NT |
| I-22 | 0.69 | NT | NT | NT |
| I-20 | 5.7 | NT | NT | NT |
| cmp 700* | 2.7 | >5 | 7.6 | 3.1 |
| cmp 783* | 1.1 | 3.1 | 11 | 1.7 |

NT = not tested
*Non-inhibitors of trk included as controls

All compounds listed in Table 3 inhibited cell growth in one or more prostate cancer-derived cell lines. The general pattern of inhibition was the same across all cell lines (Table 3), although the actual $IC_{50}$ concentration for each compound varied among the cell lines tested. For example, I-12, I-5, and I-19 were the most potent compounds in inhibiting growth in all four cell lines although with different potency. In contrast, compounds 700 and 783, which do not inhibit trks, were clearly less potent inhibitors of prostate cell line growth. Growth of the PC-3 cell line appeared to be the least affected by inhibitors of trks. The number, type and/or distribution of trks may be different in PC-3 cells compared to the other cell lines used. The data presented in Table 3 support the conclusion that compounds that inhibit the autophosphorylation of trks inhibit the growth of androgen-independent human prostate cancer cells.

EXAMPLE 3

Inhibition of prostate growth in sexually immature mice

The following animal model can be used to test the efficacy of a functional derivative for treatment of a proliferative prostate condition. Sexually immature male mice of 15–20 g each (Charles River Laboratories, Raleigh, N.C.) were used in the following in vivo study. The mice were allowed at least 3 days after purchase to acclimate before being used in any experiments.

Solutions of compounds I-1, I-12, and cmp700 were prepared daily by dissolving them in 10% Tween 20, 5% ethanol, and 85% phosphate buffered saline (TEPBS). Each test group contained 12 mice. Mice were injected subcutaneously each day for 21 days with TEPBS, TEPBS containing compound I-1 at concentrations of 1 or 10 mg/kg, TEPBS containing compound 1-12 at concentrations of 1 or 10 mg/kg, or TEPBS containing cmp700 at concentrations of 1 or 10 mg/kg. At the end of the 21 day dosing period the mice were sacrificed and whole body blood, dorsal prostate, ventral prostate, coagulating glands, seminal vesicles, heart, liver, stomach, lung, kidneys and testes were collected separately and weighed.

The concentration of plasma testosterone was determined using the Coat-A-Count Total Testosterone RIA kit (Diagnostic Products Corporation, Los Angeles, Calif. 90045).

This was done to show that the compounds prevent epithelial growth through a mechanism that does not involve modulation of serum testosterone levels.

The average weight of each tissue is shown in Tables 4, 5, 6, and 7. The results from mice receiving injections of TEPBS with compound I-1, TEPBS with compound I-12, or TEPBS with cmp700 were compared to those from mice receiving TEPBS alone using a Dunnett's T-test or a group t-test (Tables 4 and 5). The results from mice receiving injections of TEPBS with compound I-19 were compared to those from mice receiving TEPBS alone using a Dunnett's T-test, a Newman-Keul test, or a group t-test (Tables 6 and 7) (Tallarida et al. *Manual of Pharmacologie Calculation with Computer Programs.* 2nd ed. Springer Verlag, New York, 1987, pp. 121–125, 131–134, 145–148).

TABLE 4

EFFECT OF COMPOUNDS I-1, I-12 AND Cmp 700** ON BODY WEIGHTS AND THE WEIGHT OF PROSTATE GLANDS

| Treatment | Body Weight (g) | Ventral Prostate (mg) | Dorsal Prostate (mg) | Seminal Vesicles (mg) | Coagulating Glands (mg) |
|---|---|---|---|---|---|
| TEPBS | 31.5 ± 0.8 | 11.3 ± 0.6 | 9.8 ± 1.6 | 75.0 ± 5.0 | 25.1 ± 1.6 |
| I-1-1 mg/kg | 32.2 ± 0.6 | 7.6 ± 0.9*a | 6.2 ± 1.3 | 61.4 ± 4.1a | 18.2 ± 2.4a |
| I-1-10 mg/kg | 30.0 ± 0.6 | 8.6 ± 0.8a | 6.7 ± 0.7 | 66.4 ± 5.6 | 18.5 ± 1.4a |
| Cmp 700-1 mg/kg** | 30.3 ± 0.7 | 11.1 ± 0.8 | 11.2 ± 1.2 | 57.9 ± 3.9*a | 23.4 ± 2.4 |
| Cmp 700-10 mg/kg** | 30.2 ± 0.7 | 11.0 ± 0.6 | 9.6 ± 1.2 | 88.1 ± 4.9 | 19.4 ± 2.9 |
| I-12-1 mg/kg | 32.8 ± 0.4 | 6.2 ± 0.4*a | 4.7 ± 0.4*a | 54.3 ± 1.5*a | 18.0 ± 2.4a |
| I-12-10 mg/kg | 29.5 ± 1.0 | 8.4 ± 0.8*a | 8.6 ± 1.1 | 55.3 ± 2.2*a | 17.6 ± 1.0a |

*Significantly different from values of TEPBS according to Dunnett's t test $p < 0.05$.
aSignificantly different from values of TEPBS according to group t-test $p < 0.05$
**non-inhibitors of trk included as controls

TABLE 5

EFFECT OF COMPOUND I-1, Cmp 700**, AND COMPOUND I-12 ON THE WEIGHT OF PERIPHERAL ORGANS

| Treatment | Stomach (mg) | Heart (mg) | Lung (mg) | Testes (mg) | Kidney (mg) | Liver (mg) |
|---|---|---|---|---|---|---|
| TEPBS | 294 ± 22 | 171 ± 8.4 | 230 ± 15.9 | 202 ± 6 | 576 ± 22 | 1937 ± 75 |
| I-1 1 mg/kg | 288 ± 10 | 164 ± 6.4 | 229 ± 8.02 | 216 ± 6 | 598 ± 19 | 1921 ± 81 |
| I-1 10 mg/kg | 295 ± 30 | 152 ± 6.58 | 263 ± 14.8 | 204 ± 11 | 550 ± 18 | 1765 ± 50 |
| Cmp 700** 1 mg/kg | 277 ± 17 | 167 ± 7.06 | 280 ± 17.9 | 205 ± 8 | 561 ± 25 | 2011 ± 88 |
| Cmp 700** 10 mg/kg | 341 ± 25 | 164 ± 7.28 | 312 ± 18.4*a | 218 ± 13 | 596 ± 21 | 2072 ± 106 |
| I-12 1 mg/kg | 329 ± 28 | 179 ± 8.78 | 244 ± 15.1 | 191 ± 12 | 591 ± 16 | 2120 ± 54 |
| I-12 10 mg/kg | 270 ± 19 | 152 ± 9.60 | 253 ± 20.9 | 187 ± 5 | 552 ± 29 | 1886 ± 84 |

*Significantly different from vehicle according to Dunnett's t-test $p < 0.05$
aSignificantly different from vehicle according to group t-test $p < 0.05$.
**non-inhibitors of trk included as controls

TABLE 6

EFFECT OF COMPOUND I-19 ON BODY WEIGHTS AND THE WEIGHTS OF PROSTATE GLANDS

| Treatment | Body Weight (g) | Ventral Prostate (mg) | Dorsal Prostate (mg) | Seminal Vesicles (mg) | Coagulating Glands (mg) |
|---|---|---|---|---|---|
| TEPBS | 32.0 ± 0.6 | 14.0 ± 0.8 | 14.6 ± 1.4 | 71.4 ± 2.4 | 29.6 ± 2.0 |
| I-19 1 mg/kg | 31.9 ± 0.8 | 11.0 ± 0.9*a | 10.4 ± 0.9*a | 60.0 ± 2.2*a | 24.6 ± 1.4a |
| I-19 10 mg/kg | 31.2 ± 0.5 | 10.5 ± 0.6*a | 7.2 ± 0.8*ab | 52.0 ± 2.0*a | 23.6 ± 0.8a |

*Significantly different from vehicle according to Dunnett's t test $p < 0.05$
aSignificantly different from vehicle according to group t-test $p < 0.05$.
bSignificantly different from 1 mg/kg of I-19 according to Newman-Keul test $p < 0.05$

TABLE 7

EFFECT OF COMPOUND I-19 ON THE WEIGHT OF PERIPHERAL ORGANS

| Treatment | Stomach (mg) | Heart (mg) | Lung (mg) | Testes (mg) | Kidney (mg) | Liver (mg) |
|---|---|---|---|---|---|---|
| TEPBS | 272 ± 14 | 170 ± 10 | 280 ± 15 | 206 ± 8 | 589 ± 34 | 2004 ± 69 |
| I-19 1 mg/kg | 252 ± 12 | 160 ± 20 | 323 ± 16 | 205 ± 7 | 467 ± 18 | 1968 ± 58 |
| I-19 10 mg/kg | 242 ± 11 | 166 ± 8 | 276 ± 18 | 208 ± 8 | 563 ± 17 | 1933 ± 70 |

None of the tested compounds significantly reduced the body weight or the weight of stomachs, hearts, lungs, testes, kidneys or livers (Tables 5 and 7). In contrast (as shown in Tables 4 and 6), compound I-1 at a dose of 1 mg/kg significantly reduced the weight of the ventral prostates and seminal vesicles. The higher dose of compound I-1 did not produce any greater effect. Compound I-12 at doses of 1 mg/kg and 10 mg/kg reduced the weight of the ventral prostates and seminal vesicles. The weight of the dorsal prostate was only reduced after treatment with 1 mg/kg of compound 1-12. Compound I-19 at concentrations of 1 mg/kg and 10 mg/kg significantly reduced the weights of ventral prostate, dorsal prostate, seminal vesicles, and coagulating glands. Cmp700, the derivative which failed to inhibit the tyrosine kinase activity of trk, did not inhibit prostate tissue growth but did cause the reduction of seminal vesicle weight at a dose of 1 mg/kg but not at 10 mg/kg.

There was no significant difference in the concentration of plasma testosterone between any of the groups. Thus, reduction in the weight of ventral prostates, dorsal prostates, or seminal vesicles was not due to a reduced amount of circulating testosterone.

EXAMPLE 4

Inhibition of Prostate Cancer with Functional Derivatives

In addition to the methods provided in Example 3 above, the usefulness of the K-252a derivatives provided herein specifically for the treatment of prostate cancer can be assessed in several animal models. Two of these models include 1) a test of the effect of a functional derivative on the growth of human prostate cancer cell lines in nude mice; and 2) a test of the effect of a functional derivative on the growth of Dunning prostate tumors in rats.

To test compounds in nude mice, a human prostate cell line, e.g., the Tsu-Pr1, DuPro-1, PC-3, or DU-145 cell lines described in Example 2, can be grown under standard conditions and injected (at $1 \times 10^6$ cells/0.1 ml–$10^7$ cells/1 ml) subcutaneously into the rear haunch of adult athymic nude mice (Gleave, et al. *Cancer Res.* 51:3753–3761, 1991). The effect of test compounds on the growth of the tumor will be assessed by measuring the size and growth rate of the tumor in the presence and absence of the test compound.

The Dunning rat prostate tumor lines are transplantable rat tumors which have become standard models for assessment of potential cancer treatments. One method of using the Dunning tumors to assess the effects of potential anticancer compounds has been described in detail (Isaacs, *Cancer Res.* 49:6290–6294, 1989). The utility of the K-252a derivatives provided herein for reducing tumors in this model involves measuring the effect of test compounds on the growth rate of the tumor. Test compounds are dissolved and injected as described above.

EXAMPLE 5

Efficacy of trk Antagonists in Animal Models of Prostate Cancer

The efficacy of trk antagonists in inhibiting the growth of androgen-independent prostate cancer cells in vitro indicated that the molecules would be efficacious in in vivo models of androgen-independent prostate cancer. We chose to examine the effects of Compounds I-19 and I-5 on the growth of the androgen-independent Dunning R-3327 AT-2 rat prostate cancer tumor in vivo. The AT-2 tumor is a highly anaplastic cell line derived from the original slow-growing androgen-dependent Dunning R-3327 H rat prostate tumor (Issacs et al., *Prostate* 9:261–281, 1986). The AT-2 tumor model has been used to characterize other potential anti-prostatic cancer agents including linomide (Ichikawa et al., *Cancer Research* 52:3022–3028, 1992) and suramin (Morton et al., *Prostate* 17:327–336, 1990) which is undergoing evaluation in clinical trials for androgen-independent prostate cancer (Eisenberger et al., *J. Natl. Can. Inst.* 85: 611–621, 1993).

Experimental Protocol: Twenty-four inbred male Copenhagen rats were inoculated subcutaneously in the flank with $1 \times 10^6$ viable AT-2.1 tumor cells. All animals were allowed to develop tumors of approximately 2.7 cm$^3$ in size (approximately 14 days) before being randomized into three groups of 8 animals each. Group 1 received daily subcutaneous injections of vehicle alone (1 ml/kg body weight). Group 2 received daily subcutaneous injections of Compound I-19 (1 ml/kg of a solution containing I-19 at 10 mg/ml). Group 3 received daily subcutaneous injections of Compound I-5 (1 ml/kg of a solution containing I-5 at 3 mg/ml). All animals had their tumor sizes evaluated for a period of 16 days. Tumor volume was calculated using the formula $(1 \times w^2) \times 0.5$.

Results: The results of the experiment are presented in Table 8. Both Compound I-19 (10 mg/kg/day) and Compound I-5 (3 mg/kg/day) were effective in inhibiting growth of AT-2.1 tumors by approximately 50–60%. These results demonstrate the utility of these compounds in inhibiting the growth of prostate cancer cells in vivo.

TABLE 8

Efficacy of Compounds I-19 and I-5 in
Inhibiting the Growth of Dunning R-3327
AT-2.1 Prostate Tumor in Adult Male Copenhagen Rats

| Treatment group | Tumor volume (cm³) at indicated days of treatment | | | | |
|---|---|---|---|---|---|
| | Day 0 | Day 3 | Day 8 | Day 13 | Day 16 |
| Vehicle only (control) | 2.73 ± 0.50 | 6.66 ± 1.48 | 21.0 ± 3.0 | 37.3 ± 4.0 | 58.7 ± 5.0 |
| I-19 10 mg/kg/day | 2.62 ± 0.53 | 5.52 ± 1.10 | 11.3 ± 1.8 | 22.4 ± 2.7 | 28.4 ± 5.1 |
| I-5 3 mg/kg/day | 2.70 ± 1.06 | 5.64 ± 1.32 | 10.7 ± 2.9 | 19.8 ± 5.6 | 24.6 ± 6.2 |

Synthesis of Compounds

The processes for producing Compounds (III), Compounds (IV), Compounds (V), and Compounds (VI) are described below.

EXAMPLE 6

Compound I-45

Figure 2:
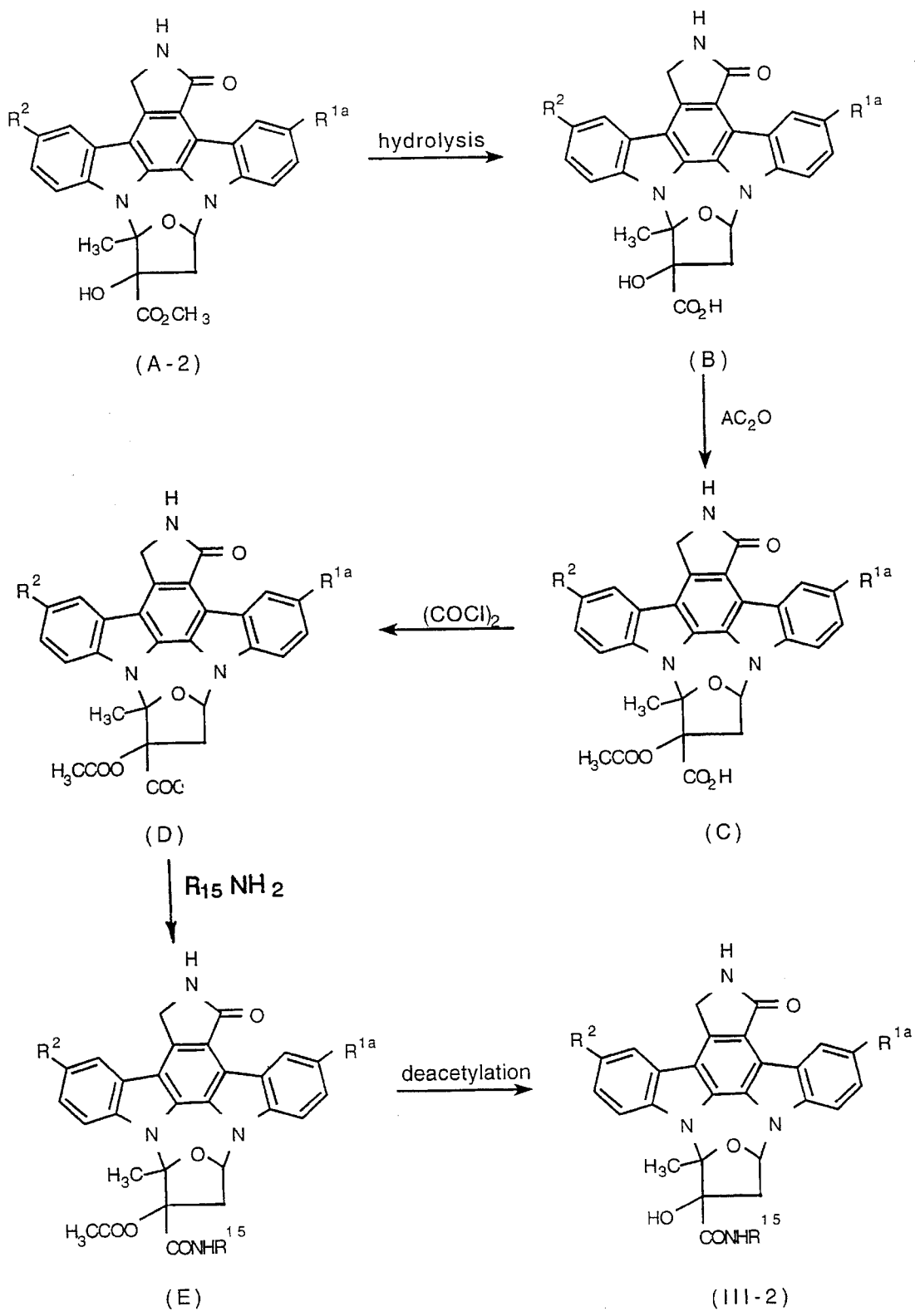
FIG. 2 is a schematic illustration of the synthesis of Compound III-2.

Compound (A-2-1; FIG. 2; $R^{1a}$=Br, $R^2$=H) (250 mg, 0.46 mmol) was dissolved in 1 ml of dimethylformamide, and then 0.25 ml of an aqueous solution of 23.5 mg of sodium hydroxide was added thereto, followed by stirring at room temperature for 4 hours. After 1N hydrochloric acid was added to adjust the pH of the solution to 1–2, the precipitates were collected by filtration to give 223 mg (yield 91%) of Compound (B-1; $R^{1a}$=Br, $R^2$=H).

$^1$H-NMR (DMSO-$d_6$) δ (ppm): 2.00(1H, dd, J=5.1, 14.0 Hz), 2.22(3H, s), 5.01(2H, s), 7.10(1H, dd, J-5.7, 7.0 Hz), 7.26–8.08(6H, m), 8.65(1H, s), 9.36(1H, d, J-2 Hz)

Compound (B-1; $R^{1a}$=Br, $R^2$=H) (210 mg, 0.39 mmol) was dissolved in 3 ml of pyridine, and then 0.44 ml (4.7 mmol) of acetic anhydride was added thereto, followed by stirring at room temperature for 4 days. After evaporation of the solvent, 4 ml of 1N hydrochloric acid was added to the residue, and the precipitates were collected by filtration to give 223 mg (yield 99%) of Compound (C-1; $R^{1a}$=Br, $R^2$=H)

$^1$H-NMR (DMSO-$d_6$) δ (ppm): 1.66 (3H, s ), 2.48 (3H, s), 5.02(2H, s), 7.16–8.08(7H, m), 8.69(1H, s), 9.34 (1H, d, J=2 Hz)

Compound (C-1; $R^{1a}$=Br, $R^2$=H) (100 mg, 0.17 mmol) was suspended in 3 ml of thionyl chloride, followed by stirring at 90° C. for 4.5 hours. After evaporation of the solvent, diethyl ether was added to the residue, and the precipitates were collected by filtration to give 84 mg (yield 83%) of Compound (D-1; $R^{1a}$=Br, $R^2$=H).

Compound (D-1; $R^{1a}$=Br, $R^2$=H) (84 mg, 0.39 mmol) was dissolved in 2 ml of ethylene dichloride, and then 3 ml of 0.8% $NH_3$/ tetrahydrofuran was added thereto under ice cooling, followed by stirring at the same temperature for 1 hour. After evaporation of the solvent, the residue was dissolved in a mixture of 2 ml of tetrahydrofuran and 0.5 ml of methanol, and then 1 ml of 1N NaOH was added thereto, followed by stirring at room temperature for 3 hours. To the solution was added 1N hydrochloric acid (1.2 ml) for neutralization, followed by dilution with tetrahydrofuran. The mixture was washed with a saline solution and dried over sodium sulfate. After evaporation of the solvent, the residue was subjected to silica gel column chromatography (chloroform/methanol=98/2) to give 54 mg (yield 72%) of Compound I-45.

$^1$H-NMR (DMSO-$d_6$) δ (ppm): 2.018 (1H, dd, J=4.6, 13.7 Hz), 2.183(3H, s), 4.985(1H, d, J=17.0 Hz), 5.054(1H, d, J=17.1 Hz), 6.308(1H, s), 7.057(1H, dd, J=4.9, 7.5 Hz), 7.353–8.092(8H, m), 8.696(1H, s), 9.385(1H, d, J=2.1 Hz) SIMS (m/z): 531 (M+1)$^+$

EXAMPLE 7

Compound I-35

Figure 3:
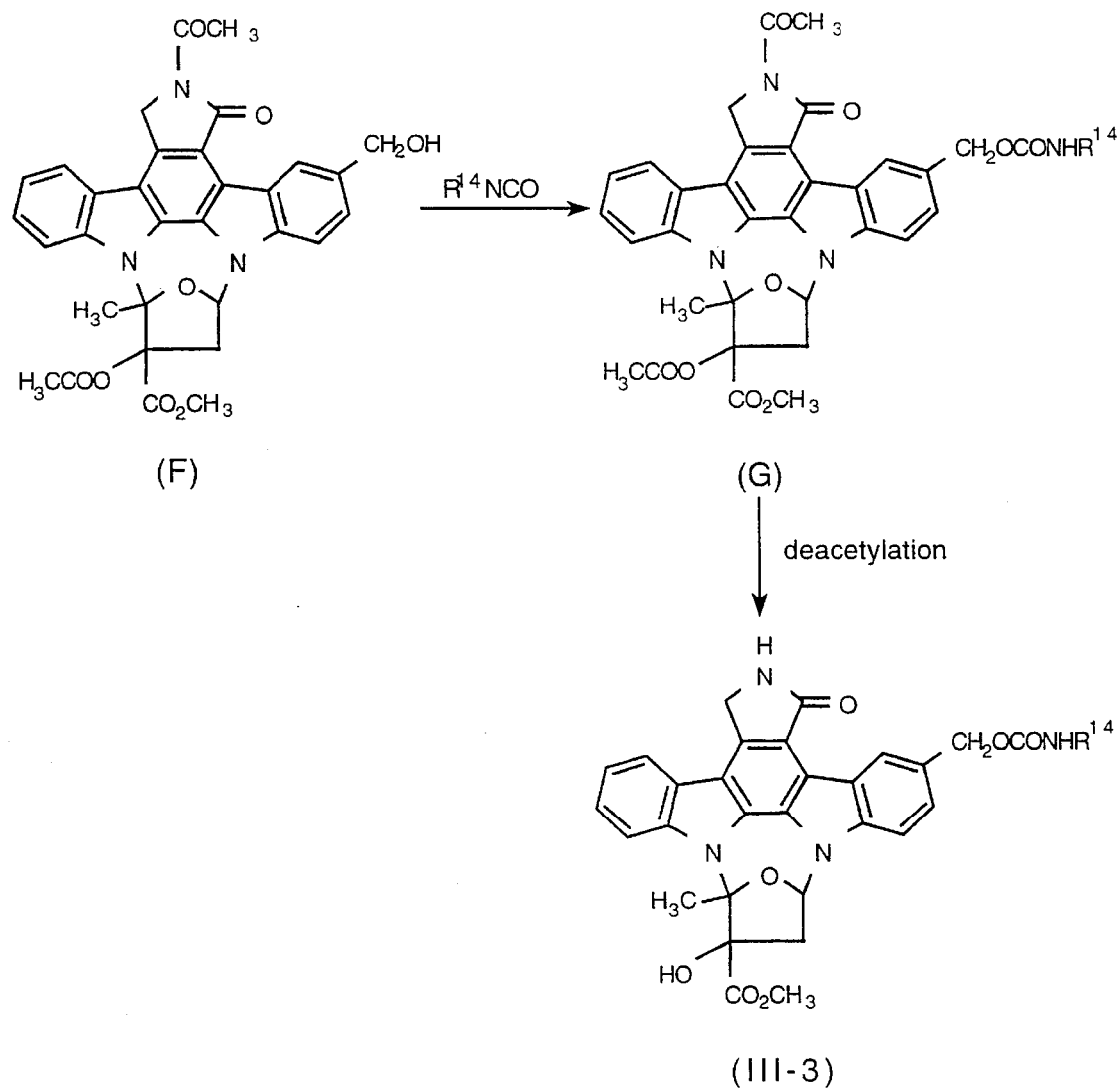
FIG. 3 is a schematic illustration of the synthesis of Compound III-3.

Compound (F; FIG. 3) (70 mg, 0.12 mmol) was dissolved in a mixture of 3 ml of tetrahydrofuran and 1 ml of dimethylformamide, and then 34 μl (0.24 mmol) of triethylamine and 19 μl (0.24 mmol) of ethyl isocyanate were added thereto, followed by stirring at 50° C. for 6 hours. After dilution with chloroform, the mixture was washed successively with water and a saline solution, and dried over sodium sulfate. After evaporation of the solvent, the residue was subjected to silica gel column chromatography (chloroform/methanol=99/1) to give 71 mg (yield 91%) of Compound (G).

$^1$H-NMR (CDCl$_3$) δ (ppm): 1.16(3H, t, J-7.3 Hz), 1.800(3H, s), 2.150(1H, dd, J-5.1, 14.5 Hz), 2.282(3H, s), 2.849(3H, s), 3.273(1H, m), 3.978(1H, dd, J=7.5, 14.5 Hz), 4.011(3H, s), 5.355(2H, brs), 5.406(1H, d, J=17.4 Hz), 5.449(1H, d, J=17.4 Hz), 7.007(1H, dd, J=5.1, 7.4 Hz), 7.427–8.098(6H, m), 9.245(1H, s) FAB-MS (m/z): 652 (M)$^+$ Compound (G) (44 mg, 0.067 mmol) was dissolved in a mixture of 1 ml of ethylene dichloride and 0.5 ml of methanol, and then 13 μl of 28% sodium methoxide/methanol was added thereto, followed by stirring at room temperature for 20 minutes. Amberlist 15 was added to the mixture for neutralization and insoluble matters were filtered off. After evaporation of the solvent, the residue was subjected to preparative TLC (chloroform/methanol=95/5) to give 68.9 mg (yield 24%) of Compound I-35.

$^1$H-NMR (CDCl$_3$) δ (ppm): 1.103(3H, t, J=7.2 Hz), 2.163(3H, s), 2.282(1H, dd, J=5.0, 14.3 Hz), 3.184(2H, q, J=7.2 Hz), 3.288(1H, dd, J=7.5, 14.3 Hz), 4.023(3H, s), 4.866(1H, d, J=17.0 Hz), 4.937 (1H, d, J=16.9 Hz), 5.230(2H, s), 6.856(1H, dd, J=5.0, 7.5 Hz), 7.306–7.882(6H, m), 9.148(1H, s) FAB-MS (m/z) :569 (M+1)$^+$

EXAMPLE 8

Compound I-37

Figure 4:
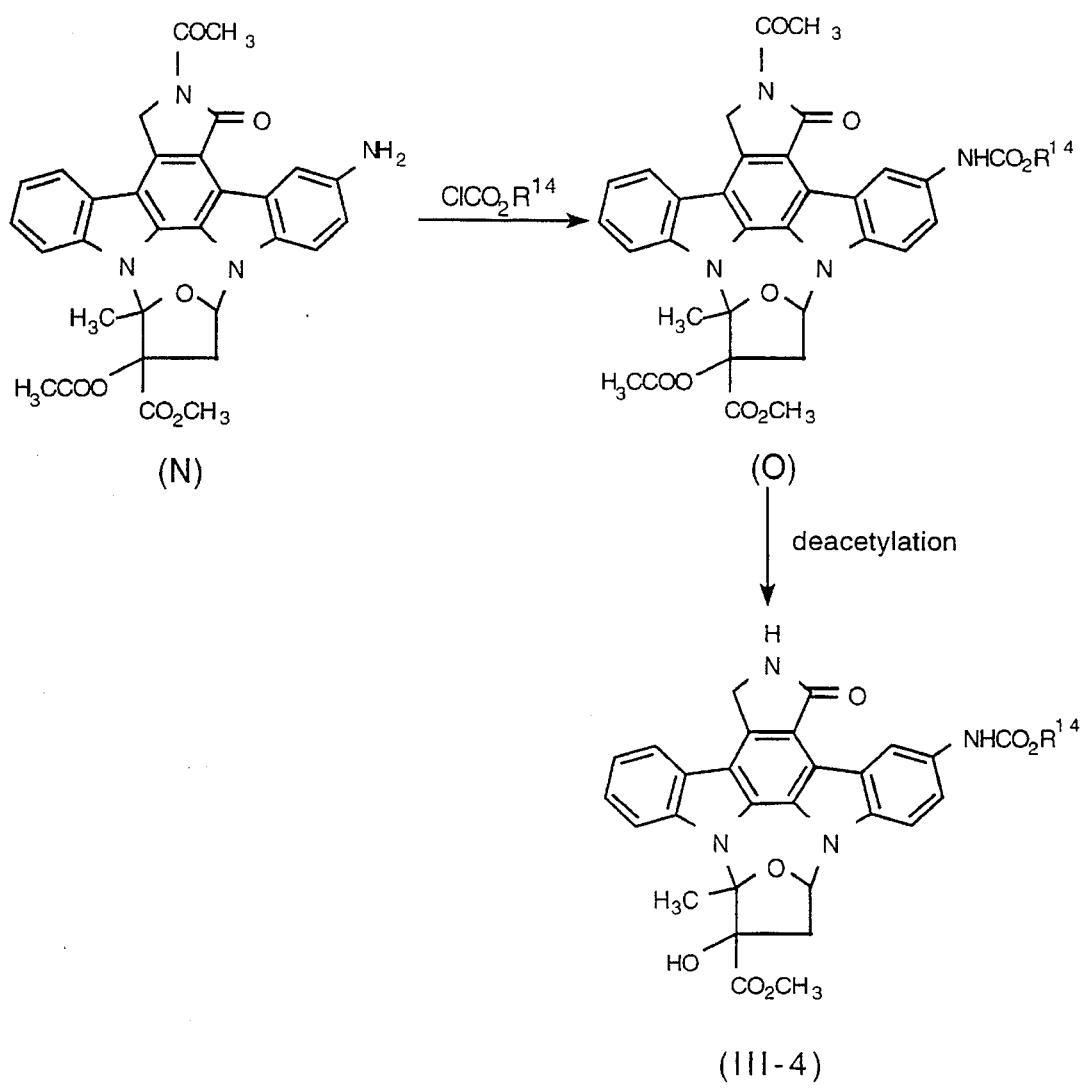
FIG. 4 is a schematic illustration of the synthesis of Compound III-4.

Compound (N; FIG. 4) (98 mg, 0.17 mmol) was dissolved in 5 ml of ethylene dichloride, and then 39 μl of methyl chloroformate and 71 μl of triethylamine were added thereto, followed by stirring at room temperature for 1.5 hours. Methanol (1 ml) was added to the solution and the solvent was evaporated. The residue was subjected to preparative TLC (chloroform/methanol=98/2) and the crude product obtained was recrystallized from ethyl acetate to give 18 mg (yield 17%) of Compound (O-1; $R^{14}$=$CH_3$).

$^1$H-NMR (CDCl$_3$) δ (ppm): 1.783(3H, s), 2.125(1H, dd, J=5.0, 14.6 Hz), 2.269(3H, s), 2.810(3H, s), 3.828 (3H, s), 3.965(1H, dd, J=7.4, 14.6 Hz), 4.007(3H, s), 5.357(1H, d, J=17.8 Hz), 5.403(1H, d, J=17.6 Hz), 6.963(1H, dd, J=4.9, 7.6 Hz), 7.411–8.071(6H, m), 8.944(1H, d, J=2.0 Hz)

Substantially the same procedure as in example 7 was repeated using 8 mg (0.013 mmol) of Compound (O-1; $R^{14}$=$CH_3$) obtained above to give 5 mg (yield 71%) of Compound I-37.

$^1$H-NMR (DMSO-d$_6$) δ (ppm): 1.999(1H, dd, J=4.6, 13.9 Hz), 2.146(3H, s), 3.373(1H, dd, J=7.7, 14.2 Hz), 3.688 (3H, s), 3.924(3H, s), 4.959(1H, d, J=17.6 Hz), 5.020(1H, d, J=17.6 Hz), 6.311(1H, s), 7.081(1H, dd, J=5.0,7.0 Hz), 7.333–8.052(6H, m), 8.553 (1H, s) FAB-MS (m/z): 541 (M+1)$^+$

EXAMPLE 9

Compound I-42

Compound (A-1-1, Process 1; $R^{1a}$=$R^{2a}$=Br) (62.5 mg, 0.1 mmol) was dissolved in a mixture of 3 ml of tetrahydrofuran and 1 ml of methanol, and then 19 mg (0.5 mmol) of sodium borohydride was added thereto, followed by stirring at room temperature for 12 hours. After being adjusted to pH 1–2 with 1N hydrochloric acid, the mixture was washed with a saline solution and dried over sodium sulfate. After evaporation of the solvent, the residue was subjected to preparative TLC (chloroform/methanol=95/5) to give 37 mg (yield 62%) of Compound I-42.

$^1$H-NMR (DMSO-d$_6$) δ (ppm): 1.918(1H, dd, J=4.9, 5.1 Hz), 2.140(3H, s), 3.149(1H, dd, J+7.3, 7.6 Hz), 3.728–3.836(2H, m), 5.009(1H, d, J=17.8 Hz), 5.070(1H, d, J=17.5 Hz), 5.144(1H, t, J=5.1 Hz), 5.439(1H, s), 6.994(1H, dd, J=4.9, 7.5 Hz), 7.573–8.184(5H, m), 8.701(1H, s), 9.387(1H, d, J=2.2 Hz) FAB-MS (m/z): 598 (M+1)$^+$

EXAMPLE 10

Compound I-43

Substantially the same amidation procedure as in example 6 was repeated using 67 mg (0.1 mmol) of Compound (D-2; $R^{1a}$=$R^2$=Br) and 120 μl of ethanolamine and then substantially the same deacetylation procedure as in example 7 was repeated to give 30 mg of Compound I-43.

$^1$H-NMR (DMSO-d$_6$) δ (ppm): 2.009 (1H, dd, J=4.7, 13.9 Hz), 2.102(3H, s), 4.832(1H, t, J=5.5 Hz), 5.004(1H, d, J=17.3 Hz), 5.073(1H, d, J=17.3 Hz), 6.509(1H, s), 7.055(1H, dd, J=4.7, 7.3 Hz), 7.586–8.270(6H, m), 8.695(1H, s), 9.380(1H, d, J=2.2 Hz) FAB-MS (m/z): 655 (M+1)$^+$

EXAMPLE 11

Compound I-46

Compound (J, Process 7) (43.8 mg, 0.1 mmol) was dissolved in 1 ml of tetrahydrofuran, and then 12 μl (0.15 mmol) of ethyl isocyanate and 28 μl (0.2 mmol) of triethylamine were added thereto, followed by stirring at room temperature for 2 hours. After evaporation of the solvent, the residue was subjected to preparative TLC (chloroform/methanol=9/1) to give 11 mg (yield 22%) of Compound I-46.

$^1$H-NMR (DMSO-d$_6$) δ (ppm): 1.051 (3H, t, J=7.2 Hz), 1.964 (1H, dd, J=5.3, 13.5 Hz), 2.145(3H, s), 2.959(1H, dd, J=7.6, 13.8 Hz), 3.111(2H, m), 4.965(1H, d, J=17.4 Hz), 5.031(1H, d, J=17.6 Hz), 5.835(1H, s), 6.138(1H, t, J=5.7 Hz), 6.265(1H, t, J=5.4 Hz), 6.925 (1H, dd, J=5.4, 7.4 Hz), 7.253–8.059(7H, m), 8.584 (1H, s), 9.200(1H, d, J=7.8 Hz) FAB-MS (m/z): 510 (M+1)$^+$

EXAMPLE 12

Compound I-47

Substantially the same procedure as in example 11 was repeated using 43.8 mg (0.1 mmol) of Compound (J) and 13 μl of phenyl isocyanate to give 13 mg (yield 23%) of Compound I-47.

$^1$H-NMR (DMSO-d$_6$) δ (ppm): 2.063(1H, dd, J=5.2, 13.4 Hz), 2.180(3H, s), 2.999(1H, dd, J=7.3, 13.6 Hz), 3.635–3.727 (2H, m), 4.965(1H, d, J=17.1 Hz), 5.043(1H, d, J=17.4 Hz), 5.776(1H, s), 6.445(1H, dd, J=4.6, 6.6 Hz), 6.928(1H, t, J=7.4 Hz), 7.007(1H, dd, J=5.5, 7.3 Hz), 7.243–8.074(11H, m), 8.583(1H, s), 8.830 (1H, s), 9.198(1H, d, J=7.8 Hz) FAB-MS (m/z): 558 (M+1)$^+$

EXAMPLE 13

Compound I-48

Compound (K, process 8) (44 mg, 0.1 mmol) was dissolved in a mixture of 3 ml of tetrahydrofuran and 0.3 ml of water, and then 110 mg (0.5 mmol) of 1,1-diphenylhydrazine-hydrochloride was added thereto, followed by stirring at room temperature for 4 hours. After dilution with chloroform, the mixture was washed successively with a 10% aqueous solution of hydrogen chloride, water, and a saline solution, and dried over sodium sulfate. After evaporation of the solvent, the residue was subjected to preparative TLC (chloroform/methanol=97/3) to give 30 mg of Compound I-48.

$^1$H-NMR (DMSO-d$_6$) δ (ppm): 2.012(3H, s), 2.137(1H, dd, J=5.2, 13.5 Hz), 3.588(1H, dd, J=7.4, 13.2 Hz), 4.973 (1H, d, J=17.3 Hz), 5.031(1H, d, J=17.3 Hz), 6.086 (1H, s), 6.885(1H, s), 7.105(1H, dd, J=5.4, 7.3 Hz), 7.250–8.045(17H, m), 8.590(1H, s), 9.230(1H, d, J=7.8 Hz) FAB-MS (m/z): 604 (M+1)$^+$

EXAMPLE 14

Compound I-49

Compound (H, Process 5) (59.3 mg, 0.1 mmol) was dissolved in 1 ml of dimethylformamide, and then 21 μl of thiophenol and 8 mg (0.2 mmol) of sodium hydride (60%) were added thereto, followed by stirring at room temperature for 3.5 hours. After dilution with chloroform, the mixture was washed successively with a saturated aqueous solution of sodium bicarbonate, water, and a saline solution, and dried over sodium sulfate. After evaporation of the solvent, the residue was subjected to silica gel column chromatography (chloroform/methanol=99/1) to give 22 mg (yield 41%) of Compound I-49.

$^1$H-NMR (CDCl$_3$) δ (ppm): 2.211(3H, s), 2.661(1H, dd, J=5.7, 14.4 Hz), 3.423(1H, dd, J=7.6, 14.5 Hz), 3.537 (1H, d, J=13.0 Hz), 3.734(1H, d, J=13.0 Hz), 4.545 (1H, d, J=17.3 Hz), 4.761(1H, d, J=17.3 Hz), 6.568 (1H, dd, J=5.5, 7.4 Hz), 7.091–8.003(12H, m), 8.736 (1H, d, J=7.9 Hz) FAB-MS (m/z): 532 (M+1)$^+$

EXAMPLE 15

Compound I-50

Substantially the same procedure as in example 14 was repeated using 59.3 mg of Compound (H) and 22.2 mg of -mercaptopyridine to give 38.7 mg (yield 73%) of Compound I-50.

$^1$H-NMR (CDCl$_3$) δ (ppm): 2.326(3H, s), 2.401(1H, m), 3.339(1H, dd, J=7.4, 14.5 Hz), 3.571(1H, d, J=14.9 Hz), 4.130(1H, d, J-14.8 Hz), 4.918(1H, d, J=16.6 Hz), 5.002(1H, d, J=16.7 Hz), 6.723(1H, dd, J=6.0, 7.4 Hz), 7.173–8.468(11H, m), 9.177(1H, d, J=7.7 Hz) FAB-MS (m/z): 533 (M+1)[1]

EXAMPLE 16

Compound I-51, see Process 6

Compound I-49 ((Process 5; 15 mg, 0.028 mmol) was dissolved in 0.38 ml of chloroform, and then 0.2 ml of chloroform containing 4.8 mg of m-chloroperbenzoic acid was added thereto at −48° C., followed by stirring at the same temperature for 2 hours. After dilution with chloroform, the mixture was washed successively with a saturated aqueous solution of sodium bicarbonate and a saline solution, and dried over sodium sulfate. After evaporation of the solvent, the residue was recrystallized from chloroform to give 6.1 mg (yield 40%) of Compound I-51.

$^1$H-NMR (DMSO-d$_6$) δ (ppm): 2.100(0.87H, s), 2.189(2.13H, s), 4,982(1H, d, J=18.0 Hz), 5.038(1H, d, J=17.9 Hz), 6.056(0.71H, s), 6.337(0.29H, s), 7.145–8.073(12H, m), 8.583(1H, s), 9.200(0.29H, d, J=7.4 Hz), 9.207 (0.71H, d, J=8.3 Hz) FAB-MS (m/z): 548 (M+1)$^+$

EXAMPLE 17

Compound I-40

Substantially the same procedure as in example 16 was repeated using 30 mg of Compound I-50 and 9.5 mg of m-chloroperbenzoic acid to give 12.8 mg (yield 42%) of Compound I-40.

$^1$H-NMR (DMSO-d$_6$) δ (ppm): 2.134(0.25H, s), 2.185(0.75H, s), 4.981(1H, d, J=7.9 Hz), 5.040(1H, d, J=7.6 Hz), 6.212(0.75H, s), 6.449(0.25H, s), 7.088–8.228(11H, m), 8.598(1H, s), 8.809(0.25H, m), 8.919(0.75H, m), 9.198(0.25H, d, J=7.2 Hz), 9.213(0.75H, d, J=7.7 Hz) FAB-MS (m/z): 549 (M+1)$^+$

EXAMPLE 18

Compound I-31

Figure 5:
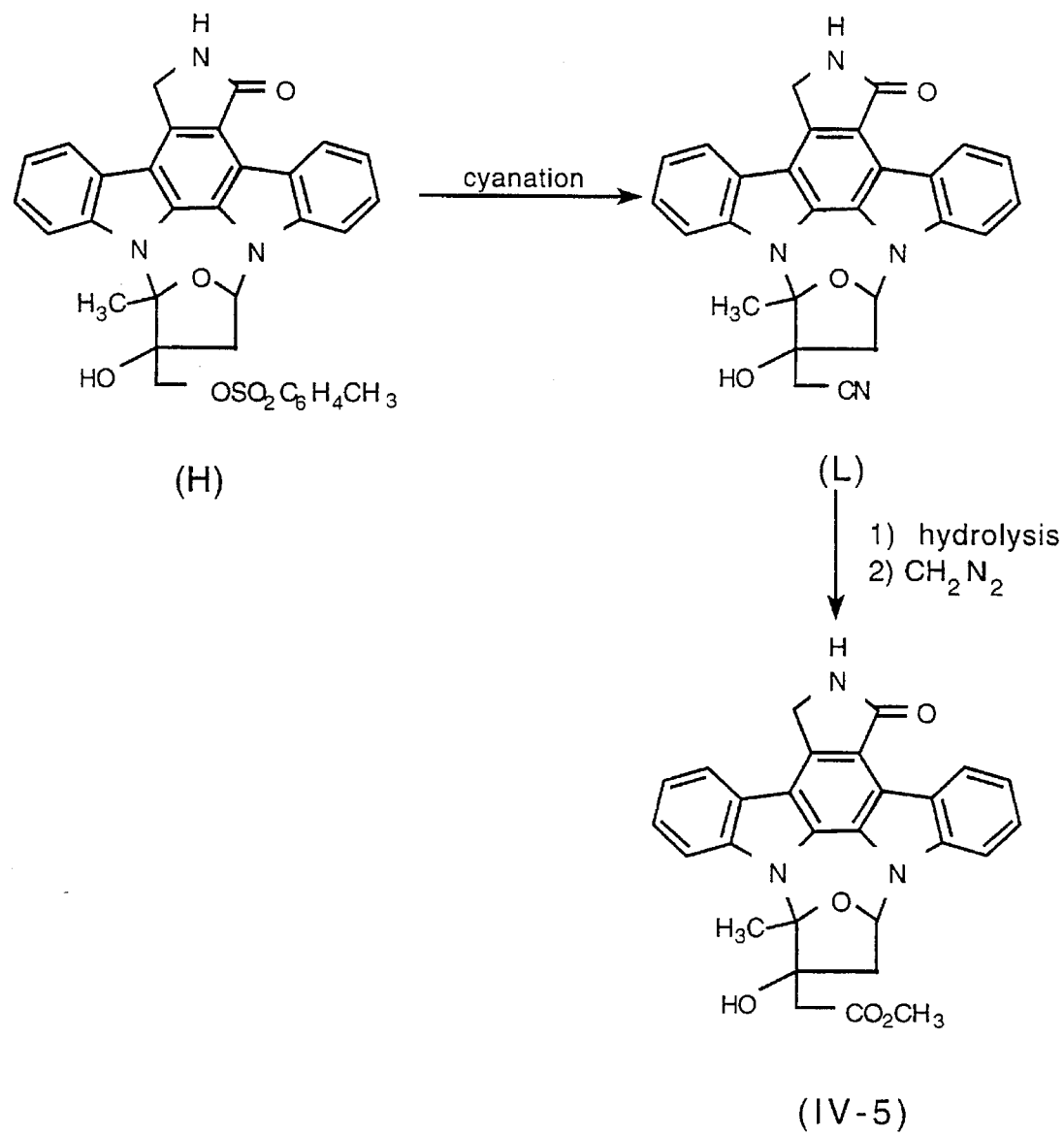
FIG. 5 is a schematic illustration of the synthesis of Compound IV-5.

Compound (H; FIG. 5) (360 mg) was dissolved in 5 ml of dimethylformamide, and then 90 mg of sodium cyanide was added thereto, followed by stirring at 80° C. for 4 hours. After evaporation of the solvent, the residue was hydrolyzed to the corresponding acid and esterified with diazomethane. The residue was subjected to silica gel column chromatography (chloroform/methanol=98/2) to give 30 mg of Compound I-31.

$^1$H-NMR (CDCl$_3$+DMSO-d$_6$; 9/1) δ (ppm): 2.20(3H, s), 4.90 (2H, brs), 6.84(1H, m), 7.12–8.00(7H, m), 9.20 (1H, d, J=8.0 Hz) EI-MS (m/z): 448 (M)$^+$

EXAMPLE 19

Compounds II-1, II-2, and II-3

Figure 6:
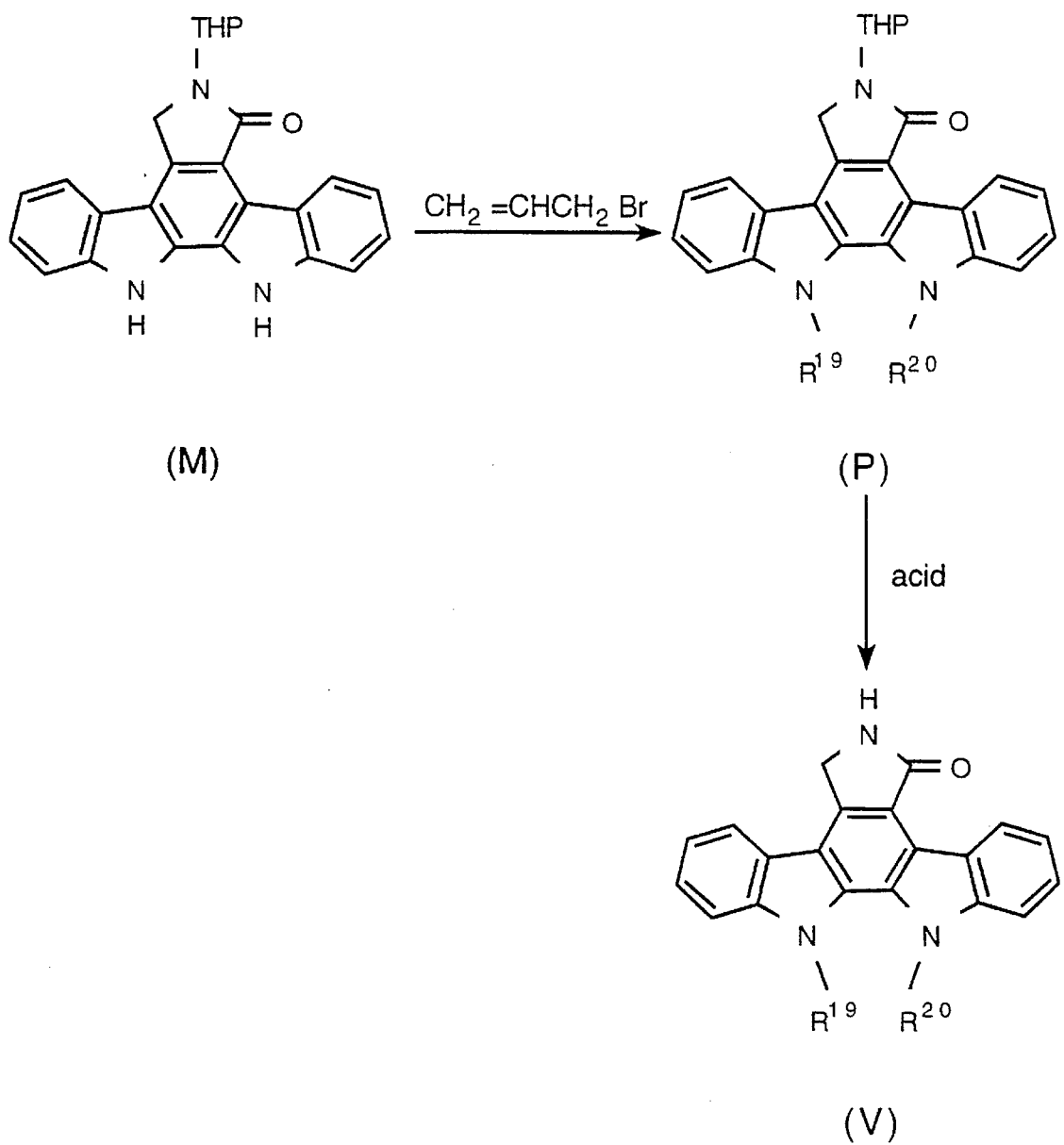
FIG. 6 is a schematic illustration of the synthesis of Compound V.

Compound (M; FIG. 6) (337 mg, 0.85 mmol) was dissolved in 10 ml of dimethylformamide, and 41 mg (1.02 mmol) of sodium hydride (60%) was added thereto under ice cooling, followed by stirring at the same temperature for 10 minutes. Allyl bromide (88 μl, 1.02 mmol) was added thereto and the solution was stirred for 1 hour under ice cooling. To the solution was added 1 ml of methanol, followed by dilution with chloroform. The mixture was washed successively with water and a saline solution, and dried over sodium sulfate. After evaporation of the solvent, the residue was subjected to silica gel column chromatography (ethyl acetate/toluene=1/9) to give 217 mg (yield 54%) of Compound (P-1; R$^{19}$=R$^{20}$=allyl) and 109 mg (yield 30%) of a mixture of Compound (P-2; R$^{19}$=H, R$^{20}$=allyl) and Compound (PR-3; R$^{19}$=allyl, R$^{20}$=H) (1/1.4).

Compound (P-1.; R$^{19}$=R$^{20}$=allyl)

$^1$H-NMR (DMSO-d$_6$) δ (ppm): 5.044–5.478 (11H, m), 6.084–6.223(2H, m), 7.295–8.176(7H, m), 9.415(1H, d, J=7.8 Hz) FAB-MS (m/z): 476 (M+1)$^+$ A mixture of Compound (P-2; R$^{19}$=H, R$^{20}$=allyl) and Compound (P-3; R$^{19}$=allyl, R$^{20}$=H) (1/1.4)

$^1$H-NMR (DMSO-d$_6$) δ (ppm): 4.694(0.58H, dd, J=1.3, 17.3 Hz), 4.757 (0.42H, d, J=17.0 Hz), 5.003–5.172 (3H, m), 4.465(1H, dd, J=1.7, 10.9 Hz), 5.565– 5.619 (2H, m), 6.111–6.222(1H, m), 7.135– 8.177(7H, m), 9.302(0.42H, d, J=8.1 Hz), 9.353(0.58H, d, J=8.1 Hz), 11.555(0.42H, s), 11.713(0.58H, s) FAB-MS (m/z): 436 (M+I)$^+$ Compound (P-1; R$^{19}$=R$^{20}$=allyl) (205 mg, 0.43 mmol) was dissolved in 20 ml of tetrahydrofuran, and 16 ml of a 2M aqueous solution of sulfuric acid was added thereto, followed by stirring at 70° C. for 8 hours. After dilution with ethyl acetate, the mixture was washed successively with water and a saline solution, and dried over sodium sulfate. After evaporation of the solvent, the residue was recrystallized from chloroform/ethyl acetate to give 112 mg (yield 66%) of Compound II-1.

$^1$H-NMR (DMSO-d$^6$) δ (ppm): 4.965(2H, s), 5.067–5.371(8H, m), 6.080–6.211(2H, m), 7.276– 8.051(7H, m), 8.571 (1H, s), 9.434(1H, d, J=7.8 Hz) FAB-MS (m/z): 392 (M+1)$^+$.

Substantially the same procedure as described above was repeated using 100 mg (0.23 mmol) of a mixture of Compound (P-2; R$^{19}$=H, R$^{20}$=allyl) and Compound (P-3; R$^{19}$=allyl, R$^{20}$=H) (1/1.4) to give 39 mg (yield 50%) of a mixture of Compound II-3 and Compound II-2 (1.5/1).

$^1$H-NMR (DMSO-d$_6$) δ (ppm): 4.694 (0.6H, d, J=17.1 Hz), 4.755(0.4H, d, J=17.2 Hz), 4.967 (2H, s), 5.008–5.556 (3H, m), 6.145(1H, m), 7.219–8.278(7H, m), 8.463 (1H, s), 9.318 (0.4H, d, J=7.9 Hz), 9.369(0.6H, d, J=7.9 Hz) FAB-MS (m/Z): 352 (M+1)$^+$.

EXAMPLE 20

Compound I-58

Compound (A-3) (Japanese Published Unexamined Patent Application No. 295588/88) (69 mg, 0.12 mmol) was dissolved in 3.5 ml of dichloroethane, and then 66 μl (0.6 mmol) of thiophenol and 23 μl (0.18 mmol) of boron trifluoride ether complex were added thereto under ice-cooling, followed by stirring at the same temperature for 4.5 hours. The reaction mixture was washed successively with a saturated aqueous solution of sodium bicarbonate, water, and a saline solution, and dried over sodium sulfate. After evaporation of the solvent, the residue was subjected to silica gel column chromatography (toluene/ethyl acetate= 90/10) to give 84 mg (yield 90%) of N,O-diacetylated Compound VI-1.

FAB-MS (m/z): 781 (M+I)$^+$

N,O-Diacetylated Compound VI-1 (70 mg, 0.09 mmol) was dissolved in a mixture of 6 ml of chloroform and 3 ml of methanol, and then 18 μl (0.09 mmol) of 5.1N sodium methoxide was added thereto, followed by stirring at room temperature for 20 minutes. Amberlist 15 (100 mg) was added to the reaction mixture, followed by stirring for one hour, and insoluble material was separated by filtration. After evaporation of the solvent, the residue was subjected to preparative thin layer chromatography (chloroform/methanol=97/3) to give 15 mg (yield 24%) of Compound I-58.

¹H-NMR (DMSO-d₆) δ (ppm): 2.035 (1H, dd, J=4.9, 14.1 Hz), 2.135(3H, s), 3.921(3H, s), 4.982(1H, d, J=16.9 Hz), 5.033(1H, d, J=17.1 Hz), 6.231(1H, s), 6.348(1H, s), 7.096(1H, dd, J=4.9, 7.3 Hz), 7.196–8.060(16H, m), 8.577(1H, s), 9.457(1H, d, J=1.9 Hz) FAB-MS (m/z): 698 (M+1)⁺

EXAMPLE 21

Compound I-59

Substantially the same procedure as in example 20 was repeated using 58 mg (0.1 mmol) of Compound (A-3) and 25 (0.3 mmol) of ethanedithiol to give 50 mg (yield 76% of N,O-diacetylated Compound VI-1.

FAB-MS (m/z): 656 (M+1)⁺

Substantially the same procedure as in example 20 was repeated using 35 mg (0.05 mmol) of N,O-diacetylated Compound VI-1 to give 26 mg (yield 91%) of Compound I-59.

¹H-NMR (DMSO-d₆) δ (ppm): 2.013 (1H, dd, J=4.9, 14.0 Hz), 2.148(3H, s), 3.590–3.641(2H, m), 3.925(3H, s), 4.984(1H, d, J=17.7 Hz), 5.034(1H, d, J=17.7 Hz), 5.931(1H, s), 6.331(1H, s), 7.113(1H, dd, J=5.0, 7.4 Hz), 7.345–8.060(6H, m), 8.588(1H, s), 9.318(1H, d, J=1.5 Hz) FAB-MS (m/z): 572 (M+1)⁺

EXAMPLE 22

Compound I-67

Substantially the same procedure as in process 16, below, was followed using 50.1 mg (0.0862 mmol) of Compound (A-3) and 129.5 mg (0.862 mmol) of 2-mercaptobenzimidazole to give 46.0 mg (yield 75%) of N,O-diacetylated Compound I-67.

FAB-MS (m/z): 714 (M+1)⁺

Substantially the same procedure as in example 20 was repeated using 33.4 mg (0.0468 mmol) of N,O-diacetylated Compound I-67 to give 17.5 mg (yield 59%) of Compound I-67.

¹H-NMR (DMSO-d₆) δ (ppm): 2.995 (1H, dd, J=4.9, 14.1 Hz), 2.139(3H, s), 3.914(3H, s), 4.779(2H, s), 4.979(1H, d, J=17.3 Hz), 5.028(1H, d, J=17.3 Hz), 6.342(1H, s), 7.101(1H, dd, J=4.9, 7.3 Hz), 7.123–8.056(10H, m), 8.617 (1H, s), 9.278(1H, m) FAB-MS (m/z): 630 (M+1)⁺

EXAMPLE 23

Compound I-68

Substantially the same procedure as in process 16, below, was followed using 50 mg (0.0861 mmol) of Compound A-3 and 0.0868 ml (0.861 mmol) of furfurylmercaptan to give 36.0 mg (yield 62%) of N,O-diacetylated Compound I-68.

FAB-MS (m/z): 678 (M+1)⁺

Substantially the same procedure as in example 20 was repeated using 22.7 mg (0.0335 mmol) of N,O-diacetylated Compound I-68 to give 17.7 mg (yield 89%) of Compound I-68.

¹H-NMR (CDCl₃) δ (ppm): 2.209(3H, s)₂.₆₀₇(1H, dd, J=4.9, 14.5 Hz), 3.401(1H, dd, J=7.5, 14.5 Hz), 3.671(2H, s), 3.857(2H, s), 4.103(3H, s), 4.532(1H, brs), 4.789(1H, d, J=16.1 Hz), 4.873(1H, d, J=16.1 Hz), 5.690(1H, s), 6.378(1H, dd, J=1.9, 3.2 Hz), 6.416(1H, dd, J=0.6, 3.2 Hz), 6.846(1H, dd, J=4.8, 7.5HZ), 7.334–7.932(7H, m), 8.961(1H, m) FAB-MS (m/z): 593 (M)⁺

EXAMPLE 24

Compound I-69

Compound (A-3) (100 mg, 0.173 mmol) was dissolved in 4 ml of chloroform, and then 34.0 mg (0.277 mmol) of 1-aminopyrrolidine hydrochloride was added thereto, followed by stirring at room temperature for 4 hours. After evaporation of the solvent under reduced pressure, the residue was subjected to silica gel column chromatography (chloroform/methanol=99/1) to give 100.5 mg (yield 90%) of N,O-diacetylated Compound I-69.

FAB-MS (m/z): 648 (M+1)⁺

Substantially the same procedure as in example 20 was repeated using 40 mg (0.0618 mmol) of N,O-diacetylated Compound I-69 to give 30 mg (yield 86%) of Compound I-69.

¹H-NMR (DMSO-d₆ δ (ppm): 1.910–1.937(4H, m), 2.031(1H, dd, J=4.9, 14.1 Hz), 2.142(3H, s), 2.329–2.635(4H, m), 3.395(1H, dd, J=7.3, 14.1 Hz), 3.925(3H, s), 4.981(1H, d, J=17.0 Hz), 5.030(1H, d, J=17.0 Hz), 7.110(1H, dd, J=4.9, 7.3 Hz), 7.345–8.057 (6H, m), 7.425(1H, s), 8.596(1H, s), 9.210(1H, d, J=1.4 Hz) FAB-MS (m/z): 564 (M+1)⁺

EXAMPLE 25

Compound I-70

Substantially the same procedure as in process 20, was followed using 49.0 mg (0.0846 mmol) of Compound (A-3) and a solution of 15.8 mg (0.145 mmol) of 2-hydrazinopyridine in chloroform to give 35.8 mg (yield 64%) of N,O-diacetylated Compound I-70.

FAB-MS (m/z): 671 (M+1)⁺

Substantially the same procedure as in example 20 was repeated using 24.6 mg (0.0367 mmol) of N,O-diacetylated Compound I-70 to give 11.8 mg (yield 55%) of Compound I-70.

¹H-NMR (DMSO-d₆) δ (ppm): 2.039 (1H, dd, J=5.0, 13.9 Hz), 2.153 (3H,S), 3.418(1H, dd, J=7.2, 13.9 Hz) 3.933 (3H, s), 5.001(1H, d, J=17.5 Hz), 5.057(1H, d, J=17.5 Hz), 6.366(1H, s), 6.748(1H, m), 7. 164 (1H, dd, J=5.0, 7.2 Hz), 7.301–8.120(9H, m), 8.242(1H, s), 8.656(1H, s), 9.368(1H, s), 10.738(1H, s) FAB-MS (m/z): 587 (M+1)⁺

EXAMPLE 26

Compound I-71

Substantially the same procedure as in process 16, below, was followed using 50 mg (0.0861 mmol) of Compound (A-3) and 200 mg (1.41 mmol) of 2-dimethylaminoethanethiol hydrochloride to give 56.3 mg (yield 98%) of N,O-diacetylated Compound I-71.

FAB-MS (m/z): 668 (M+1)⁺

Substantially the same procedure as in example 20 was repeated using 36.6 mg (0.0548 mmol) of N,O-diacetylated Compound I-71 to give 28.4 mg (yield 89%) of Compound I-71.

¹H-NMR (DMSO-d₆) δ (ppm): 2.011 (1H, dd, J=4.9, 14.1 Hz), 2.142(9H, s), 2.460–2.584(4H, m), 3.404(1H, dd, J=7.3, 14.1 Hz), 3.923(3H, s), 3.950(2H, s), 4.951–5.054(2H, m), 6.336(1H, s), 7.111(1H, dd, J=4.9, 7.3 Hz), 7.338–8.060(6H, m), 8.595(1H, s), 9.137(1H, d, J=1.3 Hz) FAB-MS (m/z): 585 (M+1)⁺

EXAMPLE 27

Compound I-72

Substantially the same procedure as in process 16, below, was followed using 30 mg (0.0516 mmol) of Compound (A-3) and 52.2 mg (0.516 mmol) of 1H-1,2,4-triazole-3-thiol to give 31.4 mg (yield 92%) of N,O-diacetylated Compound I-72.

FAB-MS (m/z): 665 (M+1)$^+$

Substantially the same procedure as in example 20 was repeated using 15 mg (0.0226 mmol) of N,O-diacetylated Compound I-72 to give crude Compound I-72. Chloroform/methanol (90/10) was added thereto, followed by stirring to give 10.9 mg (yield 83%) of Compound I-72 as a precipitate.

$^1$H-NMR (DMSO-d$_6$) δ (ppm): 2.006 (1H, dd, J=4.9, 13.9 Hz), 2.144(3H, s), 3.375(1H, dd, J=7.3, 13.9 Hz), 3.921 (3H, s), 4.559(2H, brs), 4.977 (1H, d, J=17.4 Hz), 5.033(1H, d, J=17.4 Hz), 6.332 (1H, s), 7.106(1H, dd, J=4.9, 7.3 Hz), 7.341–8.062 (6H, m), 8.614(1H, s), 9.202(1H, d, J=1.5 Hz) FAB-MS (m/z): 581 (M+1)$^+$

EXAMPLE 28

Compound I-73

Compound (A-3) (97.5 mg, 0.168 mmol) was dissolved in 4 ml of tetrahydrofuran, and then an aqueous solution of 25.1 mg (0.0950 mmol) of aminoguanidine sulfate was added thereto, followed by stirring at room temperature for 3 hours. Ethyl acetate was added thereto, followed by stirring, and the insoluble matters were collected by filtration and subjected to silica gel column chromatography (chloroform/methanol=85/15) to give 87.1 mg (yield 82%) of N,O-diacetylated Compound I-73.

FAB-MS (m/z): 636 (M+1)$^+$

Substantially the same procedure as in example 20 was repeated using 69.6 mg (0.110 mmol) of N,O-diacetylated Compound I-73 to give 37.2 mg (yield 62%) of Compound I-73.

$^1$H-NMR (DMSO-d$_6$) δ (ppm): 2.046 (1H, dd, J=4.9, 14.2 Hz), 2.148(3H, s), 3.406(1H, dd, J=7.5, 14.2 Hz), 3.929 (3H, s), 4.988(1H, d, J=17.3 Hz), 5.045(1H, d, J=17.3 Hz), 5.637–6.129(4H, m), 6.350(1H, s), 7.156(1H, dd, J=4.9, 7.5 Hz), 7.345–8.092(6H, m), 8.206 (1H, s), 8.603(1H, s), 9.271(1H, d, J=1.7 Hz) FAB-MS (m/z): 552 (M+1)$^+$

EXAMPLE 29

Compound I-74

Substantially the same procedure as in process 20, below, was followed using 103.8 mg (0.179 mmol) of Compound (A-3) and 0.020 ml (0.207 mmol) of 4-aminomorpholine to give 82.8 mg (yield 70%) of N,O-diacetylated Compound I-74.

FAB-MS (m/z): 663 (M)$^+$

Substantially the same procedure as in example 20, below, was repeated using 50.6 mg (0.0763 mmol) of N,O-diacetylated Compound I-74 to give 36.4 mg (yield 82%) of Compound I-74.

$^1$H-NMR (DMSO-d$_6$) δ (ppm): 2.042 (1H, dd, J=4.8, 14.3 Hz), 2.144(3H, s), 3.139–3.163(4H, m), 3.404(1H, dd, J=7.5, 14.3 Hz), 3.792–3.815(4H, m), 3.927(3H, s), 4.984(1H, d, J=17.3 Hz), 5.040(1H, d, J=17.3 Hz), 6.352(1H, s), 7.132(1H, dd, J=4.8, 7.5 Hz), 7.344–8.065(6H, m), 7.897(1H, s), 8.610(1H, s), 9.316(1H, d, J=1.7 Hz) FAB-MS (m/z): 580 (M+1)$^+$

EXAMPLE 30

Compound I-75

Substantially the same procedure as in process 20, below, was followed using 100 mg (0.173 mmol) of Compound A-3 and 16.7 mg (0.173 mmol) of 1,1-dimethylhydrazine hydrochloride to give 52.3 mg (yield 49%) of N,O-diacetylated Compound I-75.

FAB-MS (m/z): 622 (M+1)$^+$

Substantially the same procedure as in example 20 was repeated using 38.4 mg (0.0618 mmol) of N,O-diacetylated Compound I-75 to give 10.9 mg (yield 33%) of Compound I-75.

$^1$H-NMR (DMSO-d$_6$) δ (ppm): 2.037(1H, dd, J=5.0, 14.1 Hz), 2.142(3H, s), 2.939(6H, s), 3.399(1H, dd, J=7.5, 14.1 Hz), 3.926(3H, s), 4.981(1H, d, J=17.7 Hz), 5.037(1H, d, J=17.7 Hz), 6.342(1H, s), 7.118(1H, dd, J=5.0, 7.5 Hz), 7.342– 8.063(6H, m), 7.533(1H, s), 8.601(1H, s), 9.258(1H, s) FAB-MS (m/z): 538 (M+1)$^+$

EXAMPLE 31

Compound I-76

Substantially the same procedure as in process 20, below, was followed using 99.5 mg (0.172 mmol) of Compound (A-3) and 42.4 mg of 1-amino-4-methylpiperizine to give N,O-diacetylated Compound I-76.

Then, substantially the same procedure as in example 20 was repeated using the above N,O-diacetylated Compound I-76 give 19.4 mg [yield from Compound (A-3) 19%] of Compound I-76.

$^1$H-NMR (DMSO-d$_6$) δ (ppm): 2.040 (1H, dd, J=5.0, 14.0 Hz), 2.144(3H, s), 2.268(3H, s), 2.553(4H, m), 3.167(4H, m), 3.401(1H, dd, J=7.2, 14.0 Hz), 3.927(3H, s), 4.982(1H, d, J=17.1 Hz), 5.038(1H, d, J=17.1 Hz), 6.345(1H, s), 7.128(1H, dd, J=5.0, 7.2 Hz), 7.343–8.065(6H, m), 7.827 (1H, s), 8.609(1H, s), 9.299(1H, d, J=1.2 Hz) FAB-MS (m/z): 593 (M+1)$^+$ Process 1

Compound (III-1) [Compound (III) in which R$^1$ and R$^2$ are independently halogen, and X is CH$_2$OH] can be prepared by the following reaction step:

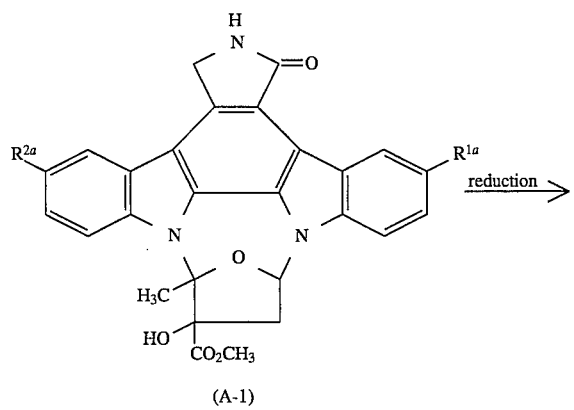

(A-1)

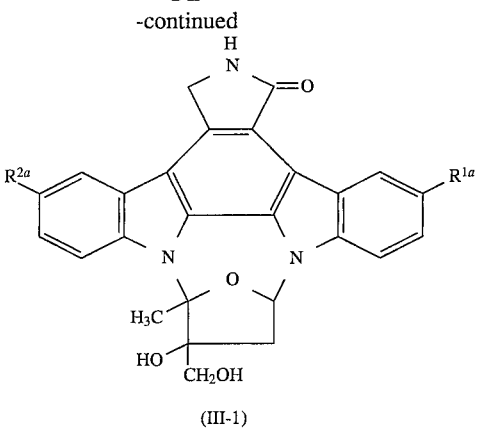

(III-1)

(In the formula, $R^{1a}$ and $R^{2a}$ independently represent halogen.)

The halogen in the definition of $R^{1a}$ and $R^{2a}$ has the same meaning as defined above.

The starting compound (A-1) is disclosed in Japanese Published Unexamined Patent Application No. 120388/87, hereby incorporated by reference.

Compound (III-1) can be obtained by treatment of Compound (A-1) with 2 to 10 equivalents of a reducing agent in an inert solvent. An example of the reducing agent is sodium borohydride. An example of the inert solvent is a mixed solvent of an ether such as diethyl ether or tetrahydrofuran and an alcohol such as methanol or ethanol. The ratio of the ether to the alcohol is preferably 1:1 to 5:1. The reaction is completed in 3 to 24 hours at 0° to 50° C.

Process 2

Compound (III-2) [Compound (III) in which $R^1$ is halogen, $R^2$ is hydrogen or halogen and X is $CONHR^{15}$] can be prepared by the following reaction steps, which are illustrated in FIG. 2. (In the formulae, $R^{1a}$, $R^2$, and $R^{15}$ have the same meanings as defined above.)

The starting compound (A-2) is disclosed in Japanese Published Unexamined Patent Application No. 120388/87 (supra).

Compound (B) can be obtained by hydrolysis of Compound (A-2) with 1 to 1.5 equivalents of an alkali metal hydroxide. Examples of the alkali metal hydroxide are sodium hydroxide and potassium hydroxide. As a reaction solvent, dimethylformamide or the like is used. The reaction is completed in 1 to 24 hours at 0° to 50° C.

Compound (C) can be obtained by reaction of Compound (B) with 3 to 20 equivalents of an acetylating agent. An example of the acetylating agent is acetic anhydride. As a reaction solvent, pyridine or the like is used. The reaction is completed in 1 hours to 4 days at 0° to 50° C.

Compound (D) can be obtained by reaction of Compound (C) with a halogenating agent of a carboxyl group, which serves also as a solvent. Examples of the halogenating agent are thionyl chloride and oxalyl chloride. The reaction is completed in 1 to 3 hours at 50° to 100° C.

Compound (E) can be obtained by reaction of Compound (D) with 5 to 30 equivalents of $R^{15}NH_2$. As a reaction solvent, a halogenated hydrocarbon such as methylene chloride, chloroform, or ethylene dichloride, dimethylformamide, or the like is used. The reaction is completed in 1 to 24 hours at 0° to 50° C.

Compound (III-2) can be obtained by deacetylation of Compound (E) with 0.5 to 10 equivalents of a deacetylating agent. Examples of the deacetylating agent are alkali metal alkoxylate such as sodium methylate and alkali metal hydroxide such as sodium hydroxide. As a reaction solvent, a mixed solvent of a halogenated hydrocarbon such as methylene chloride, chloroform, or ethylene dichloride and an alcohol such as methanol or ethanol, a mixed solvent of an ether such as dioxane or tetrahydrofuran and an alcohol such as methanol or ethanol, or the like is used. The ratio of the halogenated hydrocarbon to the alcohol, or that of the ether to the alcohol is 1:5 to 1:1. The reaction is completed in 5 minutes to 1 hour at 0° to 50° C.

Process 3

Compound (III-3) [Compound (III) in which $R^1$ is $CH_2OCONHR^{14}$ and X is $CO_2CH_3$] can be prepared by the following reaction steps, which are illustrated in FIG. 3. (In the formulae, $R^{14}$ represents lower alkyl.)

The starting compound (F) is disclosed in Japanese Published Unexamined Patent Application No. 295588/88 (hereby incorporated by reference).

Compound (G) can be obtained by reaction of Compound (F) with 1 to 5 equivalents of $R^{14}NCO$ in the presence of a base. An example of the base is triethylamine. As a reaction solvent, a mixed solvent of tetrahydrofuran and dimethylformamide, or the like is used. The ratio of tetrahydrofuran to dimethylformamide is 5:1 to 1:1. The reaction is completed in 5 to 24 hours at 10° to 70° C.

Compound (III-3) can be obtained from Compound (G) in a manner similar to that of the preparation of Compound (III-2).

Process 4

Compound (III-4) [Compound III in which $R^1$ is $NHCO_2R^{14}$ and X is $CO_2CH_3$] can be prepared by the following reaction steps depicted in FIG. 4. (In the formulae, $R^{14}$ represents lower alkyl).

The starting compound (N) is disclosed in Japanese Published Unexamined Patent Application No. 295588/88 (hereby incorporated by reference).

Compound (O) can be obtained by reaction of Compound (N) with 1 to 5 equivalents of $CPCO_2R^{14}$ in the presence of 1 to 5 equivalents of a base. An example of the base is triethylamine. As a reaction solvent, a halogenated hydrocarbon such as methylene chloride, chloroform, or ethylene dichloride, or the like is used. The reaction is completed in 1 to 3 hours at 0° to 50° C.

Compound (III-4) can be obtained from Compound (O) in a manner similar to that in the preparation of Compound (III-2).

Process 5

Compound (IV-1) [Compound (IV) in which X is $CH_2SR^{16}$] can be prepared by the following reaction step:

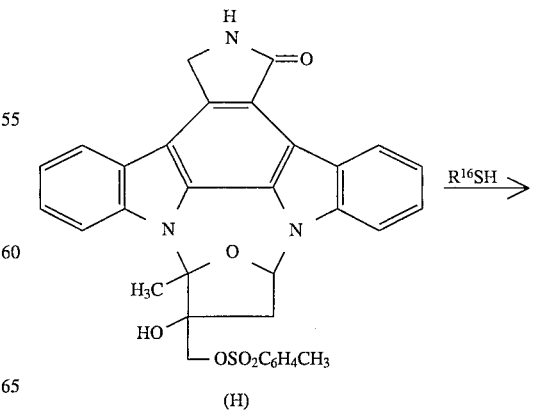

(H)

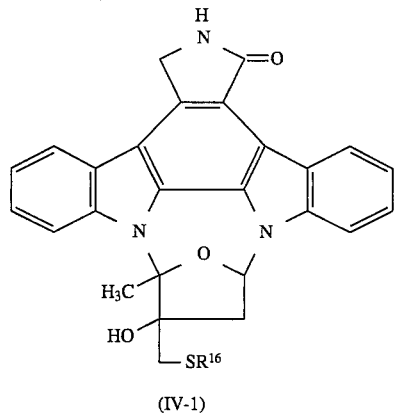

(IV-1)

(In the formulae, $R^{16}$ has the same meaning as defined above.)

The starting compound (H) is disclosed in Japanese Published Unexamined Patent Application No. 155285/87 (hereby incorporated by reference).

Compound (IV-1) can be obtained by reaction of Compound (H) with 1 to 5 equivalents of $R^{16}SH$ in the presence of 1 to 5 equivalents of a base. An example of the base is alkali metal hydride such as sodium hydride. As a reaction solvent, dimethylformamide or the like is used. The reaction is completed in 2 to 5 hours at 0° to 50° C.

Process 6

Compound (IV-2) [Compound (IV) in which X is $CH_2S(O)R^{16}$] can be prepared by the following reaction step:

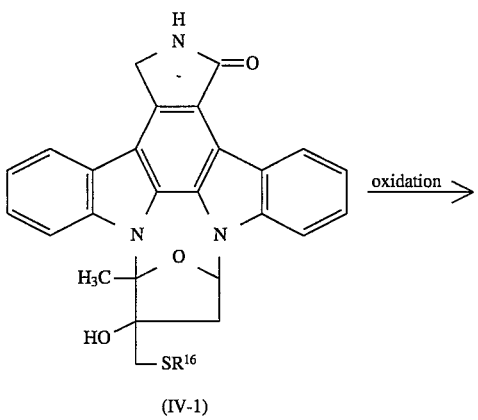

(IV-1)

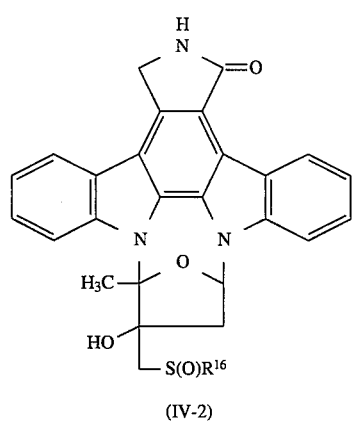

(IV-2)

(In the formulae, $R^{16}$ represents aryl or a heterocyclic group including a nitrogen atom.)

Compound (IV-2) can be obtained by treatment of Compound (IV-1) with 1 to 1.5 equivalents of an oxidant. An example of the oxidant is m-chloroperbenzoic acid. As a reaction solvent, a halogenated hydrocarbon such as methylene chloride, chloroform, or ethylene dichloride, or the like is used. The reaction is completed in 1 to 8 hours at −70° to 0° C.

Process 7

Compound (IV-3) [Compound (IV) in which X is $CH_2NHCONHR^{18}$] can be prepared by the following reaction step:

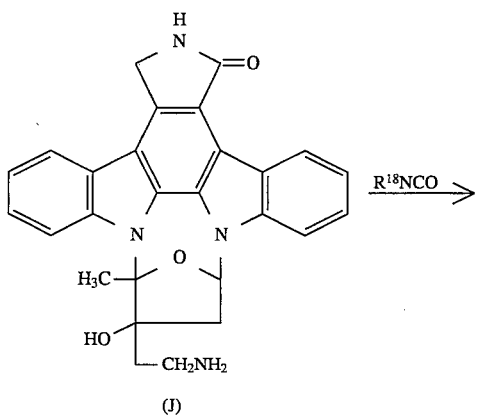

(J)

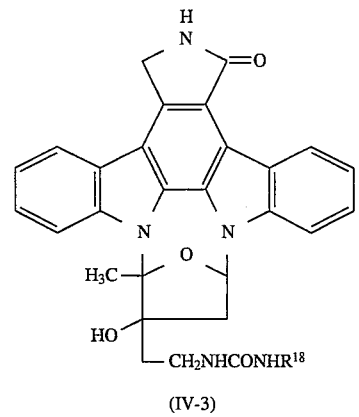

(IV-3)

(In the formulae, $R^{18}$ represents lower alkyl or aryl).

The starting compound (J) is disclosed in Japanese Published Unexamined Patent Application No. 155285/87 (hereby incorporated by reference).

Compound (IV-3) can be obtained by reaction of Compound (J) with 1 to 3 equivalents of $R^{18}NCO$ in the presence of 1 to 3 equivalents of a base. An example of the base is triethylamine. As a reaction solvent, tetrahydrofuran or the like is used. The reaction is completed in 1 to 5 hours at 0° to 50° C.

Process 8

Compound (IV-4) [Compound (IV) in which X is $CH=NN(R^{17})_2$] can be prepared by the following reaction step:

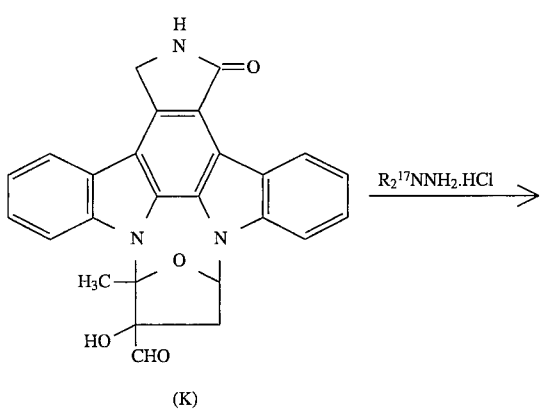

(K)

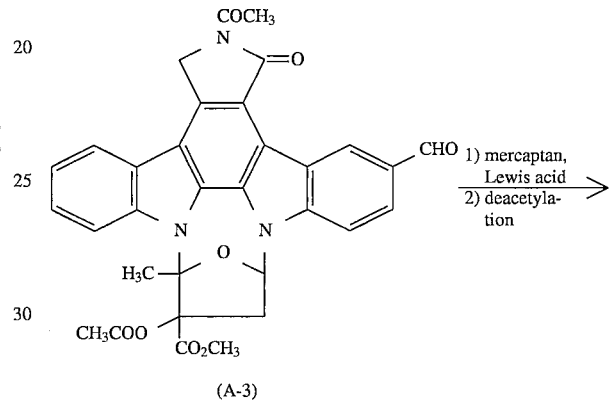

(A-3)

(IV-4)

(In the formulae, $R^{17}$ represents aryl.)

The starting compound (K) is disclosed in Japanese Published Unexamined Patent Application No. 295588/88 (supra).

Compound (IV-4) can be obtained by reaction of Compound (K) with 2 to 10 equivalents of $R^{17}{}_2NNH_2 \cdot HCl$. As a reaction solvent, a mixed solvent of an ether such as dioxane or tetrahydrofuran and water, or the like is used. The ratio of the ether to water is 1:10 to 1:2. The reaction is completed in 2 to 8 hours at 0° to 50° C.

Process 9

Compound (IV-5) [Compound (IV) in which X is $CH_2CO_2CH_3$] can be prepared by the following reaction steps, which are illustrated in FIG. 5.

Compound (L) can be obtained by reaction of Compound (H) with 1 to 5 equivalents of a cyanating agent. An example of the cyanating agent is an alkali metal cyanide such as sodium cyanide. As a reaction solvent, dimethylformamide or the like is used. The reaction is completed in 1 to 24 hours at 20° to 100° C.

Compound (IV-5) can be obtained by hydrolysis of Compound (L) with 10 to 50 ml/mmol of an aqueous solution of an alkali metal hydroxide, followed by treatment with 2 to 10 equivalents of $CH_2N_2$. Examples of the aqueous solution of an alkali metal hydroxide are a 30% aqueous solution of sodium hydroxide and a 30% aqueous solution of potassium hydroxide. In the hydrolysis, ethylene glycol or the like is used as a reaction solvent, and the reaction is completed in 1 to 3 hours at 120° to 180° C. In the treatment with $CH_2N_2$, dimethylformamide or the like is used as a reaction solvent, and the reaction is completed in 1 to 5 hours at 0° to 30° C.

Process 10

Compound (V) can be prepared by the following reaction steps, which are illustrated in FIG. 6. (In the formulae, THP represents tetrahydropyranyl; one of $R^{19}$ and $R^{20}$ is hydrogen and the other is allyl, or both of them are allyl.)

The starting compound (M) is disclosed in J. Chem. Soc. Perkin Trans. I, 2475 (1990).

Compound (P) can be obtained by reaction of Compound (M) with 1 to 1.5 equivalents of allyl bromide in the presence of 1 to 1.5 equivalents of a base. An example of the base is an alkali metal hydride such as sodium hydride. As a reaction solvent, dimethylformamide or the like is used. The reaction is completed in 1 to 5 hours at −10° to 10° C.

Compound (V) can be obtained by treatment of Compound (P) with 4 to 50 ml/mmol of an aqueous solution of an acid. An example of the aqueous solution of an acid is 2M $H_2SO_4$. As a reaction solvent, tetrahydrofuran or the like is used. The reaction is completed in 5 to 24 hours at to 100° C.

Process 11

Compound (VI-1) [Compound VI in which $R^1$ is $CH(SC_6H_6)_2$ or $CH(—SCH_2CH_2S—)$] can be prepared by the following reaction step:

(VI-1)

[In the formulae, $R^{1b}$ represents $CH(SC_6H_5)_2$ or $CH(—SCH_2CH_2S—)$.]

The starting compound (A-3) is disclosed in Japanese Published Unexamined Patent Application No. 295588/88.

N,O-Diacetylated Compound (VI-1) can be obtained by reaction of Compound (A-3) with 1 to 10 equivalents of a corresponding mercaptan in the presence of a Lewis acid in an inert solvent. An example of the Lewis acid is boron trifluoride ether complex. An example of the inert solvent is dichloroethane. The reaction is completed in 1 to 24 hours at 0° C. to room temperature.

Then, Compound (VI-1) can be obtained by hydrolysis of N,O-diacetylated Compound (VI-1) with 1 to 5 equivalents of an alkali metal alkoxide. Examples of the alkali metal alkoxide are sodium methoxide and potassium ethoxide. As a reaction solvent, chloroform, methanol, a mixture thereof, or the like is used. The reaction is completed in 0.1 to 24 hours at 0° to 50° C.

Process 12

Compound (VI-2) [Compound (VI) in which $R^1$ is $CH_2SR^{24}$] can be prepared by the following reaction step:

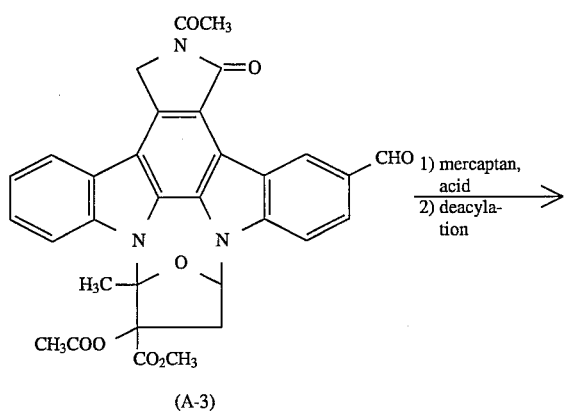

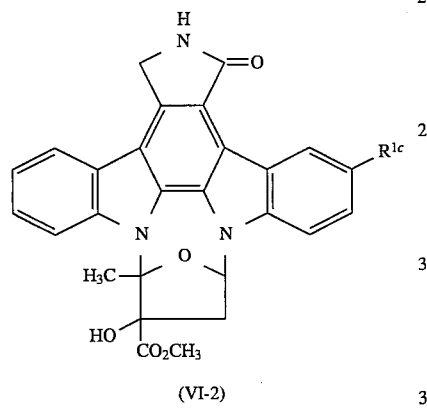

(In the formulae, $R^{1c}$ represents $CH_2SR^{24}$.)

N,O-Diacetylated Compound (VI-2) can be obtained by reaction of Compound (A-3) with 1 to 10 equivalents of a corresponding mercaptan in the presence of an acid in an inert solvent. An example of the acid is (±)-10-camphorsulfonic acid. As the inert solvent, chloroform, methanol, a mixture thereof, or the like is used. The reaction is completed in 1 to 48 hours at 0° to 50° C.

Then, Compound (VI-2) can be obtained by hydrolysis of N,O-diacetylated Compound (VI-2) with 1 to 5 equivalents of an alkali metal alkoxide. Examples of the alkali metal alkoxide are sodium methoxide and potassium ethoxide. As a reaction solvent, chloroform, methanol, a mixture thereof, or the like is used. The reaction is completed in 0.1 to 24 hours at 0° to 50° C.

Process 13

Compound (VI-3) [Compound (VI) in which $R^1$ is $CH=NR^{25}$] can be prepared by the following reaction step:

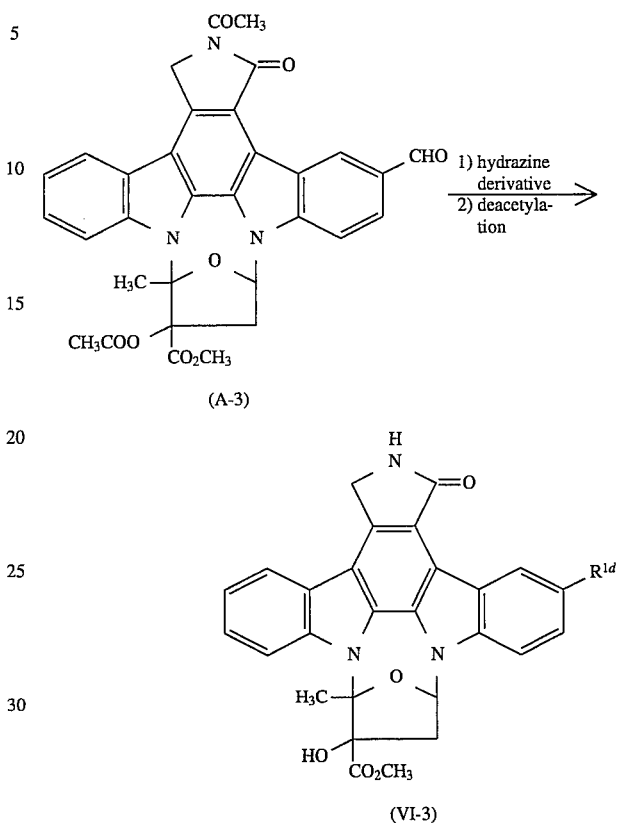

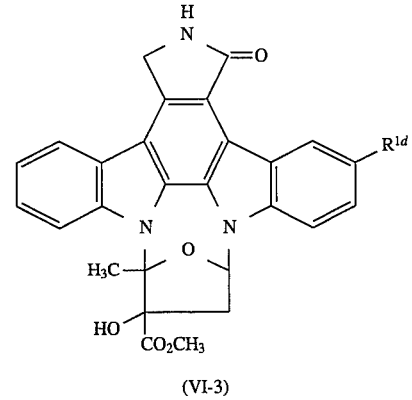

(In the formulae, $R^{1d}$ represents $CH=NR^{25}$.)

N,O-Diacetylated Compound (VI-3) can be obtained by reaction of Compound (A-3) with 1 to 10 equivalents of a corresponding hydrazine derivative in the presence of an acid in an inert solvent. An example of the acid is hydrochloric acid. As the inert solvent, chloroform, methanol, tetrahydrofuran, water, a mixture thereof, or the like is used. The reaction is completed in 1 to 48 hours at 0° to 50° C.

Alternatively, N,O-diacetylated Compound (VI-3) may be obtained by reaction of Compound (A-3) with 1 to 10 equivalents of an acid addition salt of the corresponding hydrazine derivative in an inert solvent. Examples of the acid are hydrochloric acid and sulfuric acid. As the inert solvent, chloroform, methanol, tetrahydrofuran, water, a mixture thereof, or the like is used. The reaction is completed in 1 to 48 hours at 0° to 50° C.

Then, Compound (VI-3) can be obtained by hydrolysis of N,O-diacetylated Compound (VI-3) with 1 to 5 equivalents of an alkali metal alkoxide. Examples of the alkali metal alkoxide ar sodium methoxide and potassium ethoxide. As a reaction solvent, chloroform, methanol, a mixture thereof, or

39 the like is used. The reaction is completed in 0.1 to 24 hours at 0° to 50° C.

Process 14
Compound I-57

Compound (B-1) (see Japanese unexamined patent application number 155285/87), (393 mg, 0.9 mmol), α,ε-dibenzyloxycarbonyl-L-lysine (1.06 g, 2.6 mmol), 4-methylmorpholine (0.1 ml, 0.9 mmol), and N-hydroxysuccinimide (312 mg, 2.7 mmol) were dissolved in 25 ml of tetrahydrofuran, and then 6 ml of tetrahydrofuran containing 558 mg (2.7 mmol) of dicyclohexylcarbodiimide was added thereto under ice-cooling, followed by stirring at room temperature for 12 hours. After insoluble matters were filtered off and the solvent was evaporated, the residue was subjected to silica gel column chromatography (chloroform/methanol=98/2) to give 385 mg (yield 51%) of protected Compound I-57. Compound (B-1) is shown below:

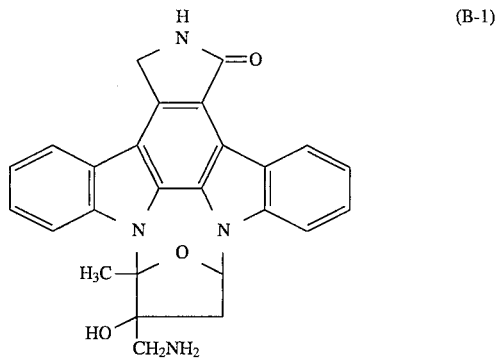

(B-1)

The above protected Compound I-57 (355 mg, 0.42 mmol) was dissolved in 10 ml of dimethylformamide, and then 500 mg of 10% palladium carbon was added thereto, followed by stirring in an atmosphere of hydrogen at 50° C. for 10 hours. After filtration with Celite and evaporation of the solvent, the residue was subjected to silica gel column chromatography (chloroform/methanol/28% aqueous ammonia=80/20/2) and treated with 1.7N hydrochloric acid/ethyl acetate to give 120 mg (yield 44%) of Compound I-57 as the hydrochloride.

$^1$H-NMR (DMSO-$d_6$/$D_2O$=10/1) δ (ppm): 1.40–2.32(7H, m), 2.22(3H, s), 2.64–3.24(3H, m), 3.40–4.20(3H, m), 5.04(2H, s), 7.10(1H, m), 7.30–8.20(7H, m), 8.96(1H, brs), 9.20(1H, d, J=8 Hz) SI-MS (m/z): 567 (M+1)$^+$ Process 15
Compound I-66

Compound I, ($Z^1$, $Z^2$, $R^5$, $R^6$=H; R=OH; X=$CO_2CH_3$; $R^1$=$R^2$=$CH_2SC_2H_5$) (see WO 94/02488) (10 mg, 0.016 mmol) was dissolved in 0.5 ml of chloroform, and then 5.6 mg (0.032 mmol) of m-chloroperbenzoic acid was added thereto at −48° C., followed by stirring at the same temperature for 0.5 hour. The reaction mixture was washed successively with a saturated aqueous solution of sodium bicarbonate, water, and a saline solution, and dried over sodium sulfate. After evaporation of the solvent, the residue was subjected to silica gel column chromatography (chloroform/methanol=90/10) to give 10 mg (yield quant.) of Compound I-66.

$^1$H-NMR (CDCl$_3$/CD$_3$OD=10/1) δ (ppm): 1.334–1.429(6H, m), 2.120, 2.136, 2.148, 2.157(3H, 4s), 3.270–3.372 (1H, m), 4.082(3H, s), 4.619–4.792(2H, m), 6.832 (1H, brs), 7.225–7.857 (5H, m), 8.939(0.6H, d, J=7.6 Hz), 8.997(0.4H, d, J=8.3 Hz) FAB-MS (m/z): 648 (M+1)$^+$ Process 16
Compound I-60

Compound (A-3) (58 mg, 0.1 mmol) was dissolved in 3 ml of chloroform, and then 112 mg (1 mmol) of 2-mercaptopyridine and 49 mg (0.21 mmol) of (±)-10-camphorsulfonic acid were added thereto, followed by stirring at room temperature for 12 hours. The reaction mixture was washed successively with a saturated aqueous solution of sodium bicarbonate, water, and a saline solution, and dried over sodium sulfate. After evaporation of the solvent, the residue was subjected to preparative thin layer chromatography (chloroform/methanol=99/1) to give 44 mg (yield 65%) of N,O-diacetylated Compound I-60.

FAB-MS (m/z): 675 (M+1)$^+$

Substantially the same procedure as in example 20 was repeated using 38 mg (0.056 mmol) of N,O-diacetylated Compound I-60 to give 29 mg (yield 87%) of Compound I-60.

$^1$H-NMR (CDCl$_3$) δ (ppm): 2.160 (3H, s), 2.849(1H, dd, J=4.9, 14.4 Hz), 4.054(3H, s), 4.556(1H, d, J=12.9 Hz), 4.622(1H, d, J=14.9 Hz), 4.656(1H, d, J=12.7 Hz), 4.734(1H, d, J=16.1 Hz), 5.048(1H, brs), 5.352(1H, s), 6.807(1H, dd, J=2.6, 7.4 Hz), 7.000–7.949 (9H, m), 8.533–8.553 (1H, m), 8.918 (1H, d, J=1.2 Hz) FAB-MS (m/z): 591 (M+1)$^+$ Process 17
Compound I-62

Substantially the same procedure as in process 16 was repeated using 58 mg (0.1 mmol) of Compound (A-3) and 112 mg (1 mmol) of 2-mercaptopyrimidine to give 65 mg (yield of N,O-diacetylated Compound I-62.

FAB-MS (m/z) : 676 (M+1)$^+$

Substantially the same procedure as in example 20 was repeated using 58 mg (0.086 mmol) of N$_1$O-diacetylated Compound I-62 to give 49 mg (yield 96%) of Compound I-62.

$^1$H-NMR (CDCl$_3$) δ (ppm): 2.200(3H, s), 4.066(3H, s), 4.595(1H, d, J=13.2 Hz), 4,657(1H, d, J=13.2 Hz), 4.793(1H, d, J=17.1 Hz), 4.892(1H, d, J=17.1 Hz), 6.878(1H, dd, J=4.8, 7.4 Hz), 6.987–7.920(7H, m), 8.583(2H, d, J=4.8 Hz), 9.162(1H, s) FAB-MS (m/z): 592 (M+1)$^+$ Process 18
Compound I-64

Compound I-60 (19 mg, 0.032 mmol) was dissolved in 0.5 ml of chloroform, and then 5.5 mg (0.032 mmol) of m-chloroperbenzoic acid was added thereto at −48° C., followed by stirring at the same temperature for 1.5 hours. The reaction mixture was washed successively with a saturated aqueous solution of sodium bicarbonate and a saline solution, and dried over sodium sulfate. After evaporation of the solvent, the residue was subjected to preparative thin layer chromatography (chloroform/methanol=85/15) to give 13 mg (yield 67%) of Compound I-64.

$^1$H-NMR (CDCl$_3$) δ (ppm): 2.184(1.5H, s), 2.191(1.5H, s), 2.572(0.5H, dd, J=4.6, 14.4 Hz), 2.609(0.5H, dd, J=4.5, 14.7 Hz), 3.449(0.5H, dd, J=7.4, 11.6 Hz), 3.485(0.5H, dd, J=7.7, 11.4 Hz), 4.095(3H, s), 4.173 (0.5H, d, J=13.1 Hz), 4.230(0.5H, d, J=13.2 Hz), 4.485(0.5H, d, J=13.2 Hz), 4.538(0.5H, d, J=12.9 Hz), 4.588–4.828(3H, m), 5.582(0.5H, brs), 5.723(0.5H, brs), 6.819–6.873(1H, m), 7.227–7.894(9H, m), 8.371 (0.5H, s), 8.607(0.5H, s), 8.716–8.747(1H, m) FAB-MS (m/z): 607 (M+1)$^+$ Process 19
Compound 1–63

Substantially the same procedure as in process 18 was repeated using 36 mg (0.06 mmol) of Compound I-62 to give 20 mg (yield 55%) of Compound I-63.

$^1$H-NMR (CDCl$_3$) δ (ppm): 2.170(3H, s), 2.501(0.6H, dd, J=4.7, 14.6 Hz), 2.564(0.4H, dd, J=4.6, 14.5 Hz), 3.410–3.487 (1H, m), 4.076(1.2H, s), 4.082(1.8H, s), 4.326–4.765(5H, m), 5.682(0.4H, brs), 5.796(0.6H, brs), 6.788–6.834(1H, m), 7.203–7.877(7H, m), 8.267(1H, s), 8.736–8.751(2H, m) FAB-MS (m/z): 608 (M+1)⁺

Process 20

Compound I-61

Compound (A-3) (58 mg, 0.1 mmol) was dissolved in a mixture of 6 ml of chloroform and 3 ml of methanol, and then 0.5 ml of an aqueous solution of 91 mg (0.5 mmol) of 2-hydrazino-2-imidazoline and 0.05 ml of 3N hydrochloric acid was added thereto, followed by stirring at room temperature for 3 hours. The reaction mixture was washed successively with a saturated aqueous solution of sodium bicarbonate and a saline solution, and dried over sodium sulfate. After evaporation of the solvent, the residue was subjected to silica gel column chromatography (chloroform/methanol=90/100) to give 57 mg (yield 86%) of N,O-diacetylated Compound I-61.

FAB-MS (m/z): 662 (M+1)⁺

Substantially the same procedure as in example 20 was repeated using 47 mg (0.07 mmol) of N,O-diacetylated Compound I-61 to give 34 mg (yield 84%) of Compound I-61.

¹H-NMR (DMSO-D₆) δ (ppm): 2.052 (1H, dd, J=4.9, 14.0 Hz), 2.150(3H, s), 3.933(3H, s), 4.995(1H, d, J=17.3 Hz), 5.044(1H, d, J=17.3 Hz), 6.372(1H, brs), 7.164(1H, dd, J=5.0, 7.2 Hz), 7.353–8.166(6H, m), 8.213(1H, s), 8.619(1H, s), 9.214(1H, d, J=1.3 Hz) FAB-MS (m/z): 578 (M+1)⁺

Process 21

Compound II-4

Compound (D-1) (J. Chem. Soc. Perkin Trans. 1:2475, 823.7 mg, 2.083 mmol) was dissolved in 20 ml of dimethylformamide, and 166.4 mg (4.16 mmol) of sodium hydride (60%) was added thereto under ice cooling, followed by stirring at the same temperature for 10 minutes. Allyl bromide (0.45 ml, 5.2 mmol) was added thereto and the solution was stirred for 2 hours under ice cooling. After dilution with chloroform, water was added thereto and the organic layer was separated, washed with a saline solution, and dried over magnesium sulfate. After evaporation of the solvent, the residue was subjected to silica gel column chromatography (ethyl acetate/toluene=1/15) to give 735.0 mg (yield 74%) of Compound (E-1).

¹H-NMR (DMSO-d₆) δ (ppm): 1.563–2.154 (6H, m), 3.657(1H, m), 4.008(1H, m), 5.044–5.478(11H, m), 6.153(2H, m), 7.240–7.640(6H, m), 8.167(1H, d, J=7.8 Hz), 9.415(1H, d, J=7.8 Hz) FAB-MS (m/z): 476 (M+1)⁺

Sodium borohydride (77.7 mg, 2.05 mmol) was suspended in 20 ml of tetrahydrofuran, and 231.0 mg (1.82 mmol) of iodine was added thereto at 0° C. in an atmosphere of argon, followed by stirring at the same temperature for 15 minutes. Compound (E-1) (136.7 mg, 0,287 mmol) was added thereto at the same temperature and the mixture was stirred at room temperature for 4.5 hours. After the reaction mixture was cooled to 0° C., 3.7 ml of 1N sodium hydroxide and 3.7 ml of a 35% aqueous solution of hydrogen peroxide were added thereto, followed by stirring for further 30 minutes. The reaction mixture was diluted with water and extracted with ethyl acetate. The ethyl acetate layer was washed successively with water and a saline solution, and

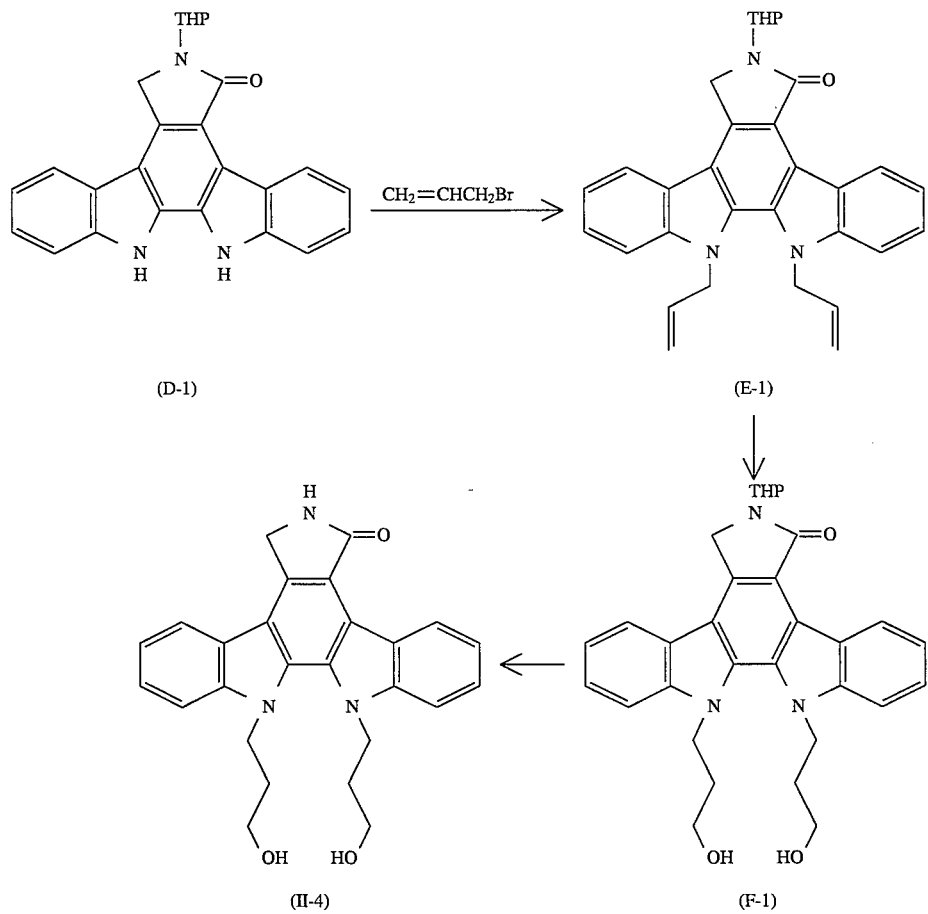

dried over magnesium sulfate. After evaporation of the solvent, the residue was subjected to silica gel column chromatography (chloroform/methanol=15/1) to give 88.9 mg (yield 61%) of Compound (F-1).

$^1$H-NMR (CDCl$_3$) δ (ppm): 1.60–2.11(10H, m), 3.129(2H, t, J=5.9 Hz), 3.192(2H, t, J=5.9 Hz), 3.798(1H, dt, J=2.8, 11.7 Hz), 4.09–4.15(1H, m), 4.723(2H, t, J=7.2 Hz), 4.807(2H, t, J=7.2 Hz), 4.943(1H, d, J=16.6 Hz), 5.107(1H, d, J=16.6 Hz), 5.652(1H, dd, J=2.4, 10.5 Hz), 7.15–7.18(1H, m), 7.318(1H, ddd, J=1.1, 7.0, 8.0 Hz), 7.35–7.39(1H, m), 7.461(1H, ddd, J=1.2, 6.8, 8.0 Hz), 7.519(1H, dd, J=1.0, 8.0 Hz), 7.610(1H, d, J=8.0 Hz), 7.951(1H, d, J=8.0 Hz), 9.490(1H, d, J=8.0 Hz) FAB-MS (m/z): 512 (M+1)$^+$ Compound (F-1) (88.9 mg, 0.174 mmol) was dissolved in 10 ml of tetrahydrofuran, and 8 ml of 4N sulfuric acid was added thereto, followed by stirring at 60° C. for 24 hours. After the reaction mixture was cooled to room temperature, ice was added thereto, followed by extraction with ethyl acetate. The ethyl acetate layer was washed successively with water and a saline solution, and dried over magnesium sulfate- After evaporation of the solvent, the residue was subjected to thin layer chromatography (chloroform/methanol=15/1) to give 37.6 mg (yield 51%) of Compound II-4.

$^1$H-NMR (DMSO-d$_6$) δ (ppm): 1.59–1.65(2H, m), 1.70–1.82(2H, m), 3.03–3.27(2H, m), 3.09–3.14(2H, m), 4.371(1H, t, J=5.0 Hz), 4.419(1H, t, J=5.0 Hz), 4.780(2H, t, J=7.3 Hz), 4.818(2H, t, J=7.4 Hz), 4.972(2H, s), 7.288(1H, ddd, J=0.8, 7.0, 7.8 Hz), 7.370(1H, t, J=7.2 Hz), 7.501(1H, ddd, J=1.2, 7.0, 8.2 Hz), 7.563(1H, ddd, J=1.1, 7.2, 8.3 Hz), 7.779(1H, d, J=8.3 Hz), 7.848(1H, d, J=8.2 Hz), 8.043(1H, d, J=7.2 Hz), 9.412(1H, dd, J=0.8, 7.8 Hz) FAB-MS (m/z): 428 (M+1)$^+$ Preparation of K-252a Derivatives Additional functional derivatives of I-1 can be prepared de novo by chemical synthesis using methods known to those skilled in the art, and by the following procedures, all of which are hereby incorporated by reference. For example, procedures used for preparation of Compound I are described by Murakata et al (U.S. Pat. No. 4,923,986), hereby incorporated by reference. Procedures used for preparation of Compound II are described by Moody et al., J. Org. Chem. 57: 2105–2114 (1992); Steglich et al., Angew. Chem. Int. Ed. Engl. 19: 459–460 (1980); Nakanishi et al., J. Antibiotics 39: 1066–1071 (1986); and Japanese Patent Application No. 60-295172 (1985). Further methods are described for Compound I in Japanese Patent Application Nos. 60-295173 (1985), 62-327858 (1987), 62-327859 (1987) and 60-257652 (1985) [Meiji Seika Kaisha Ltd.].

Therapy

The compounds provided herein can be formulated into pharmaceutical compositions by admixture with pharmaceutically acceptable nontoxic excipients and carriers. As noted above, such compositions can be prepared for use in parenteral administration, particularly in the form of liquid solutions or suspensions; for oral administration, particularly in the form of tablets or capsules; or intranasally, particularly in the form of powders, nasal drops, or aerosols.

The composition can conveniently be administered in unit dosage form and can be prepared by any of the methods well known in the pharmaceutical art, or example, as described in *Remington's Pharmaceutical Sciences* (Mack Pub. Co., Easton, Pa., 1980). Formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or ployoxyethylene-polyoxypropylene copolymers can be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention can be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the prostate disease, the overall health status of the particular patient, the relative biological efficacy of the compound selected, the formulation of the compound excipients, and its route of administration.

Other embodiments are within the following claims.

What is claimed is:

1. A method of treating a pathological condition of the prostate gland in a mammal, said method comprising administering to said mammal a therapeutic amount of an indolocarbazole compound of the formula:

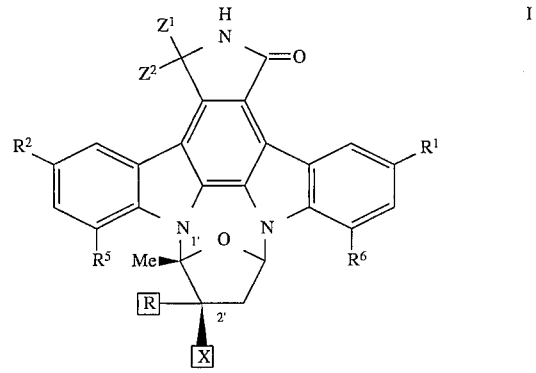

wherein:
a) when $Z^1$ and $Z^2$ are both hydrogen:
  1) R is selected from the group consisting of OH, and O-n-alkyl of 1–6 carbons, and O-acyl of 2–6 carbons;
  2) X is selected from the group consisting of H; CONHC$_6$H$_5$ with the proviso that both $R^1$ and $R^2$ are not Br;
  CH$_2$Y wherein Y is:
    OR$^7$ wherein R$^7$ is H or acyl of 2–5 carbons, acetyl;
    SOR$^8$ wherein R$^8$ is alkyl of 1–3 carbons, aryl, or a heterocyclic group including a nitrogen atom;

NR$^9$R$^{10}$ wherein R$^9$ and R$^{10}$, independently, are H, alkyl of 1–3 carbons, Pro, Ser, Gly, Lys, or acyl of 2–5 carbons, with the proviso that only one of R$^9$ and R$^{10}$ is Pro, Ser, Gly, Lys or acyl; SR$^{16}$ wherein R$^{16}$ is an aryl, alkyl of 1–3 carbons or a heterocyclic group that includes a nitrogen atom;

N$_3$; CO$_2$CH$_3$; S-Glc; CONR$^{11}$R$^{12}$ wherein R$^{11}$ and R$^{12}$, independently, are H, alkyl of 1–6 carbons, C$_6$H$_5$, hydroxyalkyl of 1–6 carbons, or R$^{11}$ and R$^{12}$ are combined to form —CH$_2$CH$_2$OCH$_2$—CH$_2$—; CO$_2$CH$_3$; CH=NNHCONH$_2$; CONHOH; CH=NOH; CH=NNHC(=NH)NH$_2$; and

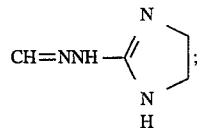

CH=NN(R$^{17}$)$_2$ wherein R$^{17}$ represents aryl; CH$_2$NHCONHR$^{18}$ wherein R$^{18}$ is lower alkyl or aryl; or X and R are combined together to form —CH$_2$NHCO$_2$—, —CH$_2$OC(CH$_3$)$_2$O—, =O, or —CH$_2$N(CH$_3$)CO$_2$—;

3) each R$^1$, R$^2$, R$^5$ and R$^6$, independently, is H or up to two of them are F; Cl; Br; I; NO$_2$; CN; OH; NHCONHR$^{13}$ wherein R$^{13}$ is C$_6$H$_5$ or alkyl of 1–3 carbons with the proviso that only one of R$^1$, R$^2$, R$^5$ and R$^6$ is NHCONHR$^{13}$; CH$_2$OR$^{13}$; alkyl of 1–3 carbons; CH$_2$OCONHR$^{14}$; or NHCO$_2$R$^{14}$; in which R$^{14}$ is lower alkyl; CH(SC$_6$H$_5$)$_2$ or CH(—SCH$_2$CH$_2$S—); or R$^1$ is CH$_2$S(O)$_p$R$^{21}$ where p=0 or 1 and R$^{21}$ is aryl, alkyl of 1–3 carbons, a heterocyclic group that includes a nitrogen atom,

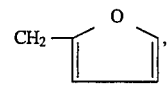

or CH$_2$CH$_2$N(CH$_3$)$_2$, and R$^2$ R$^5$ and R$^6$ are H; or R$^1$ is CH=NNR$^{22}$R$^{23}$, wherein R$^{22}$ and R$^{23}$, are each independently H, alkyl of 1–3 carbons, C(=NH)NH$_2$, or a heterocyclic group that includes a nitrogen atom, or R$^{22}$ and R$^{23}$ are combined together to form —(CH$_2$)$_4$—, —(CH$_2$CH$_2$OCH$_2$CH$_2$)—, or —(CH$_2$CH$_2$N(CH$_3$)CH$_2$CH$_2$)—, with the proviso that R$^{22}$ and R$^{23}$ cannot both be H, and at least one of R$^{22}$ or R$^{23}$ is H except when both are alkyl, and R$^2$, R$^5$ and R$^6$ are H;

and b) when Z$^1$ and Z$^2$ are both combined together to represent O; X is CO$_2$CH$_3$; R is OH and R$^1$, R$^2$, R$^5$ and R$^6$ are each hydrogen.

2. The method of claim 1, wherein said pathological condition is benign prostatic hypertrophy.

3. The method of claim 1, wherein said pathological condition is prostate cancer.

4. The method of claim 1, wherein the activity of trks in the presence of said compound is less than the activity of said trks in the absence of said compound.

5. A method of treating a pathological condition of the prostate gland in a mammal, said method comprising administering to said mammal a therapeutic amount of an indolocarbazole compound selected from the group consisting of

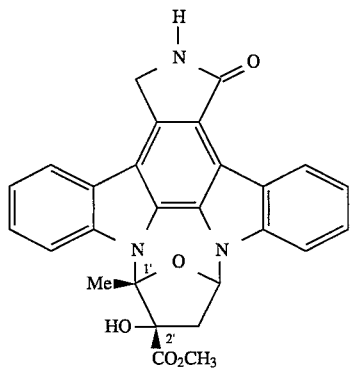

I-1

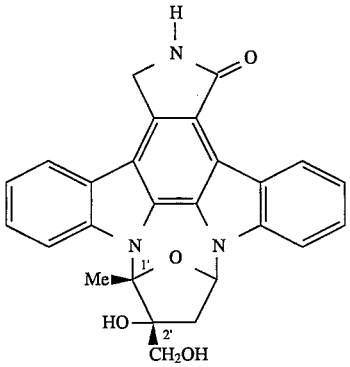

I-2

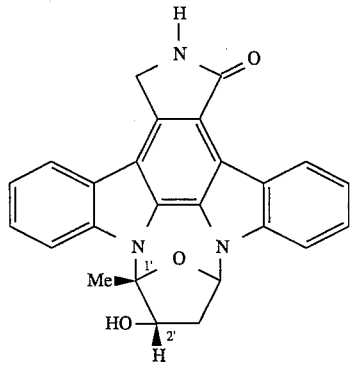

I-3

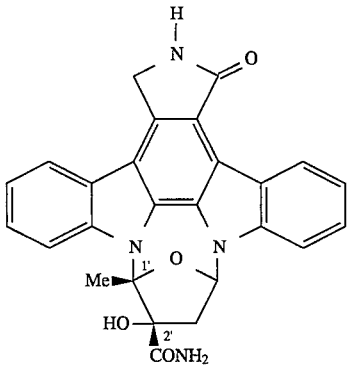

I-4

-continued
I-5
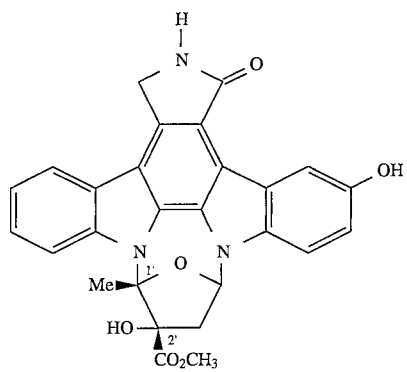
I-6
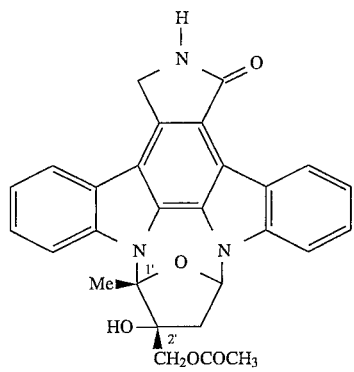
I-7
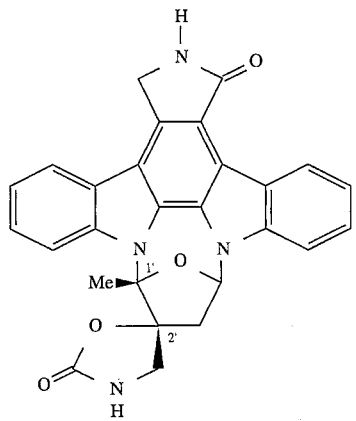
I-8
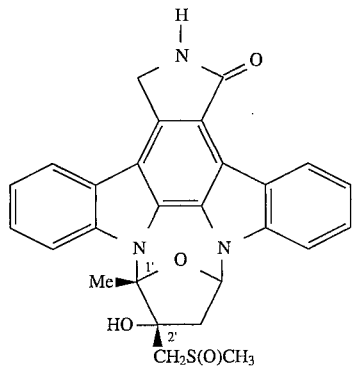
I-9
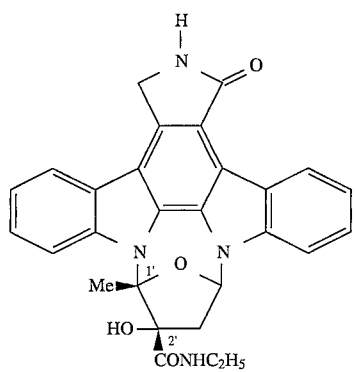
I-10
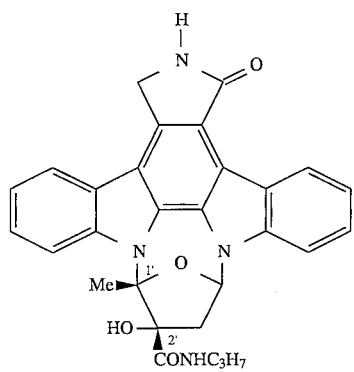
I-11
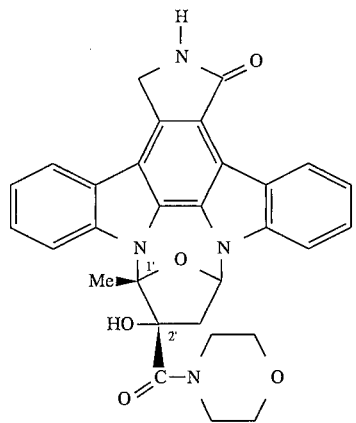
I-12
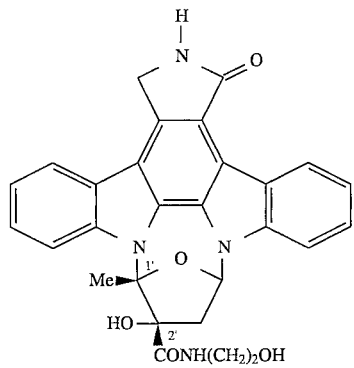

I-13
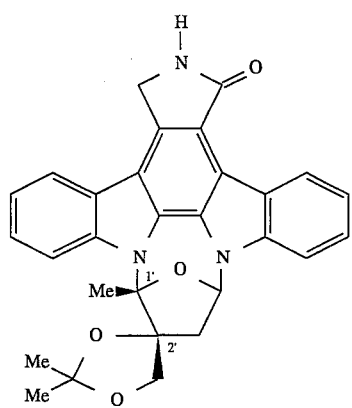
I-14
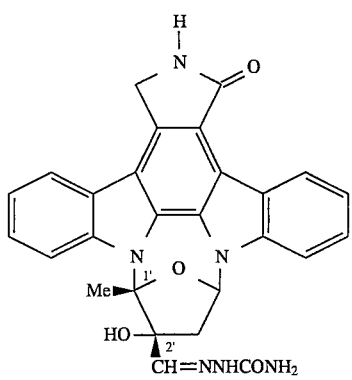
I-15
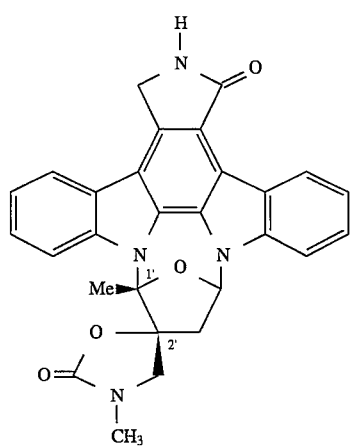
I-16
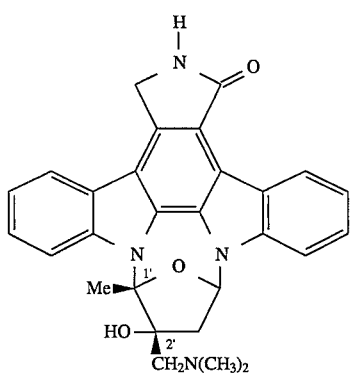
I-17
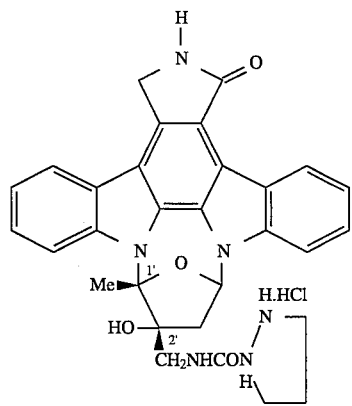
I-18
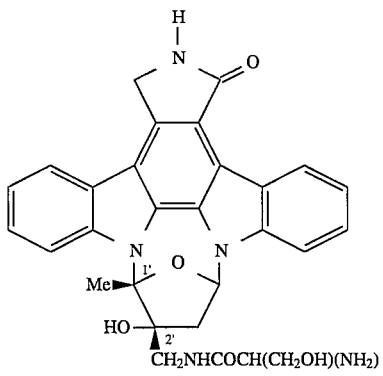
I-19
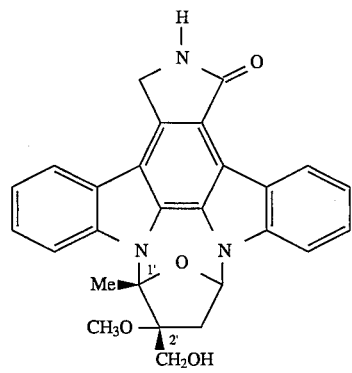
I-20
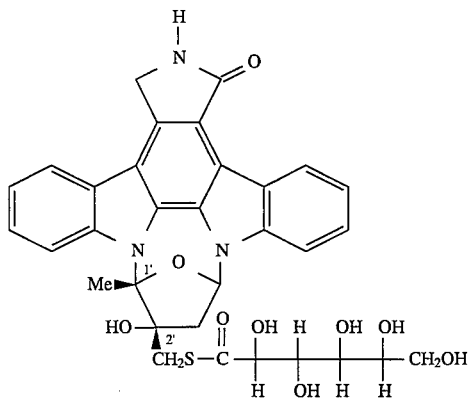

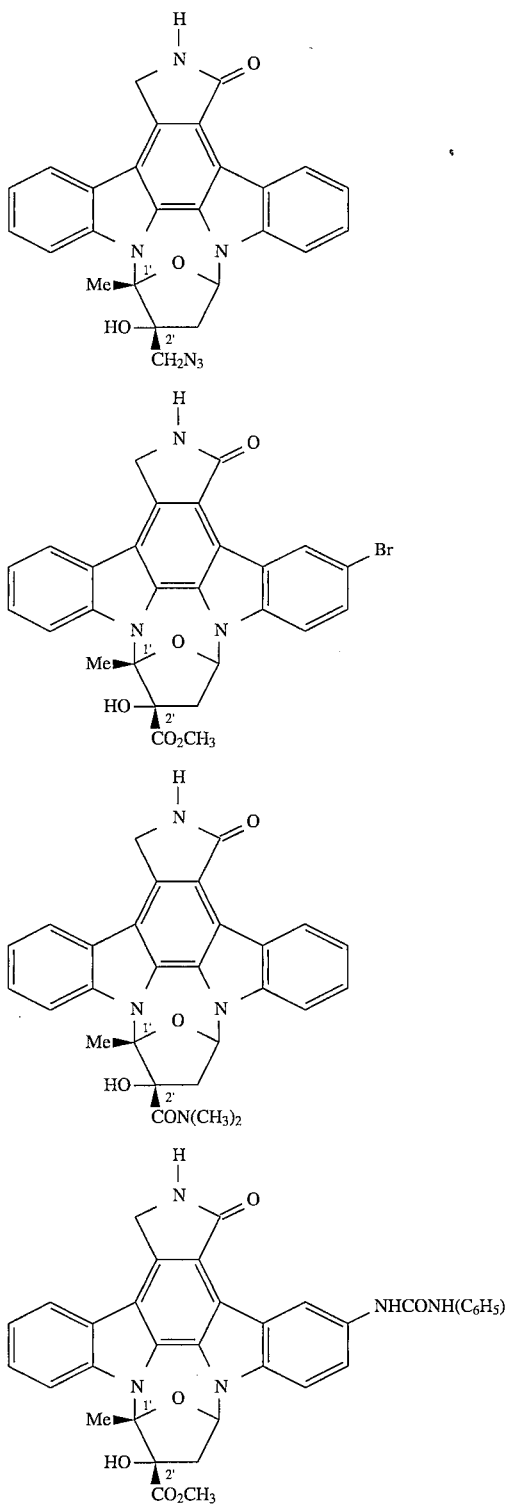
I-21
I-23
I-25
I-27
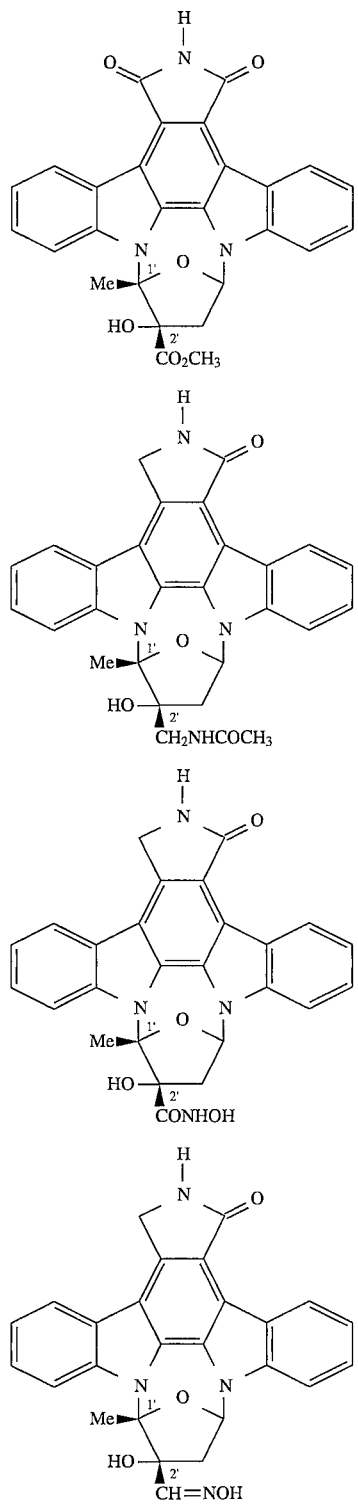
-continued
I-22
I-24
I-26
I-28

53 54
I-29
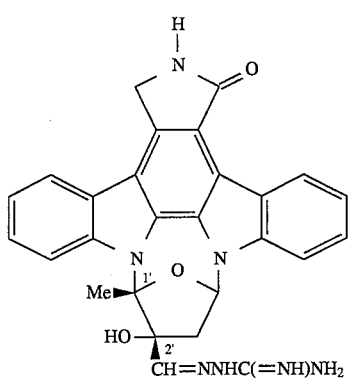
I-30
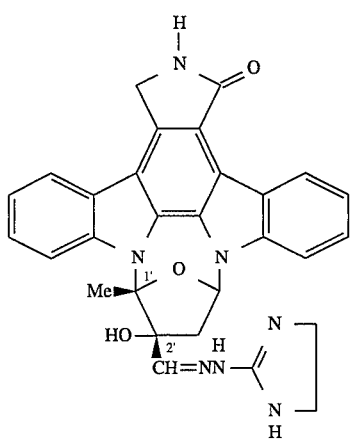
I-31
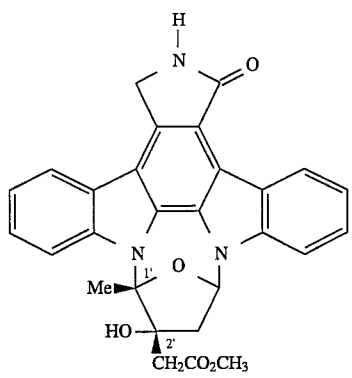
I-32
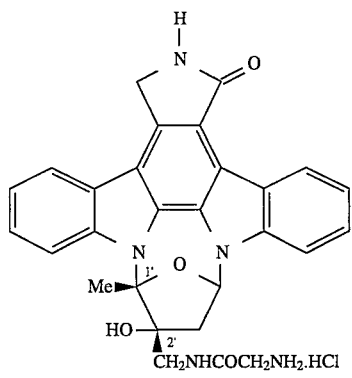
I-33
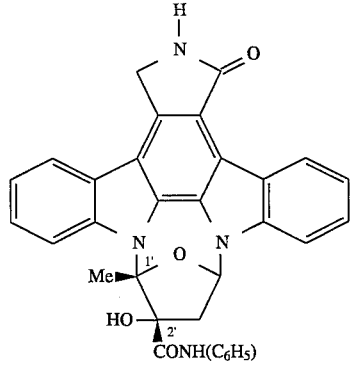
I-34
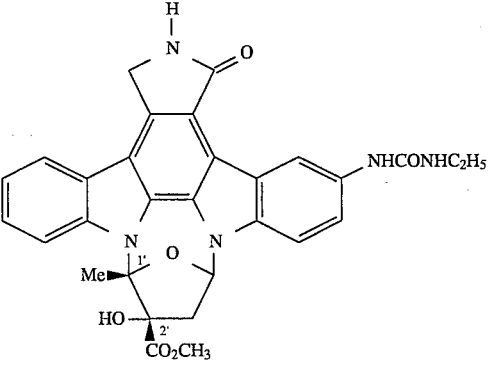
I-35
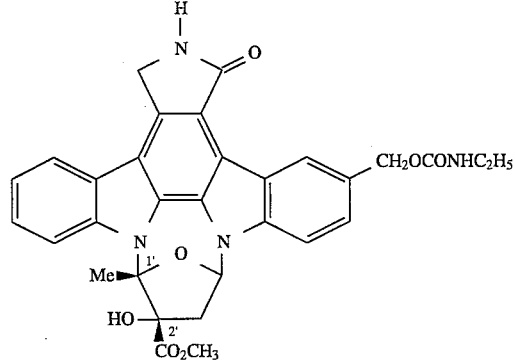
I-36
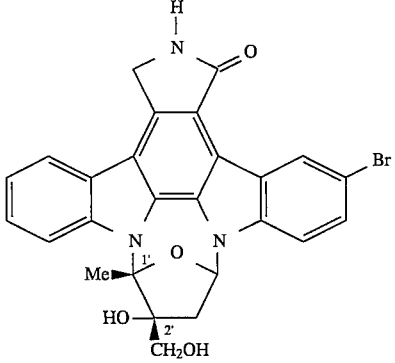

-continued
I-37
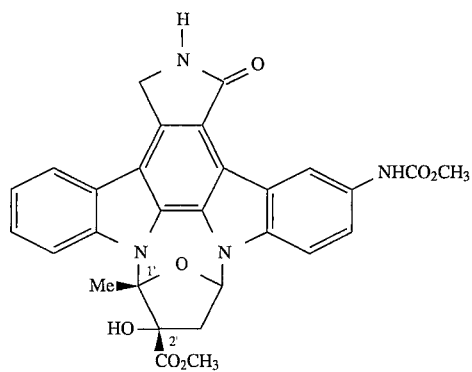
I-38
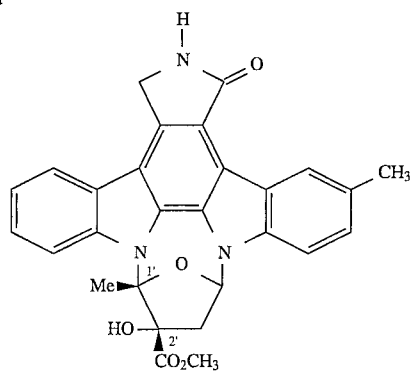
I-39
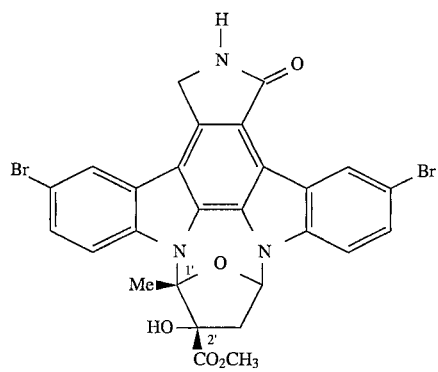
I-40
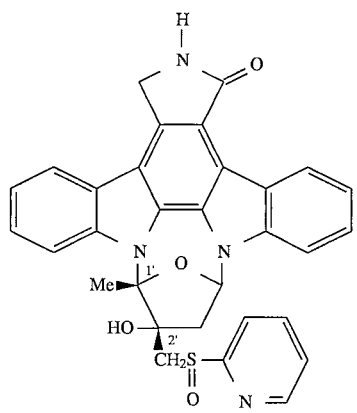
I-41
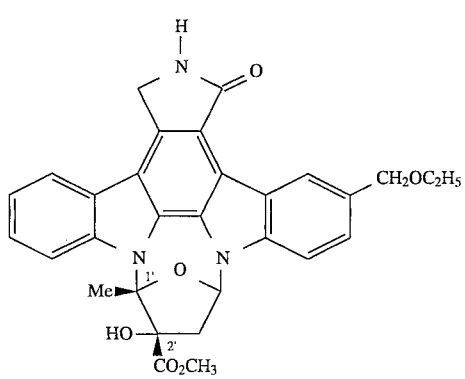
I-42
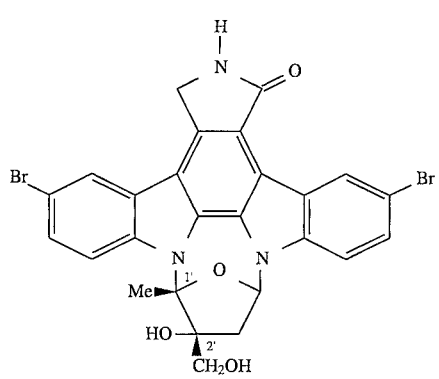
I-43
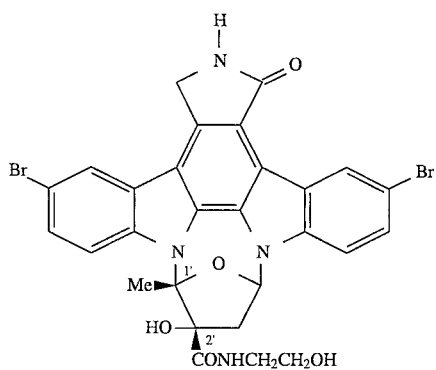
I-44
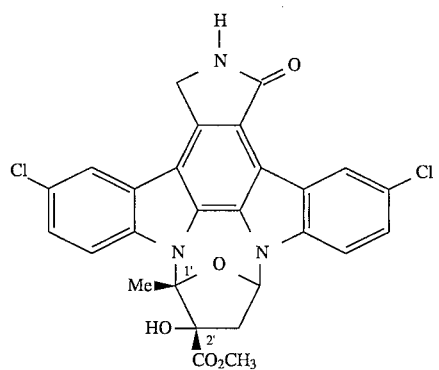

-continued
I-45
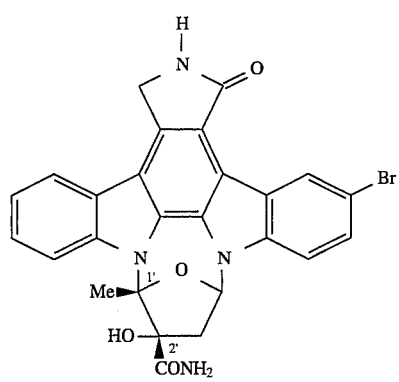
I-46
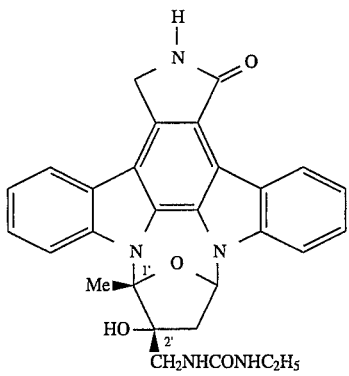
I-47
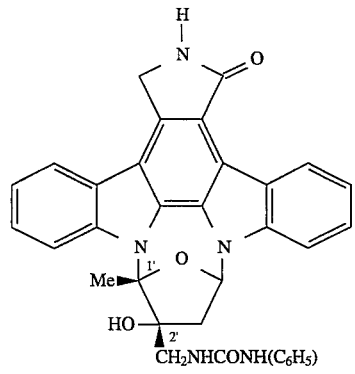
I-48
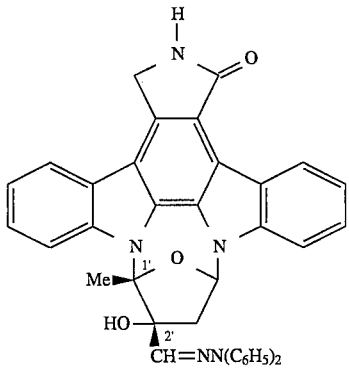
I-49
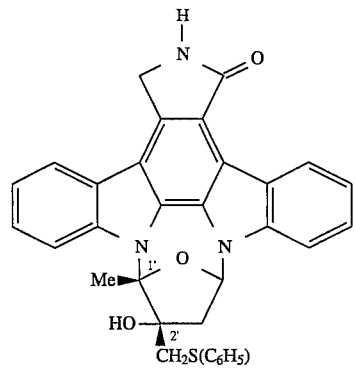
I-50
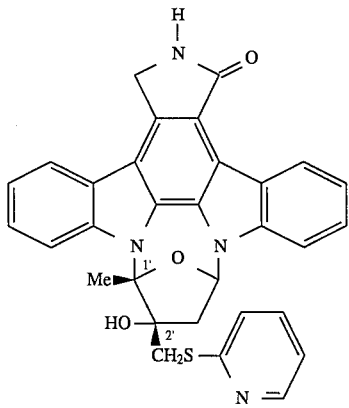
I-51
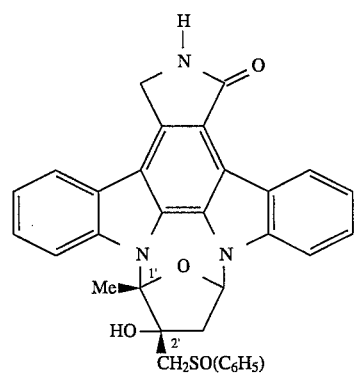
I-52
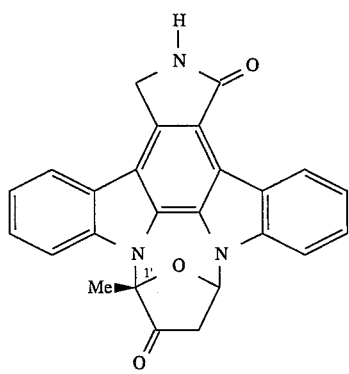

I-53 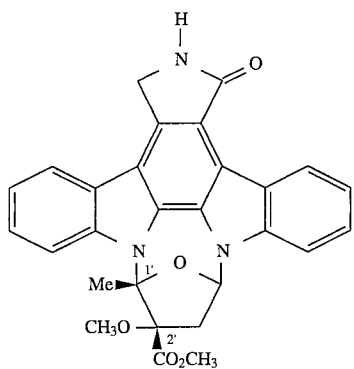
I-55 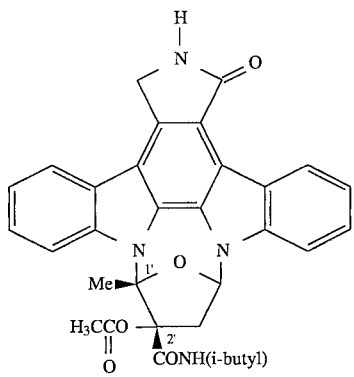
I-57 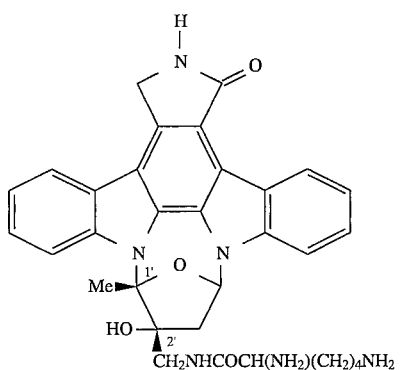
I-59 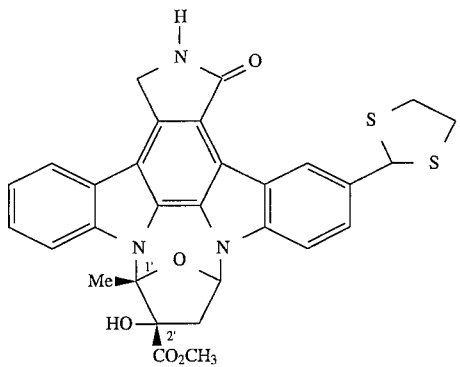
I-54 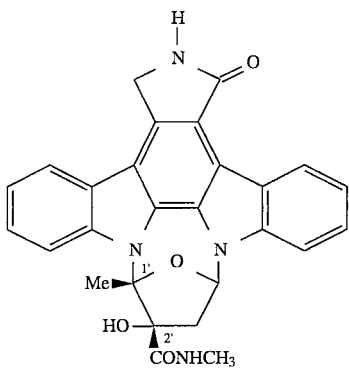
I-56 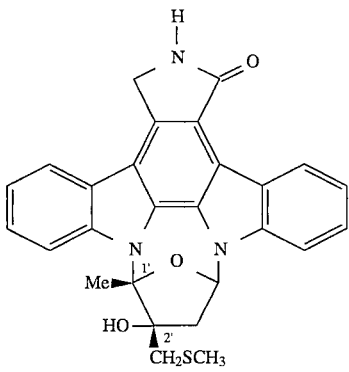
I-58 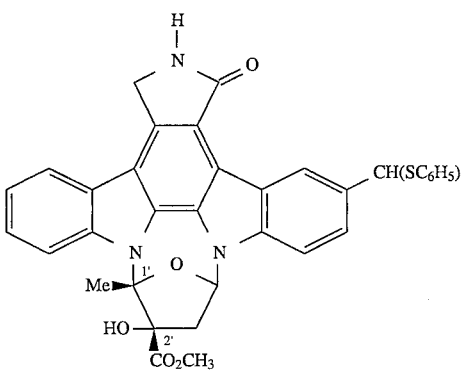
I-60 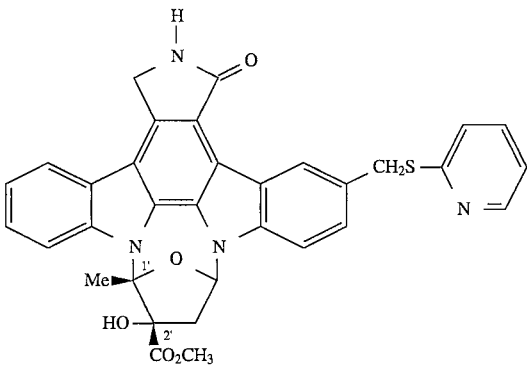

-continued
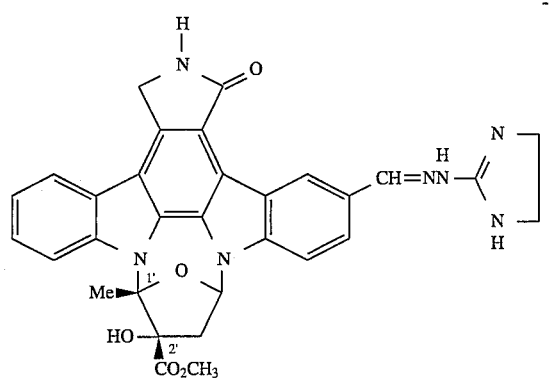
I-61
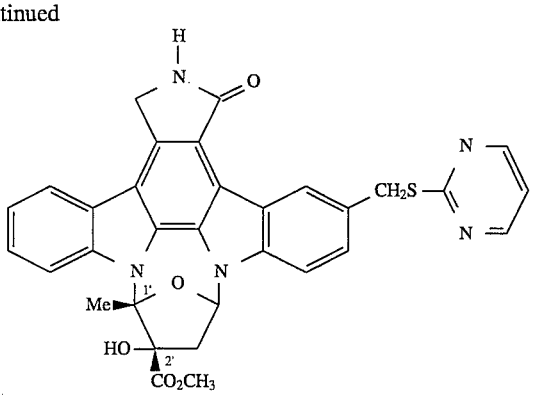
I-62
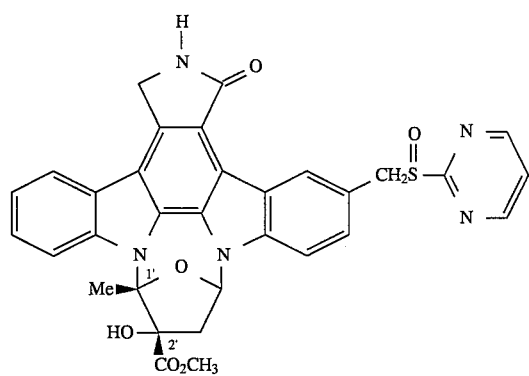
I-63
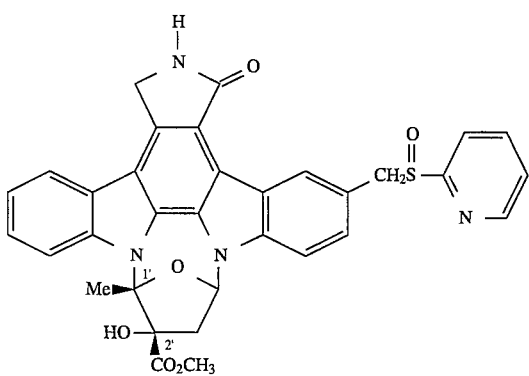
I-64
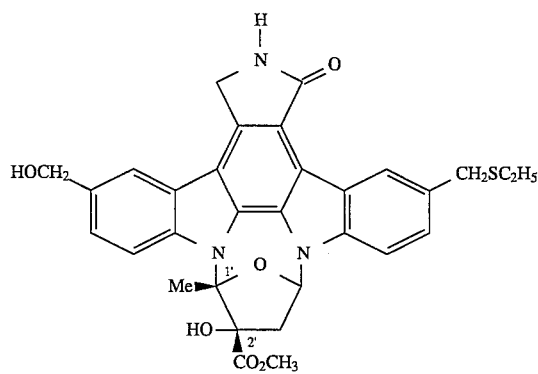
I-65
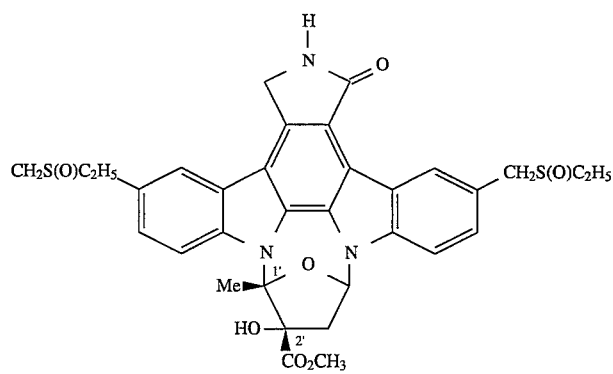
I-66

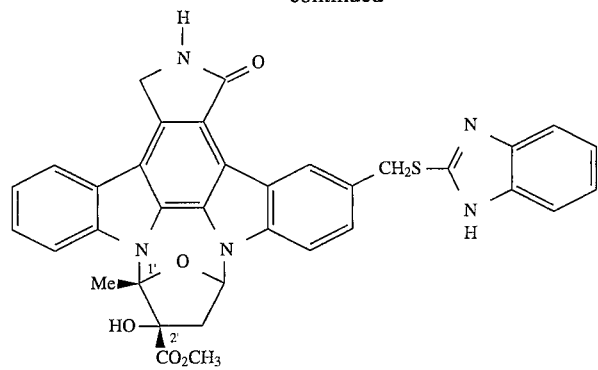
I-67
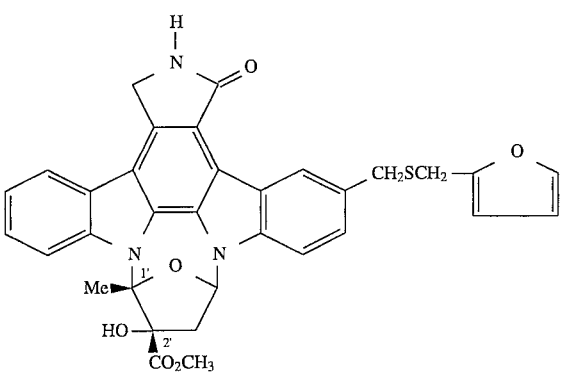
I-68
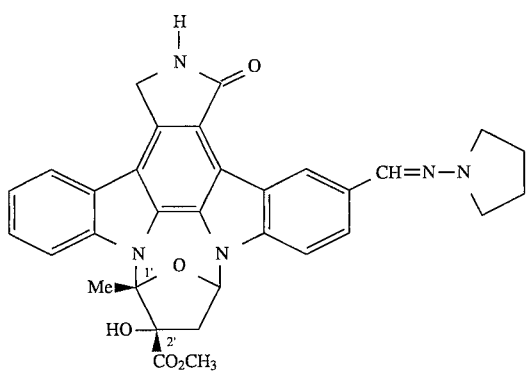
I-69
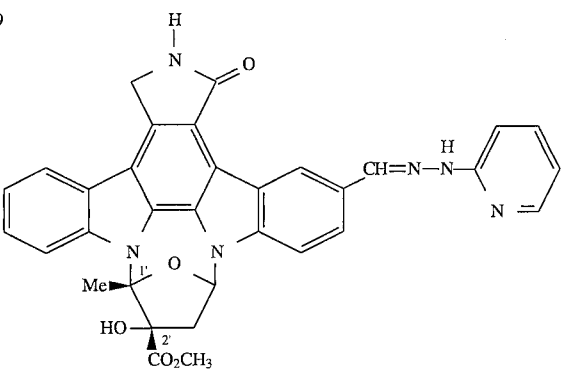
I-70
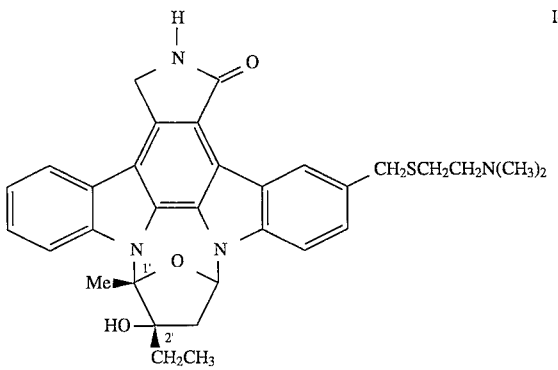
I-71
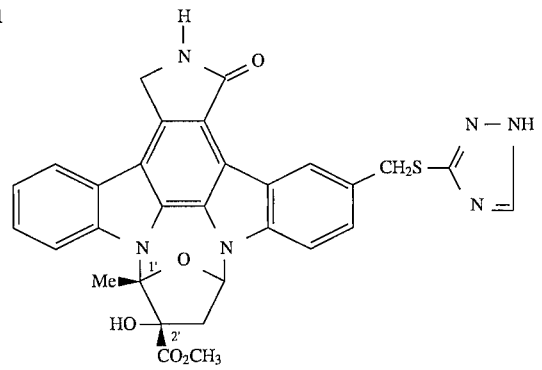
I-72

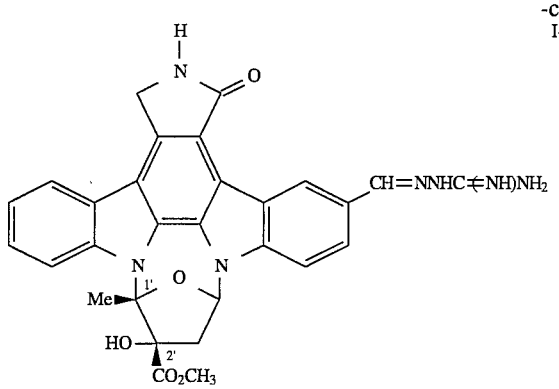
I-73
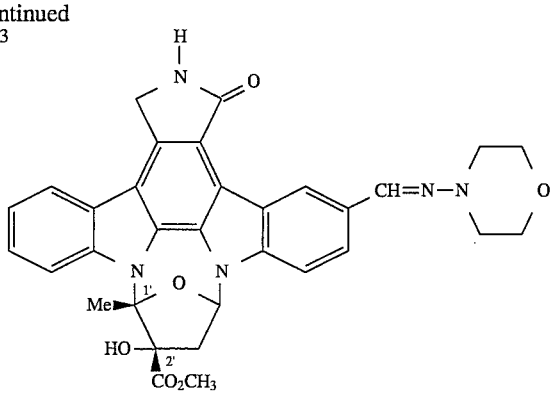
I-74
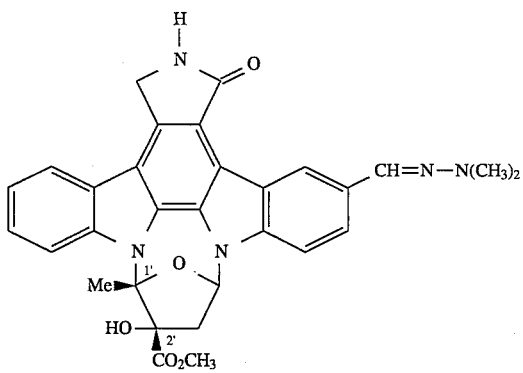
I-75
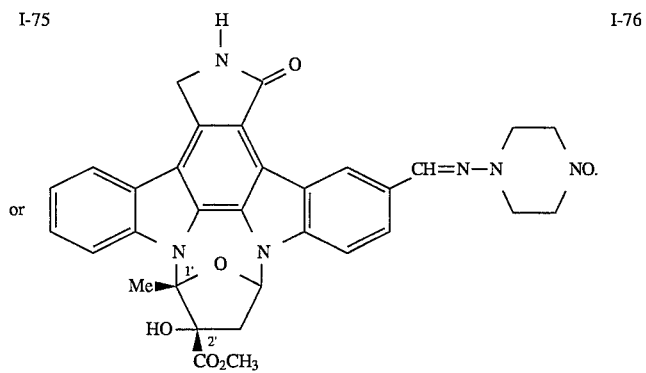
I-76
or
6. The method of claim 5, wherein said indolocarbazole compound is selected from the group consisting of
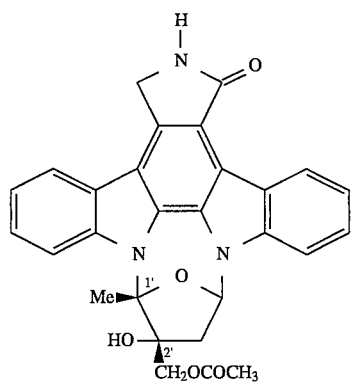
I-6
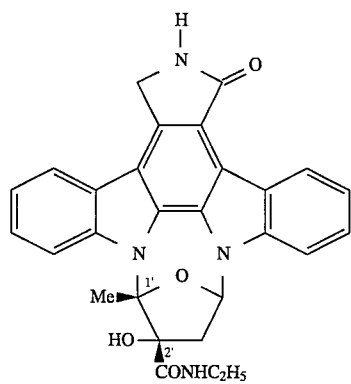
I-9
-continued
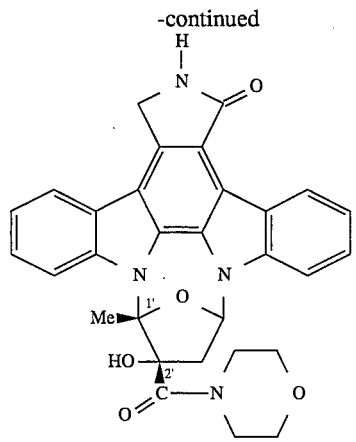
I-11
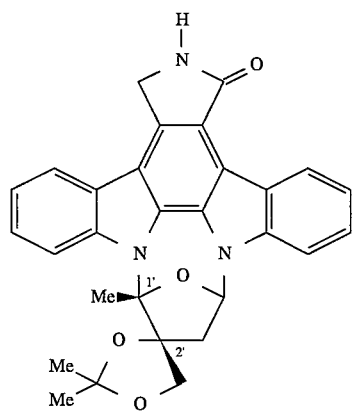
I-13

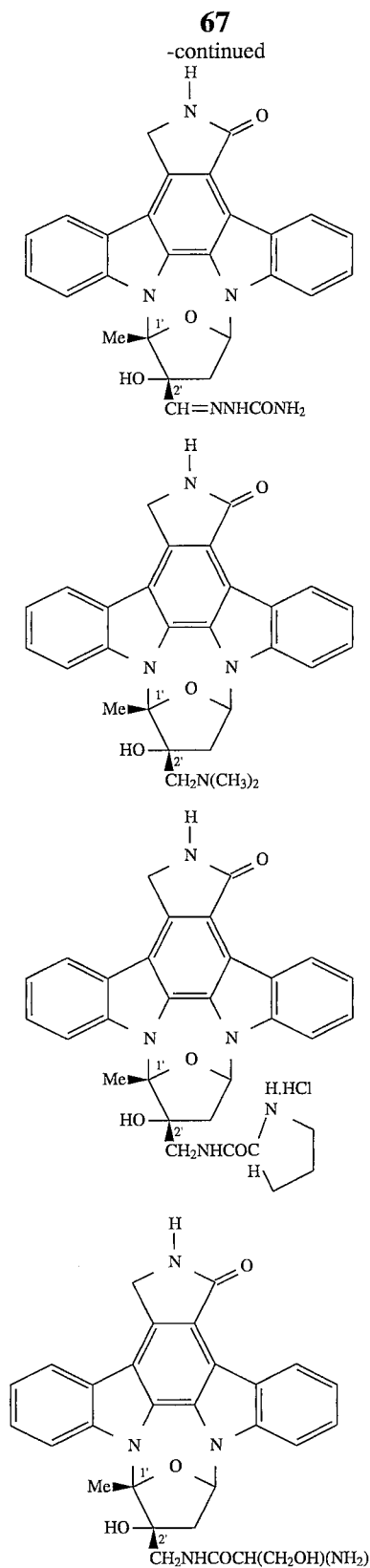
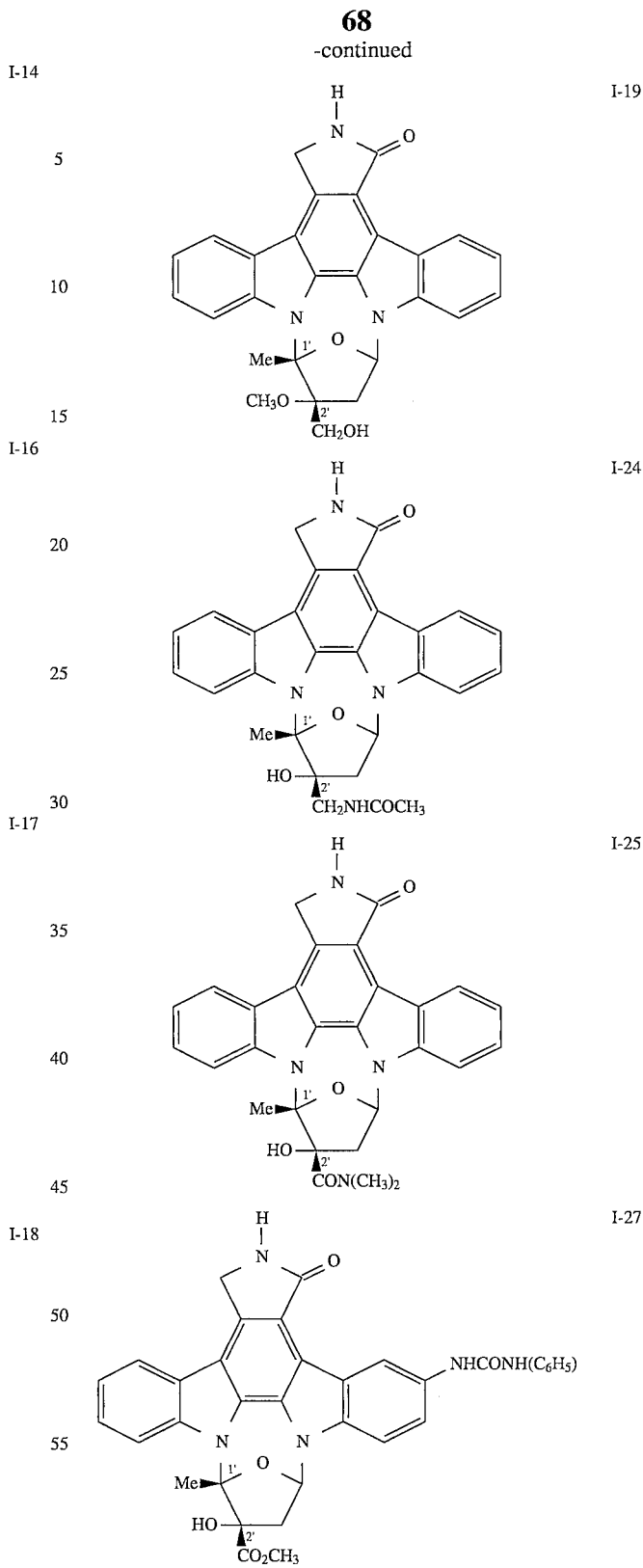

-continued
I-31
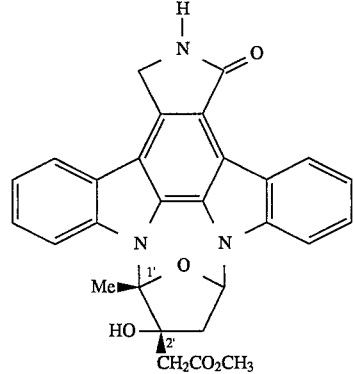
I-33
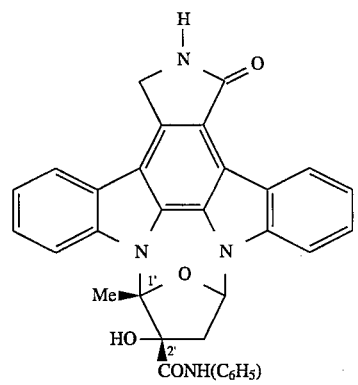
I-34
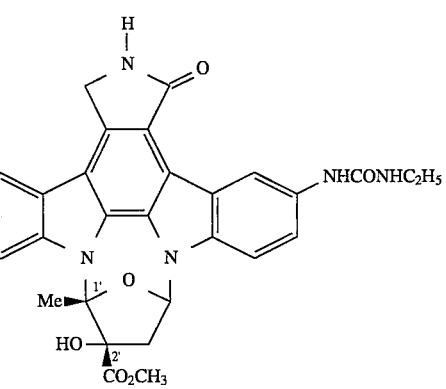
I-35
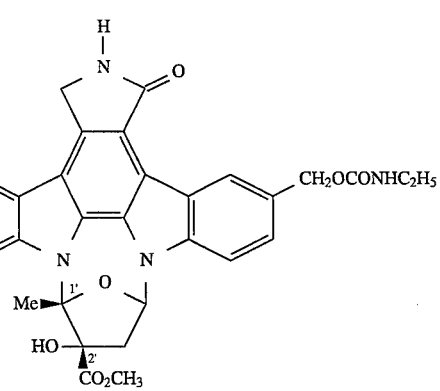
I-37
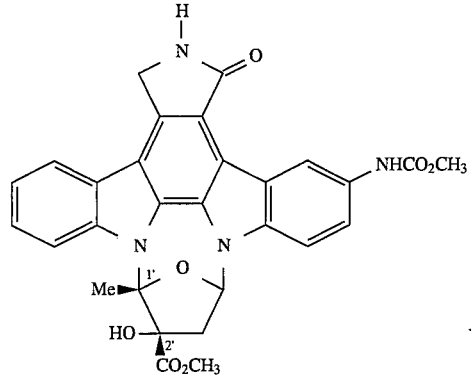
I-40
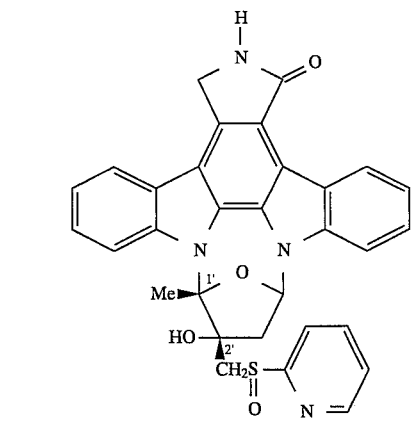
I-41
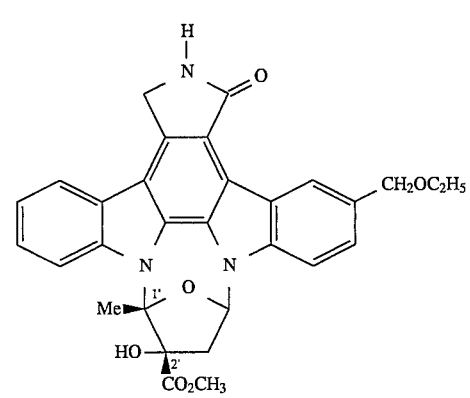
I-43
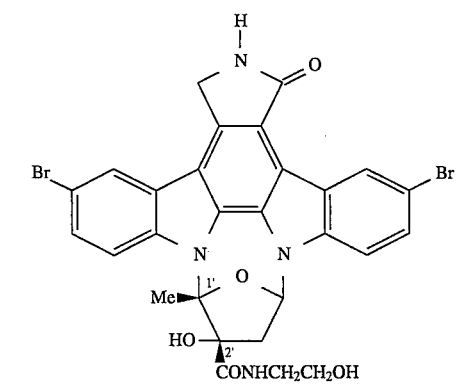

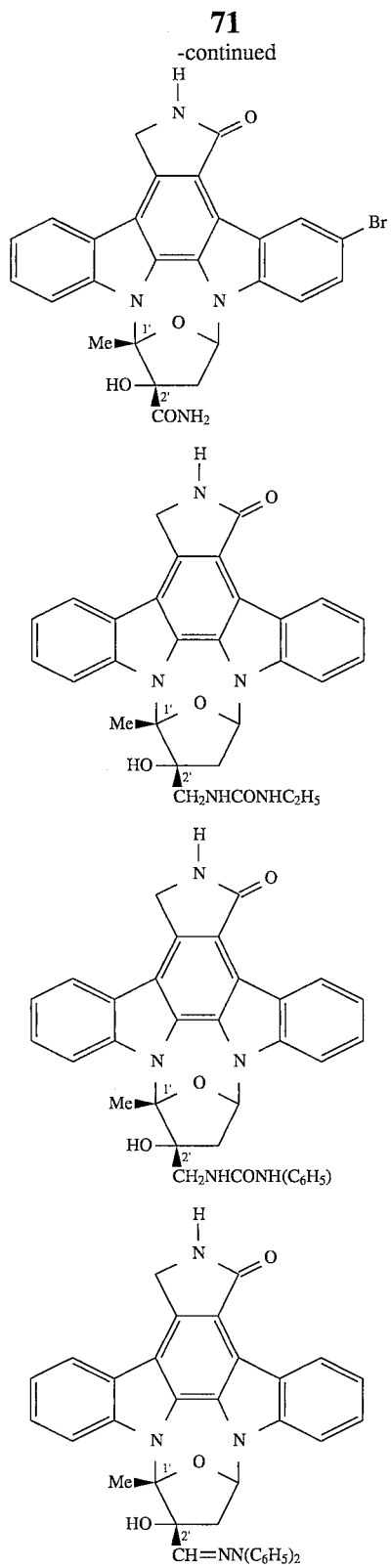
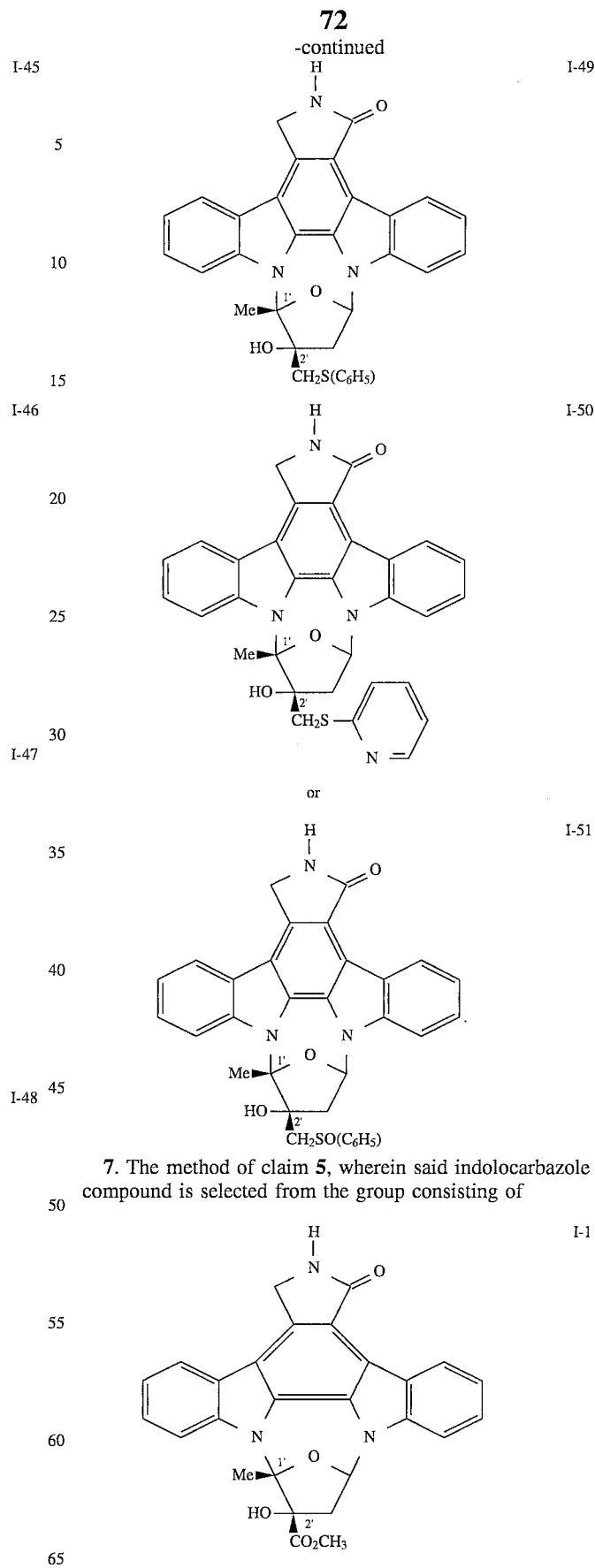
7. The method of claim 5, wherein said indolocarbazole compound is selected from the group consisting of 5,516,771
73
-continued
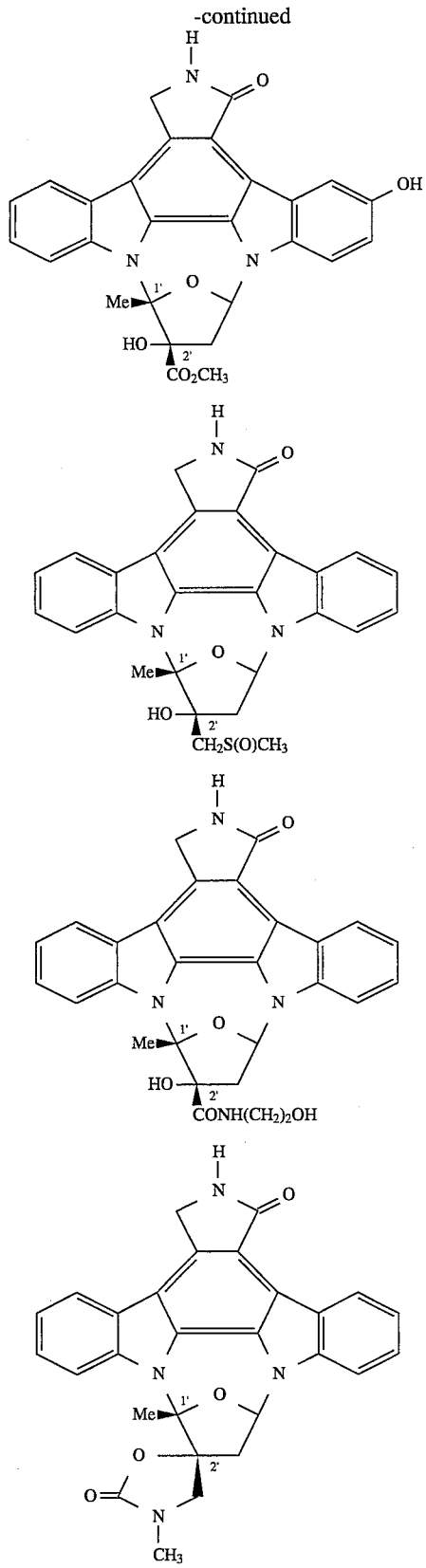
74
-continued
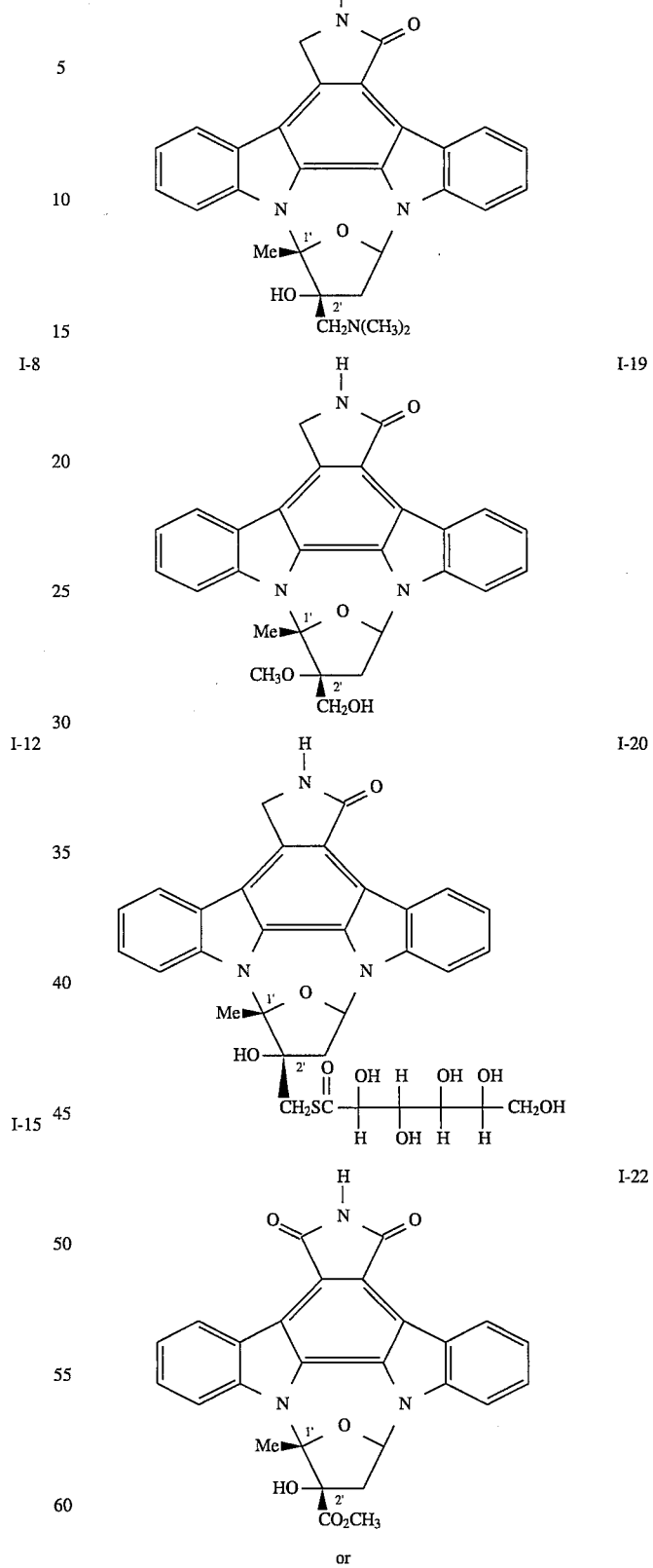
or -continued
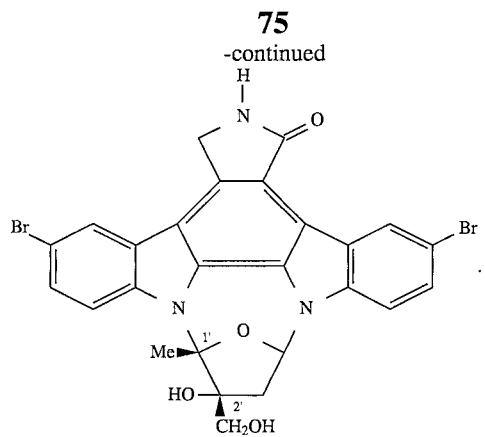
I-42
8. The method of claim 5, wherein said compound is
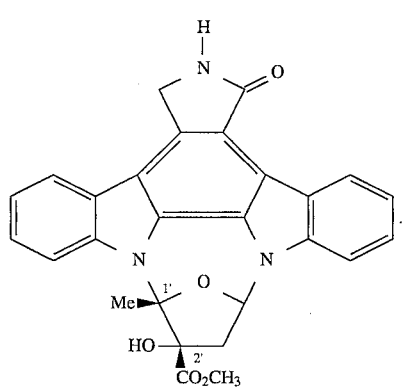
I-1
9. The method of claim 5, wherein said compound is
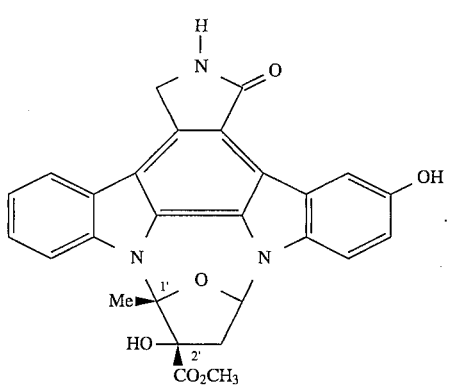
I-5
10. The method of claim 5, wherein said compound is
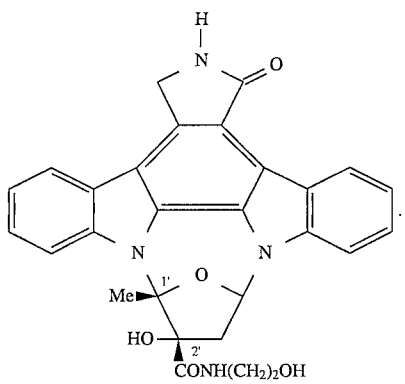
I-12
11. The method of claim 5, wherein said compound is
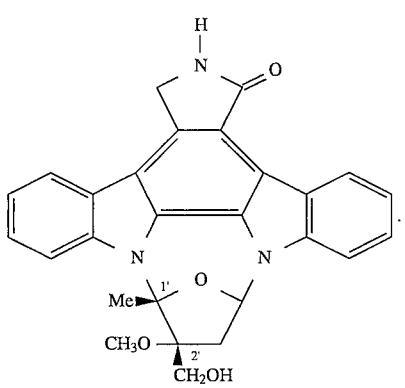
I-19
12. The method of claim 5, wherein said compound is
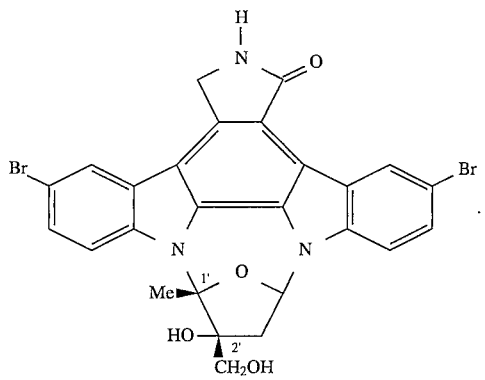
I-42
* * * * *

UNITED STATES PATENT AND TRADEMARK OFFICE
CERTIFICATE OF CORRECTION

PATENT NO. : 5,516,771           Page 1 of 3
DATED       : May 14, 1996
INVENTOR(S) : Craig A. Dionne, et al.

It is certified that error appears in the above-indentified patent and that said Letters Patent is hereby corrected as shown below:

On the title page, under "OTHER PUBLICATIONS", "Berg et al." replace "Photo-Oncogene" with --Proto-Oncogene--.
On the title page, under "OTHER PUBLICATIONS", replace "Mac Morgan et al." with --Mac Grogan et al--.

Col. 9, line 22, replace "I1" with --I-1--;

Col. 9, line 33, replace "prostrate" with --prostate--;

Col. 15, line 54, replace "Oreg." with --OR--;

Col. 25, line 21, replace "4,982" with --4.982--;

Col. 26, line 4, replace "(PR-3;" with --(P-3;--;

Col. 27, line 13, replace "25 (0.3 mmol)" with --25 $\mu$l (0.3 mmol)--;

Col. 27, line 61, replace "(3H, s)$_{2.607}$" with --(3H, s) 2.607--;

Col. 32, line 37, replace "$CPCO_2R^{14}$" with --$ClCO_2R^{14}$;

UNITED STATES PATENT AND TRADEMARK OFFICE
CERTIFICATE OF CORRECTION

PATENT NO. : 5,516,771                                    Page 2 of 3
DATED      : May 14, 1996
INVENTOR(S): Craig A. Dionne, et al.

It is certified that error appears in the above-indentified patent and that said Letters Patent is hereby corrected as shown below:

Col. 36, line 13, replace "5 to 24 hours at to 100°C." with --5 to 24 hours at 50 to 100°C.--;

Col. 36, line 17, replace "$CH(SC_6H_6)_2$" with --$CH(SC_6H_5)_2$--;

Col. 38, line 54, replace "ar" with --are--;

Col. 39, line 30 and after the compound, add the following: --SI-MS (m/z): 835 $(M+1)_+$--;

Col. 40, line 27, replace "(yield of N,O-diacetylated..." with --(yield 96% of N,O-diacetylated...--;

Col. 42, lines 1-2, replace "(J. Chem. Soc. Perkin Trans. 1:2475, 823.7 mg, 2.083 mmol)" with --(J. Chem. Soc. Perkin Trans. 1:2475, 1990) (823.7 mg, 2.083 mmol)--;

Col. 42, line 22, replace "0,287" with --0.287--;

UNITED STATES PATENT AND TRADEMARK OFFICE
CERTIFICATE OF CORRECTION

PATENT NO. : 5,516,771

DATED : May 14, 1996

INVENTOR(S) : Craig A. Dionne, et al.

It is certified that error appears in the above-indentified patent and that said Letters Patent is hereby corrected as shown below:

Col. 49, claim 5, at 1-17, replace "$CH_2NHCON$" with --$CH_2NHCOC$--.

Signed and Sealed this

Twenty-second Day of October, 1996

Attest:

BRUCE LEHMAN

*Attesting Officer*   *Commissioner of Patents and Trademarks*